(12) United States Patent
Chen et al.

(10) Patent No.: US 9,884,101 B2
(45) Date of Patent: Feb. 6, 2018

(54) TREATMENT AND PREVENTION OF MALARIA

(71) Applicants: Lin Chen, Parkville (AU); Alan Cowman, Parkville (AU); Tony Triglia, Parkville (AU)

(72) Inventors: Lin Chen, Parkville (AU); Alan Cowman, Parkville (AU); Tony Triglia, Parkville (AU)

(73) Assignee: The Walter and Eliza Hall Institute for Medical Research, Parkville, Victoria (AU)

( * ) Notice: Subject to any disclaimer, the term of this patent is extended or adjusted under 35 U.S.C. 154(b) by 0 days.

(21) Appl. No.: 14/813,739

(22) Filed: Jul. 30, 2015

(65) Prior Publication Data
US 2015/0366958 A1 Dec. 24, 2015

Related U.S. Application Data

(63) Continuation-in-part of application No. 13/884,604, filed as application No. PCT/AU2011/001442 on Nov. 8, 2011, now Pat. No. 9,109,040.

(60) Provisional application No. 61/435,602, filed on Jan. 24, 2011, provisional application No. 61/411,598, filed on Nov. 9, 2010.

(51) Int. Cl.
*A61K 39/015* (2006.01)
*C07K 16/20* (2006.01)

(52) U.S. Cl.
CPC .......... *A61K 39/015* (2013.01); *C07K 16/205* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,703,147 B2 | 4/2014 | Cowman et al. | |
| 2009/0175895 A1* | 7/2009 | Cowman et al. | 424/191.1 |
| 2009/0202579 A1* | 8/2009 | Cowman | C07K 14/445 424/191.1 |
| 2011/0311571 A1 | 12/2011 | Cowman et al. | |

OTHER PUBLICATIONS

Volkman et al. Accessions No. A0A0L07MC4 ,Sep. 2006.*
Volkman et al. Accessions No. A0a)L0CXG4 , Sep. 2006.*
Bowman et al. (Nature vol. 400, pp. 532-538, 1999).*
Chen et al., "An EGF-like protein forms a complex with PfRh5 and is required for invasion of human erythrocytes by Plasmodium falciparum", PLOS Pathogens, 2011, 7:e1002199.
Healer et al., "Vaccination with conserved regions of erythrocyte-binding antigens induces neutralizing antibodies against multiple strains of Plasmodium falciparum", PLOS One, 2013, 8:e72504.
Reed et al., "Targeted disruption of an erythrocyte binding antigen in Plasmodium falciparum is associated with a switch toward a sialic acid-independent pathway of invasion", Proc National Acad Sci, 2000, 97:7509-7514.
Breman, et al., Am J Trop Med Hyg, "Conquering the Intolerable Burden of Malaria: What's New, What's Needed: A Summary," 2004; 71(Suppl 2): 1-15.
Duraisingh, et al., The EMBO Journal, "Phenotypic variation of Plasmodium falciparum merozoite proteins directs receptor targeting for invastion of human erythrocytes," 2003; 22: 1047-1057.
George, et al., Protein Engineering, "An analysis of protein domain linkers: their classification and role in protein folding," 2003; 15: 871-879.
Harayama, Trends Biotech, "Artificial evolution by DNA shuffling," 1998; 16: 76-82.
Hay, et al., Lancet Infect Dis, "The global distribution and population at risk of malaria: past, present, and future," 2004; 4: 327-336.
Hoffmann, et al., J Infect Dis, "Protection of Humans against Malaria by Immunization with Radiated-Attenuated Plasmodium falciparum Sporozoites," 2002; 185: 1155-1164.
Needleman, et al., J Mol Biol, "A General Method Applicable to the Search for Similarities in the Amino Acid Sequence of Two Proteins," 1970; 48: 443-453.
Ohta, et al., Tokai J Exp Clin Med, "Screening of HLA-DR-Restricted Helper T-cell Epitopes of MSP1 of Plasmodium falciparum in Humans," 1998; 23: 85.
Paolicelli, et al., Nanomedicine, "Surface-modified PLGA-based nanoparticles that can efficiently associate and deliver virus-like particles," 2010; 5: 843-853.
Rammensee, Curr Opin Immunol, "Chemistry of peptides associated with MHC class I and class II molecules," 1995; 7: 85-96.
Singh, et al., PLoS One, "Helper T Cell Epitope-Mapping Reveals MHC-Peptide Binding Affinities that Correlate with T Helper Cell Responses to Pneumococcal Surface Protein A," 2010; 5: 39435.
Snow, et al., Am J Trop Med Hyg, "Pediatric Mortality in Africa: Plasmodium Falciparum Malaria as a Cause or Risk?" 2004; 71(Suppl 2): 16-24.
Sun, et al., Vaccine, "Advances in saponin-based adjuvants," 2009; 27: 1787-1796.
Wang, et al., PNAS USA, "Induction of CDR+ T cell-dependent CD8+ type 1 responses in humans by a malaria DNA vaccine," 2001; 98: 10817-10822.
GenBank Accession No. CAB39049 & XM_001351269, Conserved Plasmodium protein, unknown function [Plasmodium falciparum 3D7].

* cited by examiner

Primary Examiner — J. Hines
Assistant Examiner — Khatol Shahnan Shah
(74) Attorney, Agent, or Firm — Klauber & Jackson LLC

(57) ABSTRACT

The present invention relates to recombinant fragments of *Plasmodium* polypeptides and polynucleotides encoding same. The invention further relates to compositions comprising the recombinant fragments of *Plasmodium* polypeptides and their use in the treatment and prevention of malaria.

3 Claims, 17 Drawing Sheets

1A
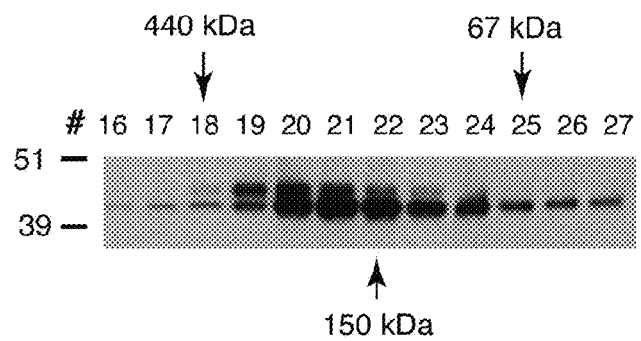
1B
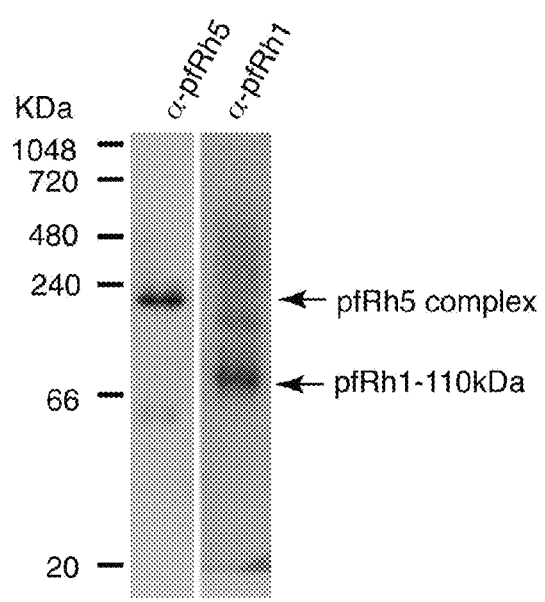
Figure 1

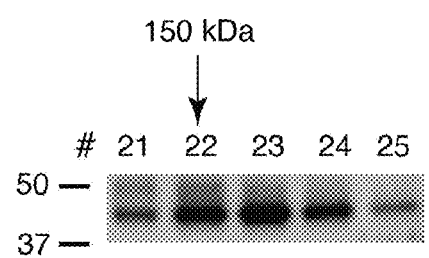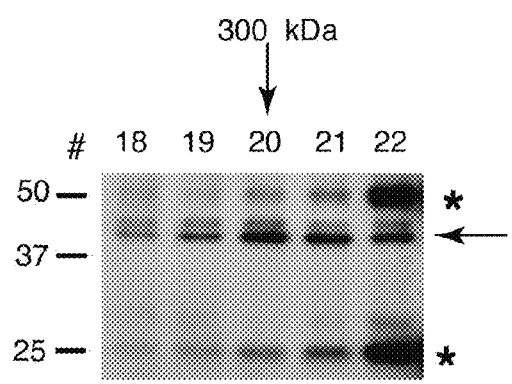
Figure 2

3A
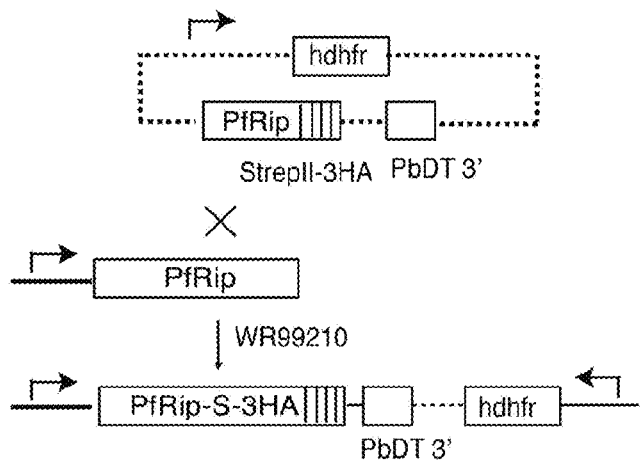
3B
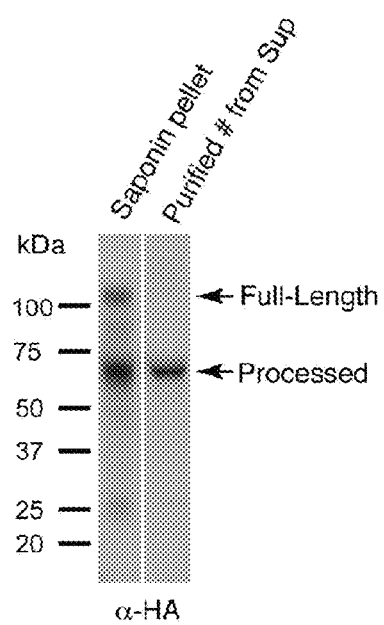
3C
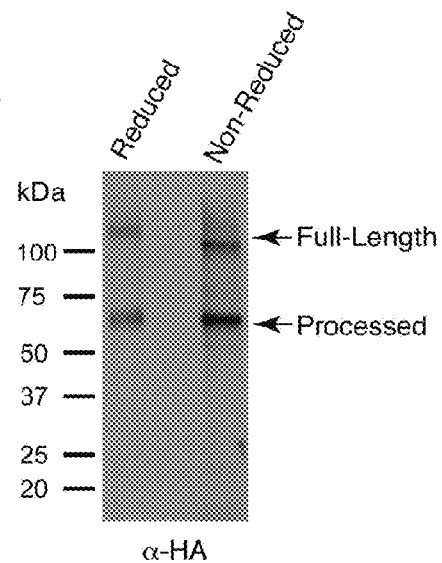
Figure 3

6A

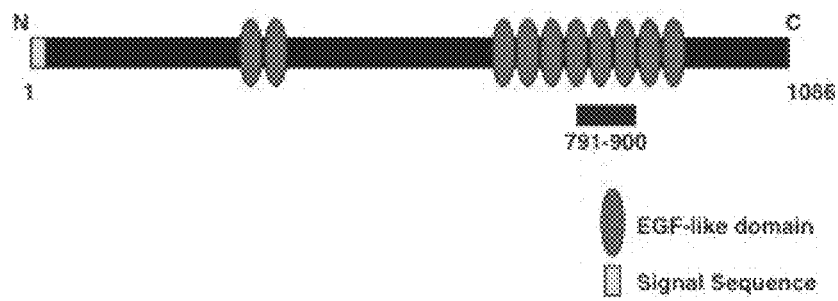

6B

```
287 RCTQ....DICSV.NQFCDGE....NETCTCKTSLL..PSAKNNCE
325 LCTV....LNCPE.NSTCEQIGNGKKAECKCENGKY..YHNNKCY
636 SCSN..LCNKCHN.NSTCYGNRF..NYDCFCDNPYISKYGNKLCE
679 DCES....VLCSQ.NQVCQILPN.DKLICQCEEGYK..NVKGCV
719 KCD.....LSCPS.NKVCVIENG..KQTCKCSERFV..LENGVCI
771 KCRKEYENICTNPNEMCAYNEETDIVKCECKEHYY.RSSRGECI
818 YCK....DINCKE.NEECSIVNF..KPECVCKENLK..KNNKGECI
858 SCLIN..EGNCPK.DSKCIYREY..KPHECVCNKQGH..VAVNGKCV
901 KCVHN...KKCSE.NSICVNMK..EPICVCTYNYY..KKDGVCL
942 PCLKD..NGGCSR.NSECTFKYS..KINCTCKENYK..NKDDSCV

EGF ECPLS.HDGYCLH.DGVCMYIEALDKYACNCVVGYI....GERCQ
```

6C
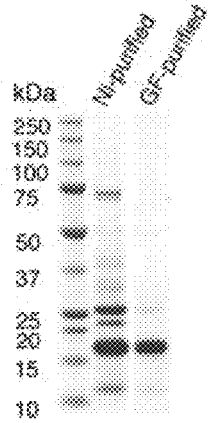

6D
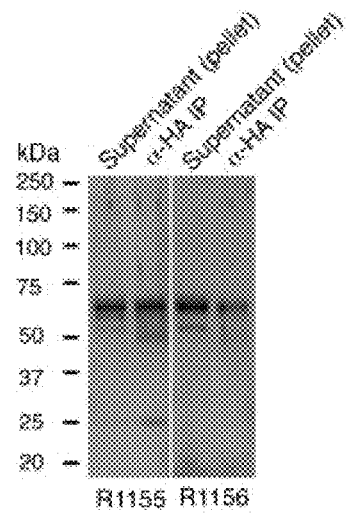

Figure 6

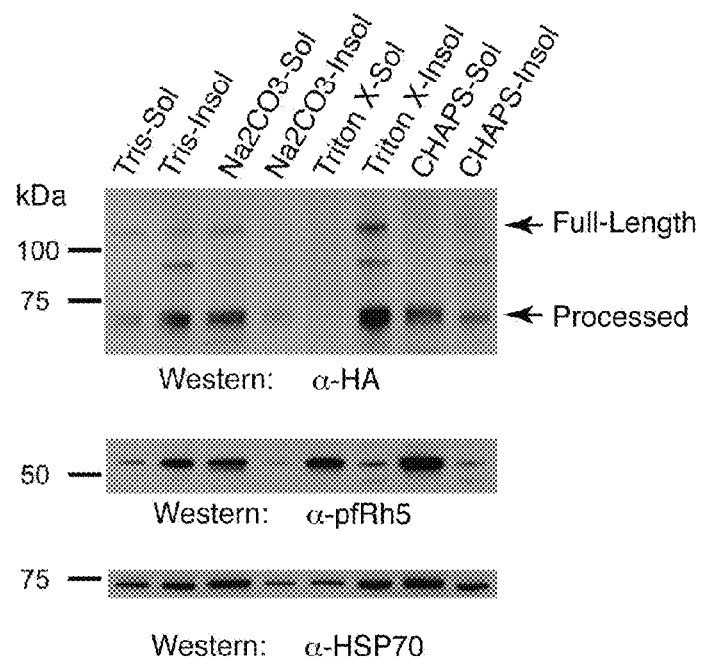
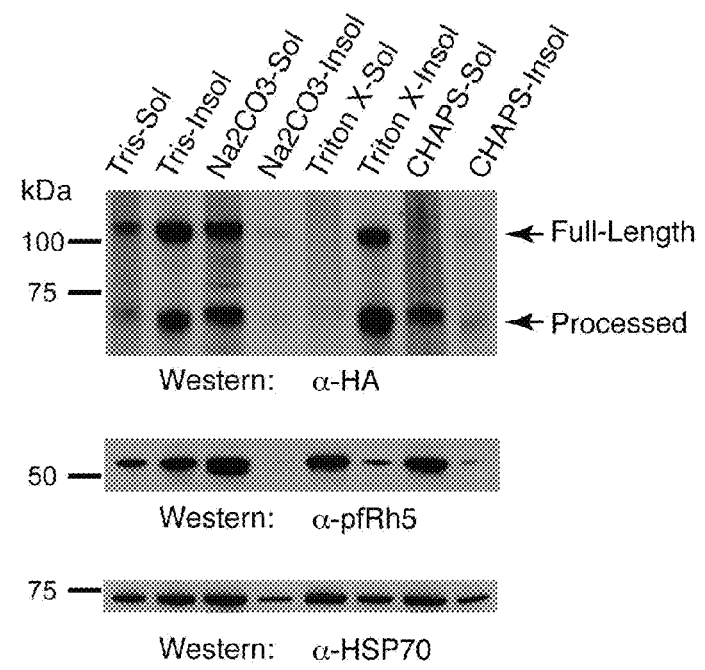
Figure 7

8A 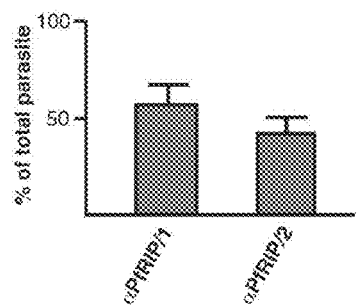
8B 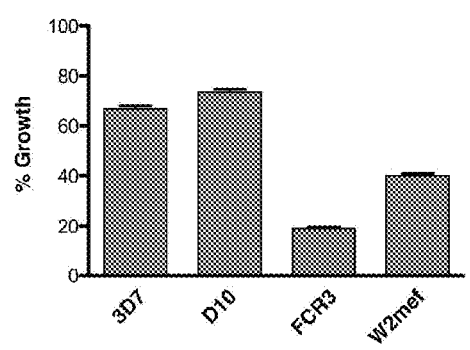
8C 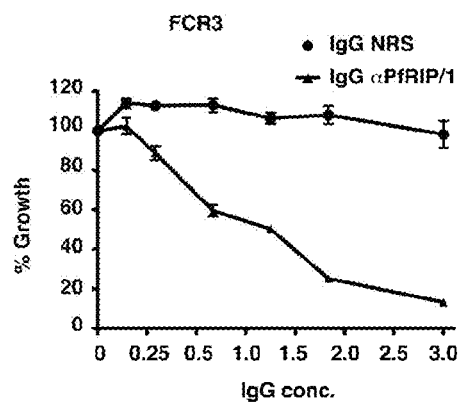
8D 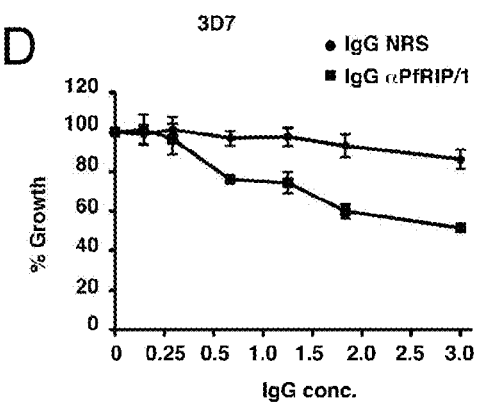
Figure 8

9A
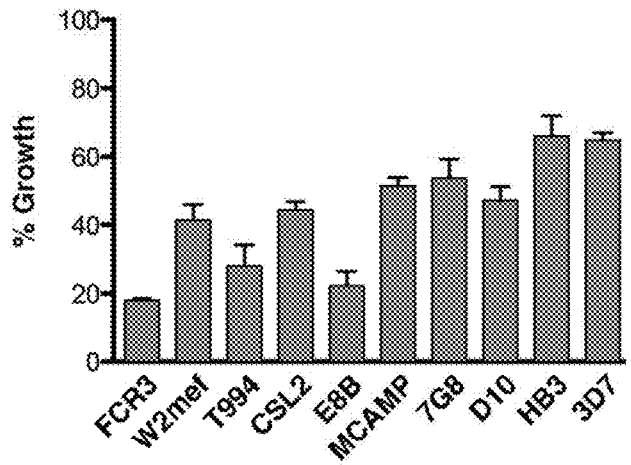
9B
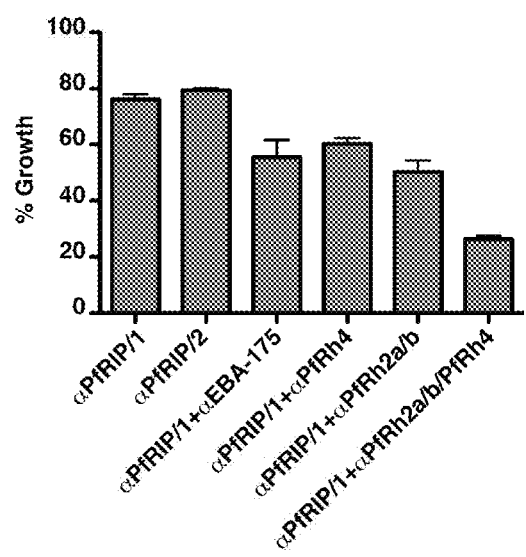
Figure 9

10A
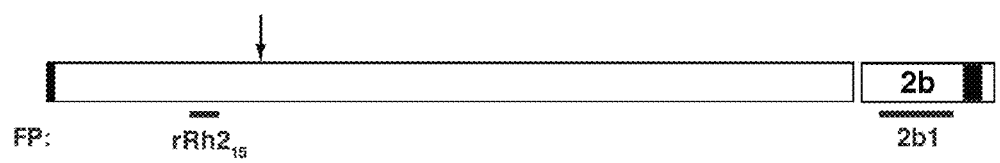
10B
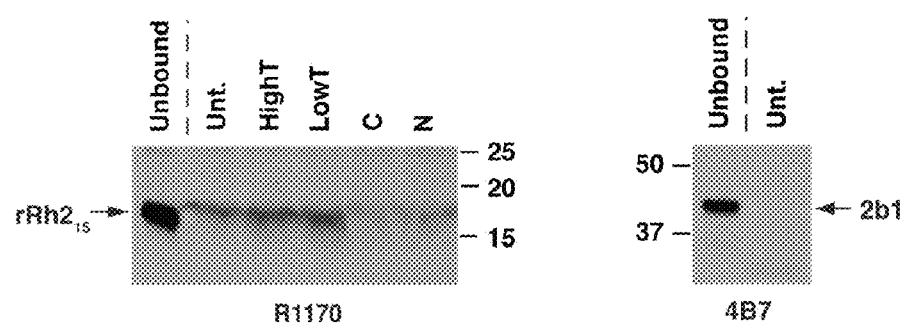
Figure 10

11A 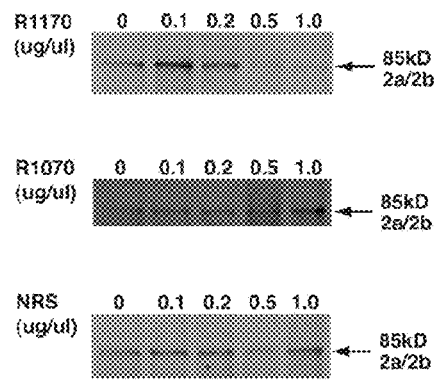
11B 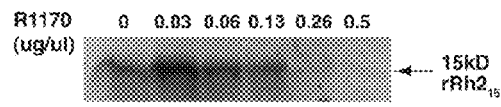
11C 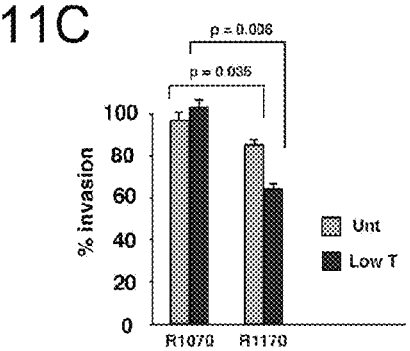
11D 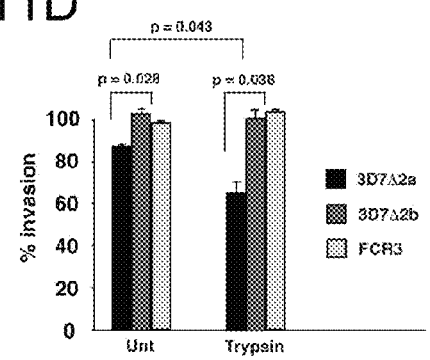
Figure 11

DNA sequence (Life Tech) of PfRip fragment (amino acids 604-1086 of SEQ ID NO:2)

```
        KpnI       NdeI
        GGTACCCATATGAAAAGCTATTGCAATGATCTGAGCGAATGCGATATTGGCCTGATTTAT
  1     ----------+---------+---------+---------+---------+---------+
        CCATGGGTATACTTTTCGATAACGTTACTAGACTCGCTTACGCTATAACCGGACTAAATA
                   K  S  Y  C  N  D  L  S  E  C  D  I  G  L  I  Y
                              BclI
        CATTTCGATACCTATTGCATCAATGATCAGTACCTGTTTGTGAGCTATAGCTGTAGCAAT
 61     ----------+---------+---------+---------+---------+---------+
        GTAAAGCTATGGATAACGTAGTTACTAGTCATGGACAAACACTCGATATCGACATCGTTA
         H  F  D  T  Y  C  I  N  D  Q  Y  L  F  V  S  Y  S  C  S  N

CTGTGCAATAAATGCCATAATAATAGCACCTGTTATGGCAATCGCTTTAATTATGATTGC
121     ----------+---------+---------+---------+---------+---------+
        GACACGTTATTTACGGTATTATTATCGTGGACAATACCGTTAGCGAAATTAATACTAACG
         L  C  N  K  C  H  N  N  S  T  C  Y  G  N  R  F  N  Y  D  C

TTTTGCGATAATCCGTATATTAGCAAATATGGCAATAAACTGTGCGAACGTCCGAATGAT
181     ----------+---------+---------+---------+---------+---------
        +
        AAAACGCTATTAGGCATATAATCGTTTATACCGTTATTTGACACGCTTGCAGGCTTACT
         A  F  C  D  N  P  Y  I  S  K  Y  G  N  K  L  C  E  R  P  N
         D

TGTGAAAGCGTTCTGTGTAGCCAGAATCAGGTTTGTCAGATTCTGCCGAATGATAAACTG
241     ----------+---------+---------+---------+---------+---------+
        ACACTTTCGCAAGACACATCGGTCTTAGTCCAAACAGTCTAAGACGGCTTACTATTTGAC
         C  E  S  V  L  C  S  Q  N  Q  V  C  Q  I  L  P  N  D  K  L

ATTTGTCAGTGCGAAGAAGGCTATAAAAACGTTAAAGGTAAATGCGTGCCGGATAATAAA
301     ----------+---------+---------+---------+---------+---------+
        TAAACAGTCACGCTTCTTCCGATATTTTGCAATTTCCATTTACGCACGGCCTATTATTT
         I  C  Q  C  E  E  G  Y  K  N  V  K  G  K  C  V  P  D  N  K

TGTGATCTGAGCTGTCCGAGCAATAAAGTTTGCGTTATTGAAAATGGCAAACAGACCTGT
361     ----------+---------+---------+---------+---------+---------+
        ACACTAGACTCGACAGGCTCGTTATTTCAAACGCAATAACTTTTACCGTTTGTCTGGACA
         C  D  L  S  C  P  S  N  K  V  C  V  I  E  N  G  K  Q  T  C

AAATGCAGCGAACGTTTTGTTCTGGAAAATGGTGTTTGCATTTGCGCCAATGATTATAAA
421     ----------+---------+---------+---------+---------+---------+
        TTTACGTCGCTTGCAAAACAAGACCTTTTACCACAAACGTAAACGCGGTTACTAATATTT
         K  C  S  E  R  F  V  L  E  N  G  V  C  I  C  A  N  D  Y  K

ATGGAAGATGGCATCAATTGCATTGCCAAAAATAAATGCAAACGCAAAGAGTATGAAAAT
481     ----------+---------+---------+---------+---------+---------+
        TACCTTCTACCGTAGTTAACGTAACGGTTTTTATTTACGTTTGCGTTTCTCATACTTTTA
         M  E  D  G  I  N  C  I  A  K  N  K  C  K  R  K  E  Y  E  N
```

Figure 13

```
     ATTTGCACCAATCCGAATGAAATGTGCGCCTATAATGAAGAAACCGATATTGTGAAATGC
541  ------------+---------+---------+---------+---------+---------+
     TAAACGTGGTTAGGCTTACTTTACACGCGGATATTACTTCTTTGGCTATAACACTTTACG
     I  C  T  N  P  N  E  M  C  A  Y  N  E  E  T  D  I  V  K  C

GAATGCAAAGAACATTATTATCGTAGCAGCCGTGGTGAATGCATTCTGAATGATTATTGC
601  ------------+---------+---------+---------+---------+---------+
     CTTACGTTTCTTGTAATAATAGCATCGTCGGCACCACTTACGTAAGACTTACTAATAACG
     E  C  K  E  H  Y  Y  R  S  S  R  G  E  C  I  L  N  D  Y  C

AAAGACATCAATTGCAAAGAAAATGAAGAATGCAGCATTGTGAATTTTAAACCGGAATGC
661  ------------+---------+---------+---------+---------+---------+
     TTTCTGTAGTTAACGTTTCTTTTACTTCTTACGTCGTAACACTTAAAATTTGGCCTTACG
     K  D  I  N  C  K  E  N  E  E  C  S  I  V  N  F  K  P  E  C

GTGTGCAAAGAAAATCTGAAAAAAAATAACAAAGGCGAGTGCATTTATGAAAATTCATGC
721  ------------+---------+---------+---------+---------+---------+
     CACACGTTTCTTTTAGACTTTTTTTTATTGTTTCCGCTCACGTAAATACTTTTAAGTACG
     V  C  K  E  N  L  K  K  N  N  K  G  E  C  I  Y  E  N  S  C

CTGATTAATGAAGGCAATTGCCCGAAAGATAGCAAATGCATTTATCGCGAATATAAACCG
781  ------------+---------+---------+---------+---------+---------+
     GACTAATTACTTCCGTTAACGGGCTTTCTATCGTTTACGTAAATAGCGCTTATATTTGGC
     L  I  N  E  G  N  C  P  K  D  S  K  C  I  Y  R  E  Y  K  P

CATGAATGCGTTTGCAATAAACAGGGTCATGTTGCCGTTAATGGTAAATGTGTGCTGGAA
841  ------------+---------+---------+---------+---------+---------+
     GTACTTACGCAAACGTTATTTGTCCCAGTACAACGGCAATTACCATTTACACACGACCTT
     H  E  C  V  C  N  K  Q  G  H  V  A  V  N  G  K  C  V  L  E

GATAAATGCGTGCATAATAAAAAATGTAGCGAAAATTCCATTTGCGTGAATGTGATGAAT
901  ------------+---------+---------+---------+---------+---------+
     CTATTTACGCACGTATTATTTTTTACATCGCTTTTAAGGTAAACGCACTTACACTACTTA
     D  K  C  V  H  N  K  K  C  S  E  N  S  I  C  V  N  V  M  N

AAAGAACCGATTTGCGTGTGCACCTATAATTATTATAAAAAAGATGGCGTGTGCCTGATT
961  ------------+---------+---------+---------+---------+---------
     TTTCTTGGCTAAACGCACACGTGGATATTAATAATATTTTTTCTACCGCACACGGACT
  +
     AA
     K  E  P  I  C  V  C  T  Y  N  Y  Y  K  K  D  G  V  C  L  I

CAGAATCCGTGTCTGAAAGATAATGGTGGTTGTAGCCGTAATAGCGAATGCACCTTTAAA
1021 ------------+---------+---------+---------+---------+---------+
     GTCTTAGGCACAGACTTTCTATTACCACCAACATCGGCATTATCGCTTACGTGGAAATTT
     Q  N  P  C  L  K  D  N  G  G  C  S  R  N  S  E  C  T  F  K

TATTCCAAAATTAATTGTACCTGTAAAGAGAACTACAAAAACAAAGATGATAGCTGCGTG
1081 ------------+---------+---------+---------+---------+---------+
     ATAAGGTTTTAATTAACATGGACATTTCTCTTGATGTTTTTGTTTCTACTATCGACGCAC
     Y  S  K  I  N  C  T  C  K  E  N  Y  K  N  K  D  D  S  C  V
```

Figure 13 cont.

```
                        HindIII
       CCGAATACCAATGAATATGATGAAAGCTTTACCTTTCAGTATAATGATGATGCCAGCATT
1141   ---------+---------+---------+---------+---------+---------+
       GGCTTATGGTTACTTATACTACTTTCGAAATGGAAAGTCATATTACTACTACGGTCGTAA
        P  N  T  N  E  Y  D  E  S  F  T  F  Q  Y  N  D  D  A  S  I ATTCTGGGTGCATGTGGTATGATTGAATTTAGCTATATCTACAACCAGATTATCTGGAAA
1201   ---------+---------+---------+---------+---------+---------+
       TAAGACCCACGTACACCATACTAACTTAAATCGATATAGATGTTGGTCTAATAGACCTTT
        I  L  G  A  C  G  M  I  E  F  S  Y  I  Y  N  Q  I  I  W  K ATTAATAATAGCAAAGAGAGCTACGTTTTCTATTATGATTATCCGACCGCAGGCAATATT
1261   ---------+---------+---------+---------+---------+----------
       TAATTATTATCGTTTCTCTCGATGCAAAAGATAATACTAATAGGCTGGCGTCCGTTATA
        A  I  N  N  S  K  E  S  Y  V  F  Y  Y  D  Y  P  T  A  G  N  I GAAGTGCAGATTAAAAACGAAATTTTCCACACCATTATCTACCTGAAAAAAAAAATTGGC
1321   ---------+---------+---------+---------+---------+---------+
       CTTCACGTCTAATTTTTGCTTTAAAAGGTGTGGTAATAGATGGACTTTTTTTTTTAACCG
        E  V  Q  I  K  N  E  I  F  H  T  I  I  Y  L  K  K  K  I  G AATAGCGTGATTTATGATGATTTTCAGGTGGATCATCAGACCTGTATTTATGAAAATGTG
1381   ---------+---------+---------+---------+---------+---------+
       TTATCGCACTAAATACTACTAAAAGTCCACCTAGTAGTCTGGACATAAATACTTTTACAC
        N  S  V  I  Y  D  D  F  Q  V  D  H  Q  T  C  I  Y  E  N  V BamHI    XhoI    SacI
       TTCTATTACAGCAATCAGAATTAAGGATCCCTCGAGGAGCTC
1441   ---------+---------+---------+---------+--
       AAGATAATGTCGTTAGTCTTAATTCCTAGGGAGCTCCTCGAG
        F  Y  Y  S  N  Q  N  *
```

Figure 13 cont.

Sequence of EBA175 fragment consisting of amino acids 761-1298 of SEQ ID NO:35)

QEAVPEESTEIAHRTETRTDERKNQEPANKDLKNPQQSVGENGTKDLLQE
DLGGSRSEDEVTQEFGVNHGIPKGEDQTLGKSDAIPNIGEPETGISTTEE
SRHEEGHNKQALSTSVDEPELSDTLQLHEDTKENDKLPLESSTITSPTES
GSSDTEETPSISEGPKGNEQKKRDDDSLSKISVSPENSRPETDAKDTSNL
LKLKGDVDISMPKAVIGSSPNDNINVTEQGDNISGVNSKPLSDDVRPDKN
HEEVKEHTSNSDNVQQSGGIVNMNVEKELKDTLENPSSSLDEGKAHEELS
EPNLSSDQDMSNTPGPLDNTSEETTERISNNEYKVNEREGERTLTKEYED
IVLKSHMNRESDDGELYDENSDLSTVNDESEDAEAKMKGNDTSEMSHNSS
QHIESDQQKNDMKTVGDLGTTHVQNEISVPVTGEIDEKLRESKESKIHKA
EEERLSHTDIHKINPEDRNSNTLHLKDIRNEENERHLTNQNINISQERDL
QKHGFHTMNNLHGDGVSERSQINHSHHGNRQDRGGNSG

Figure 14

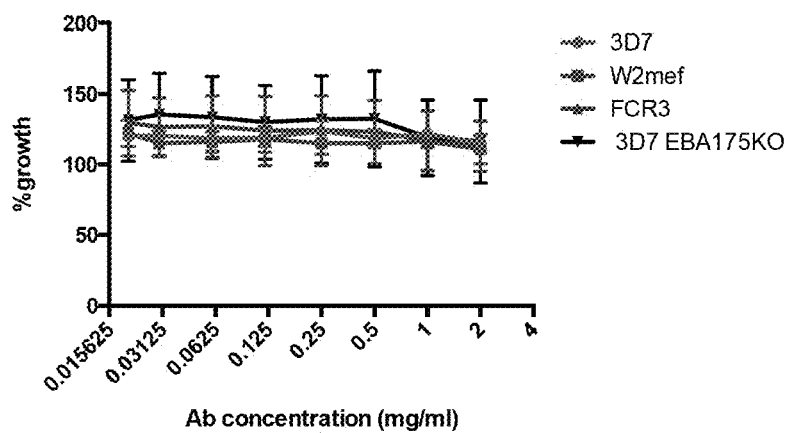

Figure 15

SEQUENCE LISTING

<160> NUMBER OF SEQ ID NOS: 64

<210> SEQ ID NO 1
<211> LENGTH: 3261
<212> TYPE: DNA
<213> ORGANISM: Plasmodium falciparum

<400> SEQUENCE: 1

```
atgttcagaa ttttttttac ccttcttata ataatattaa tcaagaaaac atcggcaatt      60
gatttaatag aaggaatttt ttatgaaaaa aatgaaatag ataaattaac attttctctc     120
gatcatagag ttagagataa tttaaaaaca gatttgattt taaataataa tggggaaaat     180
gattatgctt atttaaacaa atacgtttat actatattaa atcgtgattc aacagaaaaa     240
attaaaacat tttttctca taataaagac atgaaatcat gtgattattt tatatcaaaa     300
gaatataatt caagtgataa aacaaatcaa atatgttata aaaaaacatt ttgcggagta     360
gtaataccaa atagtgaaga aataaaaaca aataaaataa caaatgacaa actttattgt     420
gcacatttca attctacaca tataatcatt tattacatat cacaaccact tttattagaa     480
cctcatgttg tttatgaaga aacattttt gaaaaggaa aaaatgatca aattaattgc     540
caaggtatgt atatatctct aagatctgta catgtacata cacacaatgc tatattacaa     600
caagaaacac ttacatatat taaaaattta tgtgacggaa aaaacaattg taaattcgat     660
tttgattcaa taaaatatga aaataaatca cttactcatt atttgttttt tattaatata     720
caatatcaat gcataagtcc tctgaatcta caggaaaatg aaatgtgtga cgtatataat     780
gatgatacac ataaagcaac atgcaaatat ggttttaata aaatagaatt attaaaaaat     840
gtttgtgaag aaaattatag atgtacacaa gatatatgtt cagtaaatca attttgtgac     900
ggagaaaatg aaacatgtac atgcaaaaca tcattattac catcagctaa aaacaattgt     960
gaatacaacg atttatgtac agtttttaaat tgtcctgaaa attccacatg tgaacaaata    1020
ggaaatggga aaaaagctga atgtaaatgt gaaatggta aatattatca caataataaa    1080
tgttatacaa aaaatgattt agaattagcc ataaaaatag aaccacataa aaaagaaaaa    1140
ttttataaaa ataatttata tcaaggaaaa gcattaaaac cagaatatat tttttatgcaa    1200 tgtgaaaatg ggttctctat agaagttatt aatgcatatg tatcatgtta tagagtttca    1260
ttcaatctaa acaaattgaa atatgttaca gaatcattaa aaaaaatgtg tgatgggaaa    1320
accaaatgtg cttatggaaa tacaatagat ccaatagatg atttaaatca tcataatata    1380
tgtaataatt ttaatacaat atttaaatat gattatttat gtgtattcaa taatcaaaat    1440
```

-continued

```
attacttcag ataagaattc acatcttcat tctaatatac catcattata taattcaagt    1500
attctaccag atattaataa atctaaattc catttgattt caagaaatag tcgaaccaac    1560
caatatcctc ataacaatat atccatgcta gaaatacaaa atgaaatatc ctcacacaat    1620
tcaaatcagt ttagtacaga tccacacaca aatagtaata atataaacaa tatgaatatt    1680
aaaaaggtag aaatcttcag aagtcgtttt tcaagtaaat tacaatgtca aggggaaaa     1740 ataaatattg ataaagcaat tttaaaaggt ggggaaggat gtaatgattt gcttttgacg    1800
aattctttaa aatcatattg taatgattta tcagaatgtg atattggttt aatataccat    1860
tttgatactt attgtattaa tgatcaatat cttttgtat cttacagctg ctccaattta     1920
tgtaataaat gtcataacaa ttctacatgc tatgggaaca gatttaatta tgattgtttt    1980
tgtgataatc cttatatttc aaaatatgga ataaaattat gtgaacgtcc aaatgattgt    2040
gaatctgttt tgtgttcaca aaatcaagtt tgtcaaattc ttccaaatga taaattaata    2100
tgtcaatgtg aagaaggata taaaaatgtt aaaggtaaat gtgttccaga caacaaatgt    2160
gatctttcat gcccatcaaa caaagtttgt gttatcgaaa atggaaaaca aacatgtaaa    2220
tgttcagaac gttttgttct agagaatggt gtgtgtatat gtgctaatga ttataaaatg    2280
gaagatggta ttaattgtat agccaaaaat aaatgtaaaa gaaaagaata tgaaaatatt    2340
tgtacaaatc caaatgaaat gtgtgcttat aatgaagaaa cagatattgt aaaatgtgaa    2400
tgtaaagaac attattatag atcatcaaga ggtgaatgta tattaaatga ttattgtaaa    2460
gatattaatt gtaaagaaaa tgaagaatgt tctattgtaa actttaaacc agaatgtgta    2520
tgtaaagaaa atcttaaaaa aaataataaa ggagaatgta tttatgaaaa ctcctgttta    2580
attaatgaag ggaattgtcc aaaagattca aaatgtattt atagagaata taaaccacat    2640
gaatgtgtat gtaataaaca aggtcatgta gctgtcaatg gaaaatgtgt tttagaagat    2700
aaatgtgtac ataataaaaa atgttcgaaa aattctatat gtgtaaatgt aatgaataaa    2760
gaaccaatat gtgtatgtac atataattat tataaaaaag atggtgtatg tttaatacaa    2820
aacccttgtc taaagataa tggaggctgc tctagaaatt cagagtgtac atttaaatat     2880
agtaaaatta attgtacatg taaagaaaat tataaaaata aagatgattc ttgtgtacct    2940
aatacaaatg agtatgatga agttttaca ttccaatata atgacgatgc atctattatt     3000
cttggagcat gtggtatgat cgaattttca tatatatata accaaattat ttggaaaata    3060
aataactcaa aagaatctta cgtatttat tatgattatc caacagcagg taatatagaa     3120
gttcaaatta aaaatgaaat atttcacact attatatatt tgaaaaaaaa aataggcaat    3180
agtgttatct atgatgattt ccaagtagat catcaaacat gtatatatga aaatgtattt    3240
tattatagta atcagaatta g                                              3261
```

<210> SEQ ID NO 2
<211> LENGTH: 1086
<212> TYPE: PRT
<213> ORGANISM: Plasmodium falciparum

<400> SEQUENCE: 2

```
Met Phe Arg Ile Phe Phe Thr Leu Leu Ile Ile Leu Ile Lys Lys
1               5                   10                  15

Thr Ser Ala Ile Asp Leu Ile Glu Gly Ile Phe Tyr Glu Lys Asn Glu
            20                  25                  30

Ile Asp Lys Leu Thr Phe Ser Leu Asp His Arg Val Arg Asp Asn Leu
        35                  40                  45
```

-continued

```
Lys Thr Asp Leu Ile Leu Asn Asn Gly Glu Asn Asp Tyr Ala Tyr
    50                  55                  60
Leu Asn Lys Tyr Val Tyr Thr Ile Leu Asn Arg Asp Ser Thr Glu Lys
65                  70                  75                  80
Ile Lys Thr Phe Phe Ser His Asn Lys Asp Met Lys Ser Cys Asp Tyr
                    85                  90                  95
Phe Ile Ser Lys Glu Tyr Asn Ser Ser Asp Lys Thr Asn Gln Ile Cys
                100                 105                 110
Tyr Lys Lys Thr Phe Cys Gly Val Val Ile Pro Asn Ser Glu Glu Ile
            115                 120                 125
Lys Thr Asn Lys Ile Thr Asn Asp Lys Leu Tyr Cys Ala His Phe Asn
130                 135                 140
Ser Thr His Ile Ile Ile Tyr Tyr Ile Ser Gln Pro Leu Leu Leu Glu
145                 150                 155                 160
Pro His Val Val Tyr Glu Glu Thr Phe Phe Glu Lys Gly Lys Asn Asp
                    165                 170                 175
Gln Ile Asn Cys Gln Gly Met Tyr Ile Ser Leu Arg Ser Val His Val
                180                 185                 190
His Thr His Asn Ala Ile Leu Gln Gln Glu Thr Leu Thr Tyr Ile Lys
            195                 200                 205
Asn Leu Cys Asp Gly Lys Asn Asn Cys Lys Phe Asp Phe Asp Ser Ile
    210                 215                 220
Lys Tyr Glu Asn Lys Ser Leu Thr His Tyr Leu Phe Phe Ile Asn Ile
225                 230                 235                 240
Gln Tyr Gln Cys Ile Ser Pro Leu Asn Leu Gln Glu Asn Glu Met Cys
                    245                 250                 255
Asp Val Tyr Asn Asp Asp Thr His Lys Ala Thr Cys Lys Tyr Gly Phe
                260                 265                 270
Asn Lys Ile Glu Leu Leu Lys Asn Val Cys Glu Glu Asn Tyr Arg Cys
            275                 280                 285
Thr Gln Asp Ile Cys Ser Val Asn Gln Phe Cys Asp Gly Glu Asn Glu
    290                 295                 300
Thr Cys Thr Cys Lys Thr Ser Leu Leu Pro Ser Ala Lys Asn Asn Cys
305                 310                 315                 320
Glu Tyr Asn Asp Leu Cys Thr Val Leu Asn Cys Pro Glu Asn Ser Thr
                    325                 330                 335
Cys Glu Gln Ile Gly Asn Gly Lys Lys Ala Glu Cys Lys Cys Glu Asn
                340                 345                 350
Gly Lys Tyr Tyr His Asn Asn Lys Cys Tyr Thr Lys Asn Asp Leu Glu
            355                 360                 365
Leu Ala Ile Lys Ile Glu Pro His Lys Glu Lys Phe Tyr Lys Asn
    370                 375                 380
Asn Leu Tyr Gln Gly Lys Ala Leu Lys Pro Glu Tyr Ile Phe Met Gln
385                 390                 395                 400
Cys Glu Asn Gly Phe Ser Ile Glu Val Ile Asn Ala Tyr Val Ser Cys
                    405                 410                 415
Tyr Arg Val Ser Phe Asn Leu Asn Lys Leu Lys Tyr Val Thr Glu Ser
                420                 425                 430
Leu Lys Lys Met Cys Asp Gly Lys Thr Lys Cys Ala Tyr Gly Asn Thr
            435                 440                 445
Ile Asp Pro Ile Asp Asp Leu Asn His His Asn Ile Cys Asn Asn Phe
    450                 455                 460
```

-continued

```
Asn Thr Ile Phe Lys Tyr Asp Tyr Leu Cys Val Phe Asn Asn Gln Asn
465                 470                 475                 480

Ile Thr Ser Asp Lys Asn Ser His Leu His Ser Asn Ile Pro Ser Leu
            485                 490                 495

Tyr Asn Ser Ser Ile Leu Pro Asp Ile Asn Lys Ser Lys Phe His Leu
                500                 505                 510

Ile Ser Arg Asn Ser Arg Thr Asn Gln Tyr Pro His Asn Asn Ile Ser
        515                 520                 525

Met Leu Glu Ile Gln Asn Glu Ile Ser Ser His Ser Asn Ser Gln Phe
530                 535                 540

Ser Thr Asp Pro His Thr Asn Ser Asn Asn Ile Asn Asn Met Asn Ile
545                 550                 555                 560

Lys Lys Val Glu Ile Phe Arg Ser Arg Phe Ser Ser Lys Leu Gln Cys
                565                 570                 575

Gln Gly Gly Lys Ile Asn Ile Asp Lys Ala Ile Leu Lys Gly Gly Glu
            580                 585                 590

Gly Cys Asn Asp Leu Leu Leu Thr Asn Ser Leu Lys Ser Tyr Cys Asn
        595                 600                 605

Asp Leu Ser Glu Cys Asp Ile Gly Leu Ile Tyr His Phe Asp Thr Tyr
    610                 615                 620

Cys Ile Asn Asp Gln Tyr Leu Phe Val Ser Tyr Ser Cys Ser Asn Leu
625                 630                 635                 640

Cys Asn Lys Cys His Asn Asn Ser Thr Cys Tyr Gly Asn Arg Phe Asn
                645                 650                 655

Tyr Asp Cys Phe Cys Asp Asn Pro Tyr Ile Ser Lys Tyr Gly Asn Lys
            660                 665                 670

Leu Cys Glu Arg Pro Asn Asp Cys Glu Ser Val Leu Cys Ser Gln Asn
        675                 680                 685

Gln Val Cys Gln Ile Leu Pro Asn Asp Lys Leu Ile Cys Gln Cys Glu
    690                 695                 700

Glu Gly Tyr Lys Asn Val Lys Gly Lys Cys Val Pro Asp Asn Lys Cys
705                 710                 715                 720

Asp Leu Ser Cys Pro Ser Asn Lys Val Cys Val Ile Glu Asn Gly Lys
                725                 730                 735

Gln Thr Cys Lys Cys Ser Glu Arg Phe Val Leu Glu Asn Gly Val Cys
            740                 745                 750

Ile Cys Ala Asn Asp Tyr Lys Met Glu Asp Gly Ile Asn Cys Ile Ala
        755                 760                 765

Lys Asn Lys Cys Lys Arg Lys Glu Tyr Glu Asn Ile Cys Thr Asn Pro
770                 775                 780

Asn Glu Met Cys Ala Tyr Asn Glu Glu Thr Asp Ile Val Lys Cys Glu
785                 790                 795                 800

Cys Lys Glu His Tyr Tyr Arg Ser Ser Arg Gly Glu Cys Ile Leu Asn
                805                 810                 815

Asp Tyr Cys Lys Asp Ile Asn Cys Lys Glu Asn Glu Glu Cys Ser Ile
            820                 825                 830

Val Asn Phe Lys Pro Glu Cys Val Cys Lys Glu Asn Leu Lys Lys Asn
        835                 840                 845

Asn Lys Gly Glu Cys Ile Tyr Glu Asn Ser Cys Leu Ile Asn Glu Gly
    850                 855                 860

Asn Cys Pro Lys Asp Ser Lys Cys Ile Tyr Arg Glu Tyr Lys Pro His
865                 870                 875                 880

Glu Cys Val Cys Asn Lys Gln Gly His Val Ala Val Asn Gly Lys Cys
```

```
                885                 890                 895
Val Leu Glu Asp Lys Cys Val His Asn Lys Cys Ser Glu Asn Ser
            900                 905                 910
Ile Cys Val Asn Val Met Asn Lys Glu Pro Ile Cys Val Cys Thr Tyr
            915                 920                 925
Asn Tyr Tyr Lys Lys Asp Gly Val Cys Leu Ile Gln Asn Pro Cys Leu
        930                 935                 940
Lys Asp Asn Gly Gly Cys Ser Arg Asn Ser Glu Cys Thr Phe Lys Tyr
945                 950                 955                 960
Ser Lys Ile Asn Cys Thr Cys Lys Glu Asn Tyr Lys Asn Lys Asp Asp
                965                 970                 975
Ser Cys Val Pro Asn Thr Asn Glu Tyr Asp Glu Ser Phe Thr Phe Gln
            980                 985                 990
Tyr Asn Asp Asp Ala Ser Ile Ile Leu Gly Ala Cys Gly Met Ile Glu
            995                 1000                1005
Phe Ser Tyr Ile Tyr Asn Gln Ile Ile Trp Lys Ile Asn Asn Ser
        1010                1015                1020
Lys Glu Ser Tyr Val Phe Tyr Tyr Asp Tyr Pro Thr Ala Gly Asn
        1025                1030                1035
Ile Glu Val Gln Ile Lys Asn Glu Ile Phe His Thr Ile Ile Tyr
        1040                1045                1050
Leu Lys Lys Lys Ile Gly Asn Ser Val Ile Tyr Asp Asp Phe Gln
        1055                1060                1065
Val Asp His Gln Thr Cys Ile Tyr Glu Asn Val Phe Tyr Tyr Ser
        1070                1075                1080
Asn Gln Asn
        1085

<210> SEQ ID NO 3
<211> LENGTH: 110
<212> TYPE: PRT
<213> ORGANISM: Artificial Sequence
<220> FEATURE:
<223> OTHER INFORMATION: pfRIP antigenic fragment

<400> SEQUENCE: 3

Asn Glu Glu Thr Asp Ile Val Lys Cys Glu Cys Lys Glu His Tyr Tyr
1               5                   10                  15
Arg Ser Ser Arg Gly Glu Cys Ile Leu Asn Asp Tyr Cys Lys Asp Ile
            20                  25                  30
Asn Cys Lys Glu Asn Glu Cys Ser Ile Val Asn Phe Lys Pro Glu
        35                  40                  45
Cys Val Cys Lys Glu Asn Leu Lys Lys Asn Asn Lys Gly Glu Cys Ile
    50                  55                  60
Tyr Glu Asn Ser Cys Leu Ile Asn Glu Gly Asn Cys Pro Lys Asp Ser
65                  70                  75                  80
Lys Cys Ile Tyr Arg Glu Tyr Leu Pro His Glu Cys Val Cys Asn Lys
                85                  90                  95
Gln Gly His Val Ala Val Asn Gly Lys Cys Val Leu Glu Asp
            100                 105                 110

<210> SEQ ID NO 4
<211> LENGTH: 131
<212> TYPE: PRT
<213> ORGANISM: Artificial Sequence
<220> FEATURE:
<223> OTHER INFORMATION: pfRIP antigenic fragment
```

<400> SEQUENCE: 4

Ile Asn Ile Gln Tyr Gln Cys Ile Ser Pro Leu Asn Leu Gln Glu Asn
1               5                   10                  15

Glu Met Cys Asp Val Tyr Asn Asp Thr His Lys Ala Thr Cys Lys
            20                  25                  30

Tyr Gly Phe Asn Lys Ile Glu Leu Leu Lys Asn Val Cys Glu Glu Asn
        35                  40                  45

Tyr Arg Cys Thr Gln Asp Ile Cys Ser Val Asn Gln Phe Cys Asp Gly
    50                  55                  60

Glu Asn Glu Thr Cys Thr Cys Lys Thr Ser Leu Leu Pro Ser Ala Lys
65                  70                  75                  80

Asn Asn Cys Glu Tyr Asn Asp Leu Cys Thr Val Leu Asn Cys Pro Glu
                85                  90                  95

Asn Ser Thr Cys Glu Gln Ile Gly Asn Gly Lys Lys Ala Glu Cys Lys
            100                 105                 110

Cys Glu Asn Gly Lys Tyr Tyr His Asn Asn Lys Cys Tyr Thr Lys Asn
            115                 120                 125

Asp Leu Glu
        130

<210> SEQ ID NO 5
<211> LENGTH: 10
<212> TYPE: PRT
<213> ORGANISM: Artificial Sequence
<220> FEATURE:
<223> OTHER INFORMATION: Tryptic peptide

<400> SEQUENCE: 5

Lys Ser Cys Asp Tyr Phe Ile Ser Lys Glu
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Tryptic peptide

<400> SEQUENCE: 6

Lys Glu Tyr Asn Ser Ser Asp Lys Thr Asn Gln Ile Cys Tyr Lys Lys
1               5                   10                  15

<210> SEQ ID NO 7
<211> LENGTH: 12
<212> TYPE: PRT
<213> ORGANISM: Artificial Sequence
<220> FEATURE:
<223> OTHER INFORMATION: Tryptic peptide

<400> SEQUENCE: 7

Lys Leu Ile Cys Gln Cys Glu Glu Gly Tyr Lys Asn
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Tryptic peptide

<400> SEQUENCE: 8

Lys Met Glu Asp Gly Ile Asn Cys Ile Ala Lys Asn
1               5                  10

<210> SEQ ID NO 9
<211> LENGTH: 12
<212> TYPE: PRT
<213> ORGANISM: Artificial Sequence
<220> FEATURE:
<223> OTHER INFORMATION: Tryptic peptide

<400> SEQUENCE: 9

Lys Ile Asn Cys Thr Cys Lys Glu Asn Tyr Lys Asn
1               5                  10

<210> SEQ ID NO 10
<211> LENGTH: 2971
<212> TYPE: PRT
<213> ORGANISM: Plasmodium falciparum

<400> SEQUENCE: 10

Met Gln Arg Trp Ile Phe Cys Asn Ile Val Leu His Ile Leu Ile Tyr
1               5                   10                  15

Leu Ala Glu Phe Ser His Glu Gln Ser Tyr Ser Ser Asn Glu Lys
            20                  25                  30

Ile Arg Lys Asp Tyr Ser Asp Asp Asn Asn Tyr Glu Pro Thr Phe Ser
        35                  40                  45

Tyr Glu Lys Arg Lys Lys Glu Tyr Gly Lys Asp Glu Ser Tyr Ile Lys
    50                  55                  60

Asn Tyr Arg Gly Asn Asn Phe Ser Tyr Asp Leu Ser Lys Asn Ser Ser
65                  70                  75                  80

Ile Phe Leu His Met Gly Asn Gly Ser Asn Ser Lys Thr Leu Lys Arg
                85                  90                  95

Cys Asn Lys Lys Lys Asn Ile Lys Thr Asn Phe Leu Arg Pro Ile Glu
            100                 105                 110

Glu Glu Lys Thr Val Leu Asn Asn Tyr Val Tyr Lys Gly Val Asn Phe
        115                 120                 125

Leu Asp Thr Ile Lys Arg Asn Asp Ser Ser Tyr Lys Phe Asp Val Tyr
    130                 135                 140

Lys Asp Thr Ser Phe Leu Lys Asn Arg Glu Tyr Lys Glu Leu Ile Thr
145                 150                 155                 160

Met Gln Tyr Asp Tyr Ala Tyr Leu Glu Ala Thr Lys Glu Val Leu Tyr
                165                 170                 175

Leu Ile Pro Lys Asp Lys Asp Tyr His Lys Phe Tyr Lys Asn Glu Leu
            180                 185                 190

Glu Lys Ile Leu Phe Asn Leu Lys Asp Ser Leu Lys Leu Leu Arg Glu
        195                 200                 205

Gly Tyr Ile Gln Ser Lys Leu Glu Met Ile Arg Ile His Ser Asp Ile
    210                 215                 220

Asp Ile Leu Asn Glu Phe His Gln Gly Asn Ile Ile Asn Asp Asn Tyr
225                 230                 235                 240

Phe Asn Asn Glu Ile Lys Lys Arg Lys Glu Asp Met Glu Lys Tyr Ile
                245                 250                 255

Arg Glu Tyr Asn Leu Tyr Ile Tyr Tyr Glu Asn Gln Leu Lys Ile
            260                 265                 270

Lys Ile Gln Lys Leu Thr Asn Glu Val Ser Ile Asn Leu Asn Lys Ser
        275                 280                 285

Thr Cys Glu Lys Asn Cys Tyr Asn Tyr Ile Leu Lys Leu Glu Lys Tyr

-continued

```
                290                 295                 300
Lys Asn Ile Ile Lys Asp Lys Ile Asn Lys Trp Lys Asp Leu Pro Glu
305                 310                 315                 320

Ile Tyr Ile Asp Asp Lys Ser Phe Ser Tyr Thr Phe Leu Lys Asp Val
                325                 330                 335

Ile Asn Asn Lys Ile Asp Ile Tyr Lys Thr Ile Ser Ser Phe Ile Ser
                340                 345                 350

Thr Gln Lys Gln Leu Tyr Tyr Phe Glu Tyr Ile Tyr Ile Met Asn Lys
                355                 360                 365

Asn Thr Leu Asn Leu Leu Ser Tyr Asn Ile Gln Lys Thr Asp Ile Asn
370                 375                 380

Ser Ser Ser Lys Tyr Thr Tyr Thr Lys Ser His Phe Leu Lys Asp Asn
385                 390                 395                 400

His Ile Leu Leu Ser Lys Tyr Tyr Thr Ala Lys Phe Ile Asp Ile Leu
                405                 410                 415

Asn Lys Ile Tyr Tyr Tyr Asn Leu Tyr Lys Asn Lys Ile Leu Leu Phe
                420                 425                 430

Asn Lys Tyr Ile Ile Lys Leu Arg Asn Asp Leu Lys Glu Tyr Ala Phe
                435                 440                 445

Lys Ser Ile Gln Phe Ile Gln Asp Lys Ile Lys Lys His Lys Asp Glu
450                 455                 460

Leu Ser Ile Glu Asn Ile Leu Gln Glu Val Asn Asn Ile Tyr Ile Lys
465                 470                 475                 480

Tyr Asp Thr Ser Ile Asn Glu Ile Ser Lys Tyr Asn Asn Leu Ile Ile
                485                 490                 495

Asn Thr Asp Leu Gln Ile Val Gln Gln Lys Leu Leu Glu Ile Lys Gln
                500                 505                 510

Lys Lys Asn Asp Ile Thr His Lys Val Gln Leu Ile Asn His Ile Tyr
                515                 520                 525

Lys Asn Ile His Asp Glu Ile Leu Asn Lys Lys Asn Asn Glu Ile Thr
                530                 535                 540

Lys Ile Ile Ile Asn Asn Ile Lys Asp His Lys Lys Asp Leu Gln Asp
545                 550                 555                 560

Leu Leu Leu Phe Ile Gln Gln Ile Lys Gln Tyr Asn Ile Leu Thr Asp
                565                 570                 575

His Lys Ile Thr Gln Cys Asn Asn Tyr Tyr Lys Glu Ile Ile Lys Met
                580                 585                 590

Lys Glu Asp Ile Asn His Ile His Ile Tyr Ile Gln Pro Ile Leu Asn
                595                 600                 605

Asn Leu His Thr Leu Lys Gln Val Gln Asn Asn Lys Ile Lys Tyr Glu
                610                 615                 620

Glu His Ile Lys Gln Ile Leu Gln Lys Ile Tyr Asp Lys Lys Glu Ser
625                 630                 635                 640

Leu Lys Lys Ile Ile Leu Leu Lys Asp Glu Ala Gln Leu Asp Ile Thr
                645                 650                 655

Leu Leu Asp Asp Leu Ile Gln Lys Gln Thr Lys Lys Gln Thr Gln Thr
                660                 665                 670

Gln Thr Gln Thr Gln Lys Gln Thr Leu Ile Gln Asn Asn Glu Thr Ile
                675                 680                 685

Gln Leu Ile Ser Gly Gln Glu Asp Lys His Glu Ser Asn Pro Phe Asn
                690                 695                 700

His Ile Gln Thr Tyr Ile Gln Gln Lys Asp Thr Gln Asn Lys Asn Ile
705                 710                 715                 720
```

```
Gln Asn Leu Leu Lys Ser Leu Tyr Asn Gly Asn Ile Asn Thr Phe Ile
            725                 730                 735

Asp Thr Ile Ser Lys Tyr Ile Leu Lys Gln Lys Asp Ile Glu Leu Thr
        740                 745                 750

Gln His Val Tyr Thr Asp Glu Lys Ile Asn Asp Tyr Leu Glu Glu Ile
            755                 760                 765

Lys Asn Glu Gln Asn Lys Ile Asp Lys Thr Ile Asp Asp Ile Lys Ile
        770                 775                 780

Gln Glu Thr Leu Lys Gln Ile Thr His Ile Val Asn Asn Ile Lys Thr
785                 790                 795                 800

Ile Lys Lys Asp Leu Leu Lys Glu Phe Ile Gln His Leu Ile Lys Tyr
            805                 810                 815

Met Asn Glu Arg Tyr Gln Asn Met Gln Gln Gly Tyr Asn Asn Leu Thr
            820                 825                 830

Asn Tyr Ile Asn Gln Tyr Glu Glu Asn Asn Asn Met Lys Gln Tyr
        835                 840                 845

Ile Thr Thr Ile Arg Asn Ile Gln Lys Ile Tyr Tyr Asp Asn Ile Tyr
        850                 855                 860

Ala Lys Glu Lys Glu Ile Arg Ser Gly Gln Tyr Tyr Lys Asp Phe Ile
865                 870                 875                 880

Thr Ser Arg Lys Asn Ile Tyr Asn Ile Arg Glu Asn Ile Ser Lys Asn
            885                 890                 895

Val Asp Met Ile Lys Asn Glu Glu Lys Lys Ile Gln Asn Cys Val
        900                 905                 910

Asp Lys Tyr Asn Ser Ile Lys Gln Tyr Val Lys Met Leu Lys Asn Gly
            915                 920                 925

Asp Thr Gln Asp Glu Asn Asn Asn Asn Asn Asp Ile Tyr Asp Lys
        930                 935                 940

Leu Ile Val Pro Leu Asp Ser Ile Lys Gln Asn Ile Asp Lys Tyr Asn
945                 950                 955                 960

Thr Glu His Asn Phe Ile Thr Phe Thr Asn Lys Ile Asn Thr His Asn
            965                 970                 975

Lys Lys Asn Gln Glu Met Met Glu Glu Phe Ile Tyr Ala Tyr Lys Arg
            980                 985                 990

Leu Lys Ile Leu Lys Ile Leu Asn Ile Ser Leu Lys Ala Cys Glu Lys
            995                 1000                1005

Asn Asn Lys Ser Ile Asn Thr Leu Asn Asp Lys Thr Gln Glu Leu
        1010                1015                1020

Lys Lys Ile Val Thr His Glu Ile Asp Leu Leu Gln Lys Asp Ile
        1025                1030                1035

Leu Thr Ser Gln Ile Ser Asn Lys Asn Val Leu Leu Asn Asp
        1040                1045                1050

Leu Leu Lys Glu Ile Glu Gln Tyr Ile Ile Asp Val His Lys Leu
        1055                1060                1065

Lys Lys Lys Ser Asn Leu Leu Phe Thr Tyr Tyr Glu Gln Ser Lys
        1070                1075                1080

Asn Tyr Phe Tyr Phe Lys Asn Lys Lys Asp Asn Phe Asp Ile Gln
        1085                1090                1095

Lys Thr Ile Asn Lys Met Asn Glu Trp Leu Ala Ile Lys Asn Tyr
        1100                1105                1110

Ile Asn Glu Ile Asn Lys Asn Tyr Gln Thr Leu Tyr Glu Lys Lys
        1115                1120                1125
```

```
Ile Asn Val Leu Leu His Asn Ser Lys Ser Tyr Val Gln Tyr Phe
1130                1135                1140

Tyr Asp His Ile Ile Asn Leu Ile Leu Gln Lys Lys Asn Tyr Leu
1145                1150                1155

Glu Asn Thr Leu Lys Thr Lys Ile Gln Asp Asn Glu His Ser Leu
1160                1165                1170

Tyr Ala Leu Gln Gln Asn Glu Glu Tyr Gln Lys Val Lys Asn Glu
1175                1180                1185

Lys Asp Gln Asn Glu Ile Lys Lys Ile Lys Gln Leu Ile Glu Lys
1190                1195                1200

Asn Lys Asn Asp Ile Leu Thr Tyr Glu Asn Asn Ile Glu Gln Ile
1205                1210                1215

Glu Gln Lys Asn Ile Glu Leu Lys Thr Asn Ala Gln Asn Lys Asp
1220                1225                1230

Asp Gln Ile Val Asn Thr Leu Asn Glu Val Lys Lys Lys Ile Ile
1235                1240                1245

Tyr Thr Tyr Phe Lys Val Asp Asn Gln Ile Ser Asn Val Leu Lys
1250                1255                1260

Asn Tyr Glu Glu Gly Lys Val Glu Tyr Asp Lys Asn Val Val Gln
1265                1270                1275

Asn Val Asn Asp Ala Asp Asp Thr Asn Asp Ile Asp Glu Ile Asn
1280                1285                1290

Asp Ile Asp Glu Ile Asn Asp Ile Asp Glu Ile Asn Asp Ile Asp
1295                1300                1305

Glu Ile Asn Asp Ile Asp Glu Ile Lys Asp Ile Asp His Ile Lys
1310                1315                1320

His Phe Asp Asp Thr Lys His Phe Asp Asp Ile Tyr His Ala Asp
1325                1330                1335

Asp Thr Arg Asp Glu Tyr His Ile Ala Leu Ser Asn Tyr Ile Lys
1340                1345                1350

Thr Glu Leu Arg Asn Ile Asn Leu Gln Glu Ile Lys Asn Asn Ile
1355                1360                1365

Ile Lys Ile Phe Lys Glu Phe Lys Ser Ala His Lys Glu Ile Lys
1370                1375                1380

Lys Glu Ser Glu Gln Ile Asn Lys Glu Phe Thr Lys Met Asp Val
1385                1390                1395

Val Ile Asn Gln Leu Arg Asp Ile Asp Arg Gln Met Leu Asp Leu
1400                1405                1410

Tyr Lys Glu Leu Asp Glu Lys Tyr Ser Glu Phe Asn Lys Thr Lys
1415                1420                1425

Ile Glu Glu Ile Asn Asn Ile Arg Glu Asn Ile Asn Asn Val Glu
1430                1435                1440

Ile Trp Tyr Glu Lys Asn Ile Ile Glu Tyr Phe Leu Arg His Met
1445                1450                1455

Asn Asp Gln Lys Asp Lys Ala Ala Lys Tyr Met Glu Asn Ile Asp
1460                1465                1470

Thr Tyr Lys Asn Asn Ile Glu Ile Ile Ser Lys Gln Ile Asn Pro
1475                1480                1485

Glu Asn Tyr Val Glu Thr Leu Asn Lys Ser Asn Met Tyr Ser Tyr
1490                1495                1500

Val Glu Lys Ala Asn Asp Leu Phe Tyr Lys Gln Ile Asn Asn Ile
1505                1510                1515

Ile Ile Asn Ser Asn Gln Leu Lys Asn Glu Ala Phe Thr Ile Asp
```

```
                  1520               1525                1530

Glu Leu Gln Asn Ile Gln Lys Asn Arg Lys Asn Leu Leu Thr Lys
    1535                1540                1545

Lys Gln Gln Ile Ile Gln Tyr Thr Asn Glu Ile Glu Asn Ile Phe
    1550                1555                1560

Asn Glu Ile Lys Asn Ile Asn Asn Ile Leu Val Leu Thr Asn Tyr
    1565                1570                1575

Lys Ser Ile Leu Gln Asp Ile Ser Gln Asn Ile Asn His Val Ser
    1580                1585                1590

Ile Tyr Thr Glu Gln Leu His Asn Leu Tyr Ile Lys Leu Glu Glu
    1595                1600                1605

Glu Lys Glu Gln Met Lys Thr Leu Tyr His Lys Ser Asn Val Leu
    1610                1615                1620

His Asn Gln Ile Asn Phe Asn Glu Asp Ala Phe Ile Asn Asn Leu
    1625                1630                1635

Leu Ile Asn Thr Glu Lys Ile Lys Asn Asp Ile Thr His Ile Lys
    1640                1645                1650

Glu Lys Thr Asn Ile Tyr Met Ile Asp Val Asn Lys Ser Lys Asn
    1655                1660                1665

Asn Ala Gln Leu Tyr Phe His Asn Thr Leu Arg Gly Asn Glu Lys
    1670                1675                1680

Ile Glu Tyr Leu Lys Asn Leu Lys Asn Ser Thr Asn Gln Gln Ile
    1685                1690                1695

Thr Leu Gln Glu Leu Lys Gln Val Gln Glu Asn Val Glu Lys Val
    1700                1705                1710

Lys Asp Ile Tyr Asn Gln Thr Ile Lys Tyr Glu Glu Glu Ile Lys
    1715                1720                1725

Lys Asn Tyr His Ile Ile Thr Asp Tyr Glu Asn Lys Ile Asn Asp
    1730                1735                1740

Ile Leu His Asn Ser Phe Ile Lys Gln Ile Asn Met Glu Ser Ser
    1745                1750                1755

Asn Asn Lys Lys Gln Thr Lys Gln Ile Ile Asp Ile Ile Asn Asp
    1760                1765                1770

Lys Thr Phe Glu Glu His Ile Lys Thr Ser Lys Thr Lys Ile Asn
    1775                1780                1785

Met Leu Lys Glu Gln Ser Gln Met Lys His Ile Asp Lys Thr Leu
    1790                1795                1800

Leu Asn Glu Gln Ala Leu Lys Leu Phe Val Asp Ile Asn Ser Thr
    1805                1810                1815

Asn Asn Asn Leu Asp Asn Met Leu Ser Glu Ile Asn Ser Ile Gln
    1820                1825                1830

Asn Asn Ile His Thr Tyr Ile Gln Glu Ala Asn Lys Ser Phe Asp
    1835                1840                1845

Lys Phe Lys Ile Ile Cys Asp Gln Asn Val Asn Asp Leu Leu Asn
    1850                1855                1860

Lys Leu Ser Leu Gly Asp Leu Asn Tyr Met Asn His Leu Lys Asn
    1865                1870                1875

Leu Gln Asn Glu Ile Arg Asn Met Asn Leu Glu Lys Asn Phe Met
    1880                1885                1890

Leu Asp Lys Ser Lys Lys Ile Asp Glu Glu Glu Lys Lys Leu Asp
    1895                1900                1905

Ile Leu Lys Val Asn Ile Ser Asn Ile Asn Asn Ser Leu Asp Lys
    1910                1915                1920
```

-continued

```
Leu Lys Lys Tyr Tyr Glu Glu Ala Leu Phe Gln Lys Val Lys Glu
1925                1930                1935

Lys Ala Glu Ile Gln Lys Glu Asn Ile Glu Lys Ile Lys Gln Glu
1940                1945                1950

Ile Asn Thr Leu Ser Asp Val Phe Lys Lys Pro Phe Phe Phe Ile
1955                1960                1965

Gln Leu Asn Thr Asp Ser Ser Gln His Glu Lys Asp Ile Asn Asn
1970                1975                1980

Asn Val Glu Thr Tyr Lys Asn Ile Asp Glu Ile Tyr Asn Val
1985                1990                1995

Phe Ile Gln Ser Tyr Asn Leu Ile Gln Lys Tyr Ser Ser Glu Ile
2000                2005                2010

Phe Ser Ser Thr Leu Asn Tyr Ile Gln Thr Lys Glu Ile Lys Glu
2015                2020                2025

Lys Ser Ile Lys Glu Gln Asn Gln Leu Asn Gln Asn Glu Lys Glu
2030                2035                2040

Ala Ser Val Leu Leu Lys Asn Ile Lys Ile Asn Glu Thr Ile Lys
2045                2050                2055

Leu Phe Lys Gln Ile Lys Asn Glu Arg Gln Asn Asp Val His Asn
2060                2065                2070

Ile Lys Glu Asp Tyr Asn Leu Leu Gln Gln Tyr Leu Asn Tyr Met
2075                2080                2085

Lys Asn Glu Met Glu Gln Leu Lys Lys Tyr Lys Asn Asp Val His
2090                2095                2100

Met Asp Lys Asn Tyr Val Glu Asn Asn Asn Gly Glu Lys Glu Lys
2105                2110                2115

Leu Leu Lys Glu Thr Ile Ser Ser Tyr Tyr Asp Lys Ile Asn Asn
2120                2125                2130

Ile Asn Asn Lys Leu Tyr Ile Tyr Lys Asn Lys Glu Asp Thr Tyr
2135                2140                2145

Phe Asn Asn Met Ile Lys Val Ser Glu Ile Leu Asn Ile Ile Ile
2150                2155                2160

Lys Lys Lys Gln Gln Asn Glu Gln Arg Ile Val Ile Asn Ala Glu
2165                2170                2175

Tyr Asp Ser Ser Leu Ile Asn Lys Asp Glu Glu Ile Lys Lys Glu
2180                2185                2190

Ile Asn Asn Gln Ile Ile Glu Leu Asn Lys His Asn Glu Asn Ile
2195                2200                2205

Ser Asn Ile Phe Lys Asp Ile Gln Asn Ile Lys Lys Gln Ser Gln
2210                2215                2220

Asp Ile Ile Thr Asn Met Asn Asp Met Tyr Lys Ser Thr Ile Leu
2225                2230                2235

Leu Val Asp Ile Ile Gln Lys Lys Glu Glu Ala Leu Asn Lys Gln
2240                2245                2250

Lys Asn Ile Leu Arg Asn Ile Asp Asn Ile Leu Asn Lys Arg Glu
2255                2260                2265

Asn Ile Ile Asp Lys Val Ile Lys Cys Asn Cys Asp Asp Tyr Lys
2270                2275                2280

Asp Ile Leu Ile Gln Asn Glu Thr Glu Tyr Gln Lys Leu Gln Asn
2285                2290                2295

Ile Asn His Thr Tyr Glu Glu Lys Lys Lys Ser Ile Asp Ile Leu
2300                2305                2310
```

```
Lys Ile Lys Asn Ile Lys Gln Lys Asn Ile Gln Glu Tyr Lys Asn
2315                2320                2325

Lys Leu Glu Gln Met Asn Thr Ile Ile Asn Gln Ser Ile Glu Gln
2330                2335                2340

His Val Phe Ile Asn Ala Asp Ile Leu Gln Asn Glu Lys Ile Lys
2345                2350                2355

Leu Glu Glu Ile Ile Lys Asn Leu Asp Ile Leu Asp Glu Gln Ile
2360                2365                2370

Met Thr Tyr His Asn Ser Ile Asp Glu Leu Tyr Lys Leu Gly Ile
2375                2380                2385

Gln Cys Asp Asn His Leu Ile Thr Thr Ile Ser Val Val Val Asn
2390                2395                2400

Lys Asn Thr Thr Lys Ile Met Ile His Ile Lys Lys Gln Lys Glu
2405                2410                2415

Asp Ile Gln Lys Ile Asn Asn Tyr Ile Gln Thr Asn Tyr Met Ile
2420                2425                2430

Ile Asn Glu Glu Ala Leu Gln Phe His Arg Leu Tyr Gly His Asn
2435                2440                2445

Leu Ile Ser Glu Asp Asp Lys Asn Asn Leu Val His Ile Ile Lys
2450                2455                2460

Glu Gln Lys Asn Ile Tyr Thr Gln Lys Glu Ile Asp Ile Ser Lys
2465                2470                2475

Ile Ile Lys His Val Lys Lys Gly Leu Tyr Ser Leu Asn Glu His
2480                2485                2490

Asp Met Asn His Asp Thr His Met Asn Ile Ile Asn Glu His Ile
2495                2500                2505

Asn Asn Asn Ile Leu Gln Pro Tyr Thr Gln Leu Ile Asn Met Ile
2510                2515                2520

Lys Asp Ile Asp Asn Val Phe Ile Lys Ile Gln Asn Asn Lys Phe
2525                2530                2535

Glu Gln Ile Gln Lys Tyr Ile Glu Ile Ile Lys Ser Leu Glu Gln
2540                2545                2550

Leu Asn Lys Asn Ile Asn Thr Asp Asn Leu Asn Lys Leu Lys Asp
2555                2560                2565

Thr Gln Asn Lys Leu Ile Asn Ile Glu Thr Glu Met Lys His Lys
2570                2575                2580

Gln Lys Gln Leu Ile Asn Lys Met Asn Asp Ile Glu Lys Asp Asn
2585                2590                2595

Ile Thr Asp Gln Tyr Met His Asp Val Gln Gln Asn Ile Phe Glu
2600                2605                2610

Pro Ile Thr Leu Lys Met Asn Glu Tyr Asn Thr Leu Leu Asn Asp
2615                2620                2625

Asn His Asn Asn Ile Asn Asn Glu His Gln Phe Asn His Leu
2630                2635                2640

Asn Ser Leu His Thr Lys Ile Phe Ser His Asn Tyr Asn Lys Glu
2645                2650                2655

Gln Gln Gln Glu Tyr Ile Thr Asn Ile Met Gln Arg Ile Asp Val
2660                2665                2670

Phe Ile Asn Asp Leu Asp Thr Tyr Gln Tyr Glu Tyr Tyr Phe Tyr
2675                2680                2685

Glu Trp Asn Gln Glu Tyr Lys Gln Ile Asp Lys Asn Lys Ile Asn
2690                2695                2700

Gln His Ile Asn Asn Ile Lys Asn Asn Leu Ile His Val Lys Lys
```

-continued

```
            2705                2710                2715

Gln Phe Glu His Thr Leu Glu Asn Ile Lys Asn Glu Met Ile
        2720                2725                2730

Phe Asp Asn Ile Gln Leu Lys Lys Lys Asp Ile Asp Leu Ile Ile
    2735                2740                2745

Ile Asn Ile Asn Asn Thr Lys Glu Thr Tyr Leu Lys Glu Leu Asn
2750                2755                2760

Lys Lys Lys Asn Val Thr Lys Lys Lys Val Asp Glu Lys Ser
    2765                2770                2775

Glu Ile Asn Asn His His Thr Leu Gln His Asp Asn Gln Asn Val
    2780                2785                2790

Glu Gln Lys Asn Lys Ile Lys Asp His Asn Leu Ile Thr Lys Pro
    2795                2800                2805

Asn Asn Asn Ser Ser Glu Glu Ser His Gln Asn Glu Gln Met Lys
    2810                2815                2820

Glu Gln Asn Lys Asn Ile Leu Glu Lys Gln Thr Arg Asn Ile Lys
    2825                2830                2835

Pro His His Val His Asn His Asn His Asn Gln Asn Gln
    2840                2845                2850

Lys Asp Ser Thr Lys Leu Gln Glu Gln Asp Ile Ser Thr His Lys
    2855                2860                2865

Leu His Asn Thr Ile His Glu Gln Gln Ser Lys Asp Asn His Gln
    2870                2875                2880

Gly Asn Arg Glu Lys Lys Lys Asn Gly Asn His Glu Arg Met
    2885                2890                2895

Tyr Phe Ala Ser Gly Ile Val Val Ser Ile Leu Phe Leu Phe Ser
    2900                2905                2910

Phe Gly Phe Val Ile Asn Ser Lys Asn Asn Lys Gln Glu Tyr Asp
    2915                2920                2925

Lys Glu Gln Glu Lys Gln Gln Gln Asn Asp Phe Val Cys Asp Met
    2930                2935                2940

Asn Lys Met Asp Asp Lys Ser Thr Gln Lys Tyr Gly Arg Asn Gln
    2945                2950                2955

Glu Glu Val Met Glu Ile Phe Phe Asp Asn Asp Tyr Ile
    2960                2965                2970
```

<210> SEQ ID NO 11
<211> LENGTH: 3130
<212> TYPE: PRT
<213> ORGANISM: Plasmodium falciparum

<400> SEQUENCE: 11

```
Met Lys Thr Thr Leu Phe Cys Ser Ile Ser Phe Cys Asn Ile Phe
1               5                   10                  15

Phe Phe Leu Glu Leu Ser His Glu His Phe Val Gly Gln Ser Asn
            20                  25                  30

Thr His Gly Ala Ser Ser Val Thr Asp Phe Asn Phe Ser Glu Glu Lys
        35                  40                  45

Asn Leu Lys Ser Phe Glu Gly Lys Asn Asn Asn Asp Asn Tyr Ala
    50                  55                  60

Ser Ile Asn Arg Leu Tyr Arg Lys Lys Pro Tyr Met Lys Arg Ser Leu
65                  70                  75                  80

Ile Asn Leu Glu Asn Asp Leu Phe Arg Leu Glu Pro Ile Ser Tyr Ile
                85                  90                  95
```

-continued

Gln Arg Tyr Tyr Lys Lys Asn Ile Asn Arg Ser Asp Ile Phe His Asn
             100                 105                 110

Lys Lys Glu Arg Gly Ser Lys Val Tyr Ser Asn Val Ser Ser Phe His
     115                 120                 125

Ser Phe Ile Gln Glu Gly Lys Glu Val Glu Val Phe Ser Ile Trp
130                 135                 140

Gly Ser Asn Ser Val Leu Asp His Ile Asp Val Leu Arg Asp Asn Gly
145                 150                 155                 160

Thr Val Val Phe Ser Val Gln Pro Tyr Tyr Leu Asp Ile Tyr Thr Cys
                 165                 170                 175

Lys Glu Ala Ile Leu Phe Thr Thr Ser Phe Tyr Lys Asp Leu Asp Lys
             180                 185                 190

Ser Ser Ile Thr Lys Ile Asn Glu Asp Ile Glu Lys Phe Asn Glu Glu
         195                 200                 205

Ile Ile Lys Asn Glu Glu Gln Cys Leu Val Gly Gly Lys Thr Asp Phe
210                 215                 220

Asp Asn Leu Leu Ile Val Leu Glu Asn Ala Glu Lys Ala Asn Val Arg
225                 230                 235                 240

Lys Thr Leu Phe Asp Asn Thr Phe Asn Asp Tyr Lys Asn Lys Lys Ser
                 245                 250                 255

Ser Phe Tyr Asn Cys Leu Lys Asn Lys Asn Asp Tyr Asp Lys Lys
             260                 265                 270

Ile Lys Asn Ile Lys Asn Glu Ile Thr Lys Leu Leu Lys Asn Ile Glu
         275                 280                 285

Ser Thr Gly Asn Met Cys Lys Thr Glu Ser Tyr Val Met Asn Asn Asn
290                 295                 300

Leu Tyr Leu Leu Arg Val Asn Glu Val Lys Ser Thr Pro Ile Asp Leu
305                 310                 315                 320

Tyr Leu Asn Arg Ala Lys Glu Leu Leu Glu Ser Ser Lys Leu Val
                 325                 330                 335

Asn Pro Ile Lys Met Lys Leu Gly Asp Asn Lys Asn Met Tyr Ser Ile
             340                 345                 350

Gly Tyr Ile His Asp Glu Ile Lys Asp Ile Ile Lys Arg Tyr Asn Phe
         355                 360                 365

His Leu Lys His Ile Glu Lys Gly Lys Glu Tyr Ile Lys Arg Ile Thr
370                 375                 380

Gln Ala Asn Asn Ile Ala Asp Lys Met Lys Lys Asp Glu Leu Ile Lys
385                 390                 395                 400

Lys Ile Phe Glu Ser Ser Lys His Phe Ala Ser Phe Lys Tyr Ser Asn
                 405                 410                 415

Glu Met Ile Ser Lys Leu Asp Ser Leu Phe Ile Lys Asn Glu Glu Ile
             420                 425                 430

Leu Asn Asn Leu Phe Asn Asn Ile Phe Asn Ile Phe Lys Lys Lys Tyr
         435                 440                 445

Glu Thr Tyr Val Asp Met Lys Thr Ile Glu Ser Lys Tyr Thr Thr Val
     450                 455                 460

Met Thr Leu Ser Glu His Leu Leu Glu Tyr Ala Met Asp Val Leu Lys
465                 470                 475                 480

Ala Asn Pro Gln Lys Pro Ile Asp Pro Lys Ala Asn Leu Asp Ser Glu
                 485                 490                 495

Val Val Lys Leu Gln Ile Lys Ile Asn Glu Lys Ser Asn Glu Leu Asp
             500                 505                 510

Asn Ala Ile Ser Gln Val Lys Thr Leu Ile Ile Ile Met Lys Ser Phe 515                 520                 525
Tyr Asp Ile Ile Ile Ser Glu Lys Ala Ser Met Asp Glu Met Glu Lys
                530                 535                 540

Lys Glu Leu Ser Leu Asn Asn Tyr Ile Glu Lys Thr Asp Tyr Ile Leu
545                 550                 555                 560

Gln Thr Tyr Asn Ile Phe Lys Ser Lys Ser Asn Ile Ile Asn Asn Asn
                565                 570                 575

Ser Lys Asn Ile Ser Ser Lys Tyr Ile Thr Ile Glu Gly Leu Lys Asn
                580                 585                 590

Asp Ile Asp Glu Leu Asn Ser Leu Ile Ser Tyr Phe Lys Asp Ser Gln
                595                 600                 605

Glu Thr Leu Ile Lys Asp Asp Glu Leu Lys Lys Asn Met Lys Thr Asp
                610                 615                 620

Tyr Leu Asn Asn Val Lys Tyr Ile Glu Glu Asn Val Thr His Ile Asn
625                 630                 635                 640

Glu Ile Ile Leu Leu Lys Asp Ser Ile Thr Gln Arg Ile Ala Asp Ile
                645                 650                 655

Asp Glu Leu Asn Ser Leu Asn Leu Ile Asn Ile Asn Asp Phe Ile Asn
                660                 665                 670

Glu Lys Asn Ile Ser Gln Glu Lys Val Ser Tyr Asn Leu Asn Lys Leu
                675                 680                 685

Tyr Lys Gly Ser Phe Glu Glu Leu Glu Ser Glu Leu Ser His Phe Leu
                690                 695                 700

Asp Thr Lys Tyr Leu Phe His Glu Lys Lys Ser Val Asn Glu Leu Gln
705                 710                 715                 720

Thr Ile Leu Asn Thr Ser Asn Asn Glu Cys Ala Lys Leu Asn Phe Met
                725                 730                 735

Lys Ser Asp Asn Asn Asn Asn Asn Ser Asn Ile Ile Asn Leu
                740                 745                 750

Leu Lys Thr Glu Leu Ser His Leu Leu Ser Leu Lys Glu Asn Ile Ile
                755                 760                 765

Lys Lys Leu Leu Asn His Ile Glu Gln Asn Ile Gln Asn Ser Ser Asn
                770                 775                 780

Lys Tyr Thr Ile Thr Tyr Thr Asp Ile Asn Asn Arg Met Glu Asp Tyr
785                 790                 795                 800

Lys Glu Glu Ile Glu Ser Leu Glu Val Tyr Lys His Thr Ile Gly Asn
                805                 810                 815

Ile Gln Lys Glu Tyr Ile Leu His Leu Tyr Glu Asn Asp Lys Asn Ala
                820                 825                 830

Leu Ala Val His Asn Thr Ser Met Gln Ile Leu Gln Tyr Lys Asp Ala
                835                 840                 845

Ile Gln Asn Ile Lys Asn Lys Ile Ser Asp Asp Lys Ile Leu Lys
                850                 855                 860

Lys Tyr Lys Glu Met Asn Gln Asp Leu Leu Asn Tyr Tyr Glu Ile Leu
865                 870                 875                 880

Asp Lys Lys Leu Lys Asp Asn Thr Tyr Ile Lys Glu Met His Thr Ala
                885                 890                 895

Ser Leu Val Gln Ile Thr Gln Tyr Ile Pro Tyr Glu Asp Lys Thr Ile
                900                 905                 910

Ser Glu Leu Glu Gln Glu Phe Asn Asn Asn Gln Lys Leu Asp Asn
                915                 920                 925

Ile Leu Gln Asp Ile Asn Ala Met Asn Leu Asn Ile Asn Ile Leu Gln
                930                 935                 940

-continued

```
Thr Leu Asn Ile Gly Ile Asn Ala Cys Asn Thr Asn Lys Asn Val
945                 950                 955                 960

Glu His Leu Leu Asn Lys Lys Ile Glu Leu Lys Asn Ile Leu Asn Asp
            965                 970                 975

Gln Met Lys Ile Ile Lys Asn Asp Asp Ile Ile Gln Asp Asn Glu Lys
        980                 985                 990

Glu Asn Phe Ser Asn Val Leu Lys Lys Glu Glu Lys Leu Glu Lys
            995                 1000                1005

Glu Leu Asp Asp Ile Lys Phe Asn Asn Leu Lys Met Asp Ile His
    1010                1015                1020

Lys Leu Leu Asn Ser Tyr Asp His Thr Lys Gln Asn Ile Glu Ser
    1025                1030                1035

Asn Leu Lys Ile Asn Leu Asp Ser Phe Glu Lys Glu Lys Asp Ser
    1040                1045                1050

Trp Val His Phe Lys Ser Thr Ile Asp Ser Leu Tyr Val Glu Tyr
    1055                1060                1065

Asn Ile Cys Asn Gln Lys Thr His Asn Thr Ile Lys Gln Gln Lys
    1070                1075                1080

Asn Asp Ile Ile Glu Leu Ile Tyr Lys Arg Ile Lys Asp Ile Asn
    1085                1090                1095

Gln Glu Ile Ile Glu Lys Val Asp Asn Tyr Tyr Ser Leu Ser Asp
    1100                1105                1110

Lys Ala Leu Thr Lys Leu Lys Ser Ile His Phe Asn Ile Asp Lys
    1115                1120                1125

Glu Lys Tyr Lys Asn Pro Lys Ser Gln Glu Asn Ile Lys Leu Leu
    1130                1135                1140

Glu Asp Arg Val Met Ile Leu Glu Lys Lys Ile Lys Glu Asp Lys
    1145                1150                1155

Asp Ala Leu Ile Gln Ile Lys Asn Leu Ser His Asp His Phe Val
    1160                1165                1170

Asn Ala Asp Asn Glu Lys Lys Lys Gln Lys Glu Lys Glu Glu Asp
    1175                1180                1185

Asp Glu Gln Thr His Tyr Ser Lys Lys Arg Lys Val Met Gly Asp
    1190                1195                1200

Ile Tyr Lys Asp Ile Lys Lys Asn Leu Asp Glu Leu Asn Asn Lys
    1205                1210                1215

Asn Leu Ile Asp Ile Thr Leu Asn Glu Ala Asn Lys Ile Glu Ser
    1220                1225                1230

Glu Tyr Glu Lys Ile Leu Ile Asp Asp Ile Cys Glu Gln Ile Thr
    1235                1240                1245

Asn Glu Ala Lys Lys Ser Asp Thr Ile Lys Glu Lys Ile Glu Ser
    1250                1255                1260

Tyr Lys Lys Asp Ile Asp Tyr Val Asp Val Asp Val Ser Lys Thr
    1265                1270                1275

Arg Asn Asp His His Leu Asn Gly Asp Lys Ile His Asp Ser Phe
    1280                1285                1290

Phe Tyr Glu Asp Thr Leu Asn Tyr Lys Ala Tyr Phe Asp Lys Leu
    1295                1300                1305

Lys Asp Leu Tyr Glu Asn Ile Asn Lys Leu Thr Asn Glu Ser Asn
    1310                1315                1320

Gly Leu Lys Ser Asp Ala His Asn Asn Asn Thr Gln Val Asp Lys
    1325                1330                1335
```

```
Leu Lys Glu Ile Asn Leu Gln Val Phe Ser Asn Leu Gly Asn Ile
1340                1345                1350

Ile Lys Tyr Val Glu Lys Leu Glu Asn Thr Leu His Glu Leu Lys
1355                1360                1365

Asp Met Tyr Glu Phe Leu Glu Thr Ile Asp Ile Asn Lys Ile Leu
1370                1375                1380

Lys Ser Ile His Asn Ser Met Lys Lys Ser Glu Glu Tyr Ser Asn
1385                1390                1395

Glu Thr Lys Lys Ile Phe Glu Gln Ser Val Asn Ile Thr Asn Gln
1400                1405                1410

Phe Ile Glu Asp Val Glu Ile Leu Lys Thr Ser Ile Asn Pro Asn
1415                1420                1425

Tyr Glu Ser Leu Asn Asp Asp Gln Ile Asp Asp Asn Ile Lys Ser
1430                1435                1440

Leu Val Leu Lys Lys Glu Glu Ile Ser Glu Lys Arg Lys Gln Val
1445                1450                1455

Asn Lys Tyr Ile Thr Asp Ile Glu Ser Asn Lys Glu Gln Ser Asp
1460                1465                1470

Leu His Leu Arg Tyr Ala Ser Arg Ser Ile Tyr Val Ile Asp Leu
1475                1480                1485

Phe Ile Lys His Glu Ile Ile Asn Pro Ser Asp Gly Lys Asn Phe
1490                1495                1500

Asp Ile Ile Lys Val Lys Glu Met Ile Asn Lys Thr Lys Gln Val
1505                1510                1515

Ser Asn Glu Ala Met Glu Tyr Ala Asn Lys Met Asp Glu Lys Asn
1520                1525                1530

Lys Asp Ile Ile Lys Ile Glu Asn Glu Leu Tyr Asn Leu Ile Asn
1535                1540                1545

Asn Asn Ile Arg Ser Leu Lys Gly Val Lys Tyr Glu Lys Val Arg
1550                1555                1560

Lys Gln Ala Arg Asn Ala Ile Asp Asp Ile Asn Asn Ile His Ser
1565                1570                1575

Asn Ile Lys Thr Ile Leu Thr Lys Ser Lys Glu Arg Leu Asp Glu
1580                1585                1590

Ile Lys Lys Gln Pro Asn Ile Lys Arg Glu Gly Asp Val Leu Asn
1595                1600                1605

Asn Asp Lys Thr Lys Ile Ala Tyr Ile Thr Ile Gln Ile Asn Asn
1610                1615                1620

Gly Arg Ile Glu Ser Asn Leu Leu Asn Ile Leu Asn Met Lys His
1625                1630                1635

Asn Ile Asp Thr Ile Leu Asn Lys Ala Met Asp Tyr Met Asn Asp
1640                1645                1650

Val Ser Lys Ser Asp Gln Ile Val Ile Asn Ile Asp Ser Leu Asn
1655                1660                1665

Met Asn Asp Ile Tyr Asn Lys Asp Lys Asp Leu Leu Ile Asn Ile
1670                1675                1680

Leu Lys Glu Lys Gln Asn Met Glu Ala Glu Tyr Lys Lys Met Asn
1685                1690                1695

Glu Met Tyr Asn Tyr Val Asn Glu Thr Glu Lys Glu Ile Ile Lys
1700                1705                1710

His Lys Lys Asn Tyr Glu Ile Arg Ile Met Glu His Ile Lys Lys
1715                1720                1725

Glu Thr Asn Glu Lys Lys Lys Lys Phe Met Glu Ser Asn Asn Lys
```

```
                     1730                1735                1740
Ser Leu Thr Thr Leu Met Asp Ser Phe Arg Ser Met Phe Tyr Asn
    1745                1750                1755
Glu Tyr Ile Asn Asp Tyr Asn Ile Asn Glu Asn Phe Glu Lys His
    1760                1765                1770
Gln Asn Ile Leu Asn Glu Ile Tyr Asn Gly Phe Asn Glu Ser Tyr
    1775                1780                1785
Asn Ile Ile Asn Thr Lys Met Thr Glu Ile Ile Asn Asp Asn Leu
    1790                1795                1800
Asp Tyr Asn Glu Ile Lys Glu Ile Lys Glu Val Ala Gln Thr Glu
    1805                1810                1815
Tyr Asp Lys Leu Asn Lys Lys Val Asp Glu Leu Lys Asn Tyr Leu
    1820                1825                1830
Asn Asn Ile Lys Glu Gln Gly His Arg Leu Ile Asp Tyr Ile
    1835                1840                1845
Lys Glu Lys Ile Phe Asn Leu Tyr Ile Lys Cys Ser Glu Gln Gln
    1850                1855                1860
Asn Ile Ile Asp Asp Ser Tyr Asn Tyr Ile Thr Val Lys Lys Gln
    1865                1870                1875
Tyr Ile Lys Thr Ile Glu Asp Val Lys Phe Leu Leu Asp Ser Leu
    1880                1885                1890
Asn Thr Ile Glu Glu Lys Asn Lys Ser Val Ala Asn Leu Glu Ile
    1895                1900                1905
Cys Thr Asn Lys Glu Asp Ile Lys Asn Leu Leu Lys His Val Ile
    1910                1915                1920
Lys Leu Ala Asn Phe Ser Gly Ile Ile Val Met Ser Asp Thr Asn
    1925                1930                1935
Thr Glu Ile Thr Pro Glu Asn Pro Leu Glu Asp Asn Asp Leu Leu
    1940                1945                1950
Asn Leu Gln Leu Tyr Phe Glu Arg Lys His Glu Ile Thr Ser Thr
    1955                1960                1965
Leu Glu Asn Asp Ser Asp Leu Glu Leu Asp His Leu Gly Ser Asn
    1970                1975                1980
Ser Asp Glu Ser Ile Asp Asn Leu Lys Val Tyr Asn Asp Ile Ile
    1985                1990                1995
Glu Leu His Thr Tyr Ser Thr Gln Ile Leu Lys Tyr Leu Asp Asn
    2000                2005                2010
Ile Gln Lys Leu Lys Gly Asp Cys Asn Asp Leu Val Lys Asp Cys
    2015                2020                2025
Lys Glu Leu Arg Glu Leu Ser Thr Ala Leu Tyr Asp Leu Lys Ile
    2030                2035                2040
Gln Ile Thr Ser Val Ile Asn Arg Glu Asn Asp Ile Ser Asn Asn
    2045                2050                2055
Ile Asp Ile Val Ser Asn Lys Leu Asn Glu Ile Asp Ala Ile Gln
    2060                2065                2070
Tyr Asn Phe Glu Lys Tyr Lys Glu Ile Phe Asp Asn Val Glu Glu
    2075                2080                2085
Tyr Lys Thr Leu Asp Asp Thr Lys Asn Ala Tyr Ile Val Lys Lys
    2090                2095                2100
Ala Glu Ile Leu Lys Asn Val Asp Ile Asn Lys Thr Lys Glu Asp
    2105                2110                2115
Leu Asp Ile Tyr Phe Asn Asp Leu Asp Glu Leu Glu Lys Ser Leu
    2120                2125                2130
```

-continued

Thr Leu Ser Ser Asn Glu Met Glu Ile Lys Thr Ile Val Gln Asn
    2135                2140                2145

Ser Tyr Asn Ser Phe Ser Asp Ile Asn Lys Asn Ile Asn Asp Ile
    2150                2155                2160

Asp Lys Glu Met Lys Thr Leu Ile Pro Met Leu Asp Glu Leu Leu
    2165                2170                2175

Asn Glu Gly His Asn Ile Asp Ile Ser Leu Tyr Asn Phe Ile Ile
    2180                2185                2190

Arg Asn Ile Gln Ile Lys Ile Gly Asn Asp Ile Lys Asn Ile Arg
    2195                2200                2205

Glu Gln Glu Asn Asp Thr Asn Ile Cys Phe Glu Tyr Ile Gln Asn
    2210                2215                2220

Asn Tyr Asn Phe Ile Lys Ser Asp Ile Ser Ile Phe Asn Lys Tyr
    2225                2230                2235

Asp Asp His Ile Lys Val Asp Asn Tyr Ile Ser Asn Asn Ile Asp
    2240                2245                2250

Val Val Asn Lys His Asn Ser Leu Leu Ser Glu His Val Ile Asn
    2255                2260                2265

Ala Thr Asn Ile Ile Glu Asn Ile Met Thr Ser Ile Val Glu Ile
    2270                2275                2280

Asn Glu Asp Thr Glu Met Asn Ser Leu Glu Glu Thr Gln Asp Lys
    2285                2290                2295

Leu Leu Glu Leu Tyr Glu Asn Phe Lys Lys Lys Asn Ile Ile
    2300                2305                2310

Asn Asn Asn Tyr Lys Ile Val His Phe Asn Lys Leu Lys Glu Ile
    2315                2320                2325

Glu Asn Ser Leu Glu Thr Tyr Asn Ser Ile Ser Thr Asn Phe Asn
    2330                2335                2340

Lys Ile Asn Glu Thr Gln Asn Ile Asp Ile Leu Lys Asn Glu Phe
    2345                2350                2355

Asn Asn Ile Lys Thr Lys Ile Asn Asp Lys Val Lys Glu Leu Val
    2360                2365                2370

His Val Asp Ser Thr Leu Thr Leu Glu Ser Ile Gln Thr Phe Asn
    2375                2380                2385

Asn Leu Tyr Gly Asp Leu Met Ser Asn Ile Gln Asp Val Tyr Lys
    2390                2395                2400

Tyr Glu Asp Ile Asn Asn Val Glu Leu Lys Lys Val Lys Leu Tyr
    2405                2410                2415

Ile Glu Asn Ile Thr Asn Leu Leu Gly Arg Ile Asn Thr Phe Ile
    2420                2425                2430

Lys Glu Leu Asp Lys Tyr Gln Asp Glu Asn Asn Gly Ile Asp Lys
    2435                2440                2445

Tyr Ile Glu Ile Asn Lys Glu Asn Asn Ser Tyr Ile Ile Lys Leu
    2450                2455                2460

Lys Glu Lys Ala Asn Asn Leu Lys Glu Asn Phe Ser Lys Leu Leu
    2465                2470                2475

Gln Asn Ile Lys Arg Asn Glu Thr Glu Leu Tyr Asn Ile Asn Asn
    2480                2485                2490

Ile Lys Asp Asp Ile Met Asn Thr Gly Lys Ser Val Asn Asn Ile
    2495                2500                2505

Lys Gln Lys Phe Ser Ser Asn Leu Pro Leu Lys Glu Lys Leu Phe
    2510                2515                2520

```
Gln Met Glu Glu Met Leu Leu Asn Ile Asn Asn Ile Met Asn Glu
2525                2530                2535

Thr Lys Arg Ile Ser Asn Thr Ala Ala Tyr Thr Asn Ile Thr Leu
2540                2545                2550

Gln Asp Ile Glu Asn Asn Lys Asn Lys Glu Asn Asn Asn Met Asn
2555                2560                2565

Ile Glu Thr Ile Asp Lys Leu Ile Asp His Ile Lys Ile His Asn
2570                2575                2580

Glu Lys Ile Gln Ala Glu Ile Leu Ile Ile Asp Asp Ala Lys Arg
2585                2590                2595

Lys Val Lys Glu Ile Thr Asp Asn Ile Asn Lys Ala Phe Asn Glu
2600                2605                2610

Ile Thr Glu Asn Tyr Asn Asn Glu Asn Asn Gly Val Ile Lys Ser
2615                2620                2625

Ala Lys Asn Ile Val Asp Glu Ala Thr Tyr Leu Asn Asn Glu Leu
2630                2635                2640

Asp Lys Phe Leu Leu Lys Leu Asn Glu Leu Leu Ser His Asn Asn
2645                2650                2655

Asn Asp Ile Lys Asp Leu Gly Asp Glu Lys Leu Ile Leu Lys Glu
2660                2665                2670

Glu Glu Glu Arg Lys Glu Arg Glu Arg Leu Glu Lys Ala Lys Gln
2675                2680                2685

Glu Glu Glu Arg Lys Glu Arg Glu Arg Ile Glu Lys Glu Lys Gln
2690                2695                2700

Glu Lys Glu Arg Leu Glu Arg Glu Lys Gln Glu Gln Leu Lys Lys
2705                2710                2715

Glu Glu Glu Leu Arg Lys Lys Glu Gln Glu Arg Gln Glu Gln Gln
2720                2725                2730

Gln Lys Glu Glu Ala Leu Lys Arg Gln Glu Gln Glu Arg Leu Gln
2735                2740                2745

Lys Glu Glu Glu Leu Lys Arg Gln Glu Gln Glu Arg Leu Glu Arg
2750                2755                2760

Glu Lys Gln Glu Gln Leu Gln Lys Glu Glu Glu Leu Lys Arg Gln
2765                2770                2775

Glu Gln Glu Arg Leu Gln Lys Glu Glu Ala Leu Lys Arg Gln Glu
2780                2785                2790

Gln Glu Arg Leu Gln Lys Glu Glu Leu Lys Arg Gln Glu Gln
2795                2800                2805

Glu Arg Leu Glu Arg Glu Lys Gln Glu Gln Leu Gln Lys Glu Glu
2810                2815                2820

Glu Leu Lys Arg Gln Glu Gln Glu Arg Leu Gln Lys Glu Glu Ala
2825                2830                2835

Leu Lys Arg Gln Glu Gln Glu Arg Leu Gln Lys Glu Glu Glu Leu
2840                2845                2850

Lys Arg Gln Glu Gln Glu Arg Leu Glu Arg Lys Lys Ile Glu Leu
2855                2860                2865

Ala Glu Arg Glu Gln His Ile Lys Ser Lys Leu Glu Ser Asp Met
2870                2875                2880

Val Lys Ile Ile Lys Asp Glu Leu Thr Lys Glu Lys Asp Glu Ile
2885                2890                2895

Ile Lys Asn Lys Asp Ile Lys Leu Arg His Ser Leu Glu Gln Lys
2900                2905                2910

Trp Leu Lys His Leu Gln Asn Ile Leu Ser Leu Lys Ile Asp Ser
```

```
                            2915                2920                2925

Leu Leu Asn Lys Asn Asp Glu Val Ile Lys Asp Asn Glu Thr Gln
    2930                2935                2940

Leu Lys Thr Asn Ile Leu Asn Ser Leu Lys Asn Gln Leu Tyr Leu
    2945                2950                2955

Asn Leu Lys Arg Glu Leu Asn Glu Ile Ile Lys Glu Tyr Glu Glu
    2960                2965                2970

Asn Gln Lys Lys Ile Leu His Ser Asn Gln Leu Val Asn Asp Ser
    2975                2980                2985

Leu Glu Gln Lys Thr Asn Arg Leu Val Asp Ile Lys Pro Thr Lys
    2990                2995                3000

His Gly Asp Ile Tyr Thr Asn Lys Leu Ser Asp Asn Glu Thr Glu
    3005                3010                3015

Met Leu Ile Thr Ser Lys Glu Lys Lys Asp Glu Thr Glu Ser Thr
    3020                3025                3030

Lys Arg Ser Gly Thr Asp His Thr Asn Ser Ser Glu Ser Thr Thr
    3035                3040                3045

Asp Asp Asn Thr Asn Asp Arg Asn Phe Ser Arg Ser Lys Asn Leu
    3050                3055                3060

Ser Val Ala Ile Tyr Thr Ala Gly Ser Val Ala Leu Cys Val Leu
    3065                3070                3075

Ile Phe Ser Ser Ile Gly Leu Leu Leu Ile Lys Thr Asn Ser Gly
    3080                3085                3090

Asp Asn Asn Ser Asn Glu Ile Asn Glu Ala Phe Glu Pro Asn Asp
    3095                3100                3105

Asp Val Leu Phe Lys Glu Lys Asp Glu Ile Ile Glu Ile Thr Phe
    3110                3115                3120

Asn Asp Asn Asp Ser Thr Ile
    3125                3130

<210> SEQ ID NO 12
<211> LENGTH: 112
<212> TYPE: PRT
<213> ORGANISM: Artificial Sequence
<220> FEATURE:
<223> OTHER INFORMATION: pfRh2a/b antigenic fragment

<400> SEQUENCE: 12

Lys Lys Tyr Glu Thr Tyr Val Asp Met Lys Thr Ile Glu Ser Lys Tyr
1               5                   10                  15

Thr Thr Val Met Thr Leu Ser Glu His Leu Leu Glu Tyr Ala Met Asp
            20                  25                  30

Val Leu Lys Ala Asn Pro Gln Lys Pro Ile Asp Pro Lys Ala Asn Leu
        35                  40                  45

Asp Ser Glu Val Val Lys Leu Gln Ile Lys Ile Asn Glu Lys Ser Asn
    50                  55                  60

Glu Leu Asp Asn Ala Ile Ser Gln Val Lys Thr Leu Ile Ile Ile Met
65                  70                  75                  80

Lys Ser Phe Tyr Asp Ile Ile Ile Ser Glu Lys Ala Ser Met Asp Glu
                85                  90                  95

Met Glu Lys Lys Glu Leu Ser Leu Asn Asn Tyr Ile Glu Lys Thr Asp
                100                 105                 110

<210> SEQ ID NO 13
<211> LENGTH: 499
<212> TYPE: PRT
```

<213> ORGANISM: Artificial Sequence
<220> FEATURE:
<223> OTHER INFORMATION: pfRh2a/b antigenic fragment

<400> SEQUENCE: 13

```
Glu Leu Arg Glu Leu Ser Thr Ala Leu Tyr Asp Leu Lys Ile Gln Ile
1               5                   10                  15

Thr Ser Val Ile Asn Arg Glu Asn Asp Ile Ser Asn Asn Ile Asp Ile
            20                  25                  30

Val Ser Asn Lys Leu Asn Glu Ile Asp Ala Ile Gln Tyr Asn Phe Glu
        35                  40                  45

Lys Tyr Lys Glu Ile Phe Asp Asn Val Glu Glu Tyr Lys Thr Leu Asp
    50                  55                  60

Asp Thr Lys Asn Ala Tyr Ile Val Lys Lys Ala Glu Ile Leu Lys Asn
65                  70                  75                  80

Val Asp Ile Asn Lys Thr Lys Glu Asp Leu Asp Ile Tyr Phe Asn Asp
                85                  90                  95

Leu Asp Glu Leu Glu Lys Ser Leu Thr Leu Ser Ser Asn Glu Met Glu
            100                 105                 110

Ile Lys Thr Ile Val Gln Asn Ser Tyr Asn Ser Phe Ser Asp Ile Asn
        115                 120                 125

Lys Asn Ile Asn Asp Ile Asp Lys Glu Met Lys Thr Leu Ile Pro Met
    130                 135                 140

Leu Asp Glu Leu Leu Asn Glu Gly His Asn Ile Asp Ile Ser Leu Tyr
145                 150                 155                 160

Asn Phe Ile Ile Arg Asn Ile Gln Ile Lys Ile Gly Asn Asp Ile Lys
                165                 170                 175

Asn Ile Arg Glu Gln Glu Asn Asp Thr Asn Ile Cys Phe Glu Tyr Ile
            180                 185                 190

Gln Asn Asn Tyr Asn Phe Ile Lys Ser Asp Ile Ser Ile Phe Asn Lys
        195                 200                 205

Tyr Asp Asp His Ile Lys Val Asp Asn Tyr Ile Ser Asn Asn Ile Asp
    210                 215                 220

Val Val Asn Lys His Asn Ser Leu Leu Ser Glu His Val Ile Asn Ala
225                 230                 235                 240

Thr Asn Ile Ile Glu Asn Ile Met Thr Ser Ile Val Glu Ile Asn Glu
                245                 250                 255

Asp Thr Glu Met Asn Ser Leu Glu Glu Thr Gln Asp Lys Leu Leu Glu
            260                 265                 270

Leu Tyr Glu Asn Phe Lys Lys Gly Lys Asn Ile Ile Asn Asn Asn Tyr
        275                 280                 285

Lys Ile Val His Phe Asn Lys Leu Lys Glu Ile Glu Asn Ser Leu Glu
    290                 295                 300

Thr Tyr Asn Ser Ile Ser Thr Asn Phe Asn Lys Ile Asn Glu Thr Gln
305                 310                 315                 320

Asn Ile Asp Ile Leu Lys Asn Glu Phe Asn Ile Lys Thr Lys Ile
                325                 330                 335

Asn Asp Lys Val Lys Glu Leu Val His Val Asp Ser Thr Leu Thr Leu
            340                 345                 350

Glu Ser Ile Gln Thr Phe Asn Asn Leu Tyr Gly Asp Leu Met Ser Asn
        355                 360                 365

Ile Gln Asp Val Tyr Lys Tyr Glu Asp Ile Asn Asn Val Glu Leu Lys
    370                 375                 380

Lys Val Lys Leu Tyr Ile Glu Asn Ile Thr Asn Leu Leu Gly Arg Ile
```

Asn Thr Phe Ile Lys Glu Leu Asp Lys Tyr Gln Asp Glu Asn Asn Gly
385                 390                 395                 400

Ile Asp Lys Tyr Ile Glu Ile Asn Lys Glu Asn Asn Ser Tyr Ile Ile
            405                 410                 415

Lys Leu Lys Glu Lys Ala Asn Asn Leu Lys Glu Asn Phe Ser Lys Leu
        420                 425                 430

Leu Gln Asn Ile Lys Arg Asn Glu Thr Glu Leu Tyr Asn Ile Asn Asn
    435                 440                 445

Ile Lys Asp Asp Ile Met Asn Thr Gly Lys Ser Val Asn Asn Ile Lys
450                 455                 460

Gln Lys Phe Ser Ser Asn Leu Pro Leu Lys Glu Lys Leu Phe Gln Met
465                 470                 475                 480

Glu Glu Met
        485                 490                 495

<210> SEQ ID NO 14
<211> LENGTH: 3254
<212> TYPE: PRT
<213> ORGANISM: Plasmodium falciparum

<400> SEQUENCE: 14

Met Lys Thr Thr Leu Phe Cys Ser Ile Ser Phe Cys Asn Ile Ile Phe
1               5                   10                  15

Phe Phe Leu Glu Leu Ser His Glu His Phe Val Gly Gln Ser Ser Asn
            20                  25                  30

Thr His Gly Ala Ser Ser Val Thr Asp Phe Asn Phe Ser Glu Glu Lys
        35                  40                  45

Asn Leu Lys Ser Phe Glu Gly Lys Asn Asn Asn Asp Asn Tyr Ala
    50                  55                  60

Ser Ile Asn Arg Leu Tyr Arg Lys Lys Pro Tyr Met Lys Arg Ser Leu
65                  70                  75                  80

Ile Asn Leu Glu Asn Asp Leu Phe Arg Leu Glu Pro Ile Ser Tyr Ile
                85                  90                  95

Gln Arg Tyr Tyr Lys Lys Asn Ile Asn Arg Ser Asp Ile Phe His Asn
            100                 105                 110

Lys Lys Glu Arg Gly Ser Lys Val Tyr Ser Asn Val Ser Ser Phe His
        115                 120                 125

Ser Phe Ile Gln Glu Gly Lys Glu Val Glu Val Phe Ser Ile Trp
    130                 135                 140

Gly Ser Asn Ser Val Leu Asp His Ile Asp Val Leu Arg Asp Asn Gly
145                 150                 155                 160

Thr Val Val Phe Ser Val Gln Pro Tyr Tyr Leu Asp Ile Tyr Thr Cys
                165                 170                 175

Lys Glu Ala Ile Leu Phe Thr Thr Ser Phe Tyr Lys Asp Leu Asp Lys
            180                 185                 190

Ser Ser Ile Thr Lys Ile Asn Glu Asp Ile Glu Lys Phe Asn Glu Glu
        195                 200                 205

Ile Ile Lys Asn Glu Glu Gln Cys Leu Val Gly Gly Lys Thr Asp Phe
    210                 215                 220

Asp Asn Leu Leu Ile Val Leu Glu Asn Ala Glu Lys Ala Asn Val Arg
225                 230                 235                 240

Lys Thr Leu Phe Asp Asn Thr Phe Asn Asp Tyr Lys Asn Lys Lys Ser
                245                 250                 255

Ser Phe Tyr Asn Cys Leu Lys Asn Lys Lys Asn Asp Tyr Asp Lys Lys

```
              260                 265                 270
Ile Lys Asn Ile Lys Asn Glu Ile Thr Lys Leu Leu Lys Asn Ile Glu
            275                 280                 285
Ser Thr Gly Asn Met Cys Lys Thr Glu Ser Tyr Val Met Asn Asn Asn
            290                 295                 300
Leu Tyr Leu Leu Arg Val Asn Glu Val Lys Ser Thr Pro Ile Asp Leu
305                 310                 315                 320
Tyr Leu Asn Arg Ala Lys Glu Leu Leu Glu Ser Ser Ser Lys Leu Val
                325                 330                 335
Asn Pro Ile Lys Met Lys Leu Gly Asp Asn Lys Asn Met Tyr Ser Ile
                340                 345                 350
Gly Tyr Ile His Asp Glu Ile Lys Asp Ile Ile Lys Arg Tyr Asn Phe
            355                 360                 365
His Leu Lys His Ile Glu Lys Gly Lys Glu Tyr Ile Lys Arg Ile Thr
            370                 375                 380
Gln Ala Asn Asn Ile Ala Asp Lys Met Lys Lys Asp Glu Leu Ile Lys
385                 390                 395                 400
Lys Ile Phe Glu Ser Ser Lys His Phe Ala Ser Phe Lys Tyr Ser Asn
                405                 410                 415
Glu Met Ile Ser Lys Leu Asp Ser Leu Phe Ile Lys Asn Glu Glu Ile
            420                 425                 430
Leu Asn Asn Leu Phe Asn Asn Ile Phe Asn Ile Phe Lys Lys Lys Tyr
            435                 440                 445
Glu Thr Tyr Val Asp Met Lys Thr Ile Glu Ser Lys Tyr Thr Thr Val
            450                 455                 460
Met Thr Leu Ser Glu His Leu Leu Glu Tyr Ala Met Asp Val Leu Lys
465                 470                 475                 480
Ala Asn Pro Gln Lys Pro Ile Asp Pro Lys Ala Asn Leu Asp Ser Glu
                485                 490                 495
Val Val Lys Leu Gln Ile Lys Ile Asn Glu Lys Ser Asn Glu Leu Asp
            500                 505                 510
Asn Ala Ile Ser Gln Val Lys Thr Leu Ile Ile Met Lys Ser Phe
            515                 520                 525
Tyr Asp Ile Ile Ile Ser Glu Lys Ala Ser Met Asp Glu Met Glu Lys
            530                 535                 540
Lys Glu Leu Ser Leu Asn Asn Tyr Ile Glu Lys Thr Asp Tyr Ile Leu
545                 550                 555                 560
Gln Thr Tyr Asn Ile Phe Lys Ser Lys Ser Asn Ile Ile Asn Asn Asn
                565                 570                 575
Ser Lys Asn Ile Ser Ser Lys Tyr Ile Thr Ile Glu Gly Leu Lys Asn
            580                 585                 590
Asp Ile Asp Glu Leu Asn Ser Leu Ile Ser Tyr Phe Lys Asp Ser Gln
            595                 600                 605
Glu Thr Leu Ile Lys Asp Asp Glu Leu Lys Lys Asn Met Lys Thr Asp
            610                 615                 620
Tyr Leu Asn Asn Val Lys Tyr Ile Glu Glu Asn Val Thr His Ile Asn
625                 630                 635                 640
Glu Ile Ile Leu Leu Lys Asp Ser Ile Thr Gln Arg Ile Ala Asp Ile
                645                 650                 655
Asp Glu Leu Asn Ser Leu Asn Leu Ile Asn Ile Asn Asp Phe Ile Asn
            660                 665                 670
Glu Lys Asn Ile Ser Gln Glu Lys Val Ser Tyr Asn Leu Asn Lys Leu
            675                 680                 685
```

Tyr Lys Gly Ser Phe Glu Glu Leu Glu Ser Glu Leu Ser His Phe Leu
690                 695                 700

Asp Thr Lys Tyr Leu Phe His Glu Lys Lys Ser Val Asn Glu Leu Gln
705                 710                 715                 720

Thr Ile Leu Asn Thr Ser Asn Asn Glu Cys Ala Lys Leu Asn Phe Met
            725                 730                 735

Lys Ser Asp Asn Asn Asn Asn Asn Asn Ser Asn Ile Ile Asn Leu
                740                 745                 750

Leu Lys Thr Glu Leu Ser His Leu Leu Ser Leu Lys Glu Asn Ile Ile
            755                 760                 765

Lys Lys Leu Leu Asn His Ile Glu Gln Asn Ile Gln Asn Ser Ser Asn
            770                 775                 780

Lys Tyr Thr Ile Thr Tyr Thr Asp Ile Asn Asn Arg Met Glu Asp Tyr
785                 790                 795                 800

Lys Glu Glu Ile Glu Ser Leu Glu Val Tyr Lys His Thr Ile Gly Asn
                805                 810                 815

Ile Gln Lys Glu Tyr Ile Leu His Leu Tyr Glu Asn Asp Lys Asn Ala
            820                 825                 830

Leu Ala Val His Asn Thr Ser Met Gln Ile Leu Gln Tyr Lys Asp Ala
            835                 840                 845

Ile Gln Asn Ile Lys Asn Lys Ile Ser Asp Asp Ile Lys Ile Leu Lys
850                 855                 860

Lys Tyr Lys Glu Met Asn Gln Asp Leu Leu Asn Tyr Tyr Glu Ile Leu
865                 870                 875                 880

Asp Lys Lys Leu Lys Asp Asn Thr Tyr Ile Lys Glu Met His Thr Ala
                885                 890                 895

Ser Leu Val Gln Ile Thr Gln Tyr Ile Pro Tyr Glu Asp Lys Thr Ile
            900                 905                 910

Ser Glu Leu Glu Gln Glu Phe Asn Asn Asn Gln Lys Leu Asp Asn
            915                 920                 925

Ile Leu Gln Asp Ile Asn Ala Met Asn Leu Asn Ile Asn Ile Leu Gln
930                 935                 940

Thr Leu Asn Ile Gly Ile Asn Ala Cys Asn Thr Asn Lys Asn Val
945                 950                 955                 960

Glu His Leu Leu Asn Lys Lys Ile Glu Leu Lys Asn Ile Leu Asn Asp
                965                 970                 975

Gln Met Lys Ile Ile Lys Asn Asp Asp Ile Ile Gln Asp Asn Glu Lys
            980                 985                 990

Glu Asn Phe Ser Asn Val Leu Lys Lys Glu Glu Glu Lys Leu Glu Lys
            995                 1000                1005

Glu Leu Asp Asp Ile Lys Phe Asn Asn Leu Lys Met Asp Ile His
1010                1015                1020

Lys Leu Leu Asn Ser Tyr Asp His Thr Lys Gln Asn Ile Glu Ser
1025                1030                1035

Asn Leu Lys Ile Asn Leu Asp Ser Phe Glu Lys Glu Lys Asp Ser
1040                1045                1050

Trp Val His Phe Lys Ser Thr Ile Asp Ser Leu Tyr Val Glu Tyr
1055                1060                1065

Asn Ile Cys Asn Gln Lys Thr His Asn Thr Ile Lys Gln Gln Lys
1070                1075                1080

Asn Asp Ile Ile Glu Leu Ile Tyr Lys Arg Ile Lys Asp Ile Asn
1085                1090                1095

-continued

```
Gln Glu Ile Ile Glu Lys Val Asp Asn Tyr Tyr Ser Leu Ser Asp
    1100                1105                1110

Lys Ala Leu Thr Lys Leu Lys Ser Ile His Phe Asn Ile Asp Lys
    1115                1120                1125

Glu Lys Tyr Lys Asn Pro Lys Ser Gln Glu Asn Ile Lys Leu Leu
    1130                1135                1140

Glu Asp Arg Val Met Ile Leu Glu Lys Lys Ile Lys Glu Asp Lys
    1145                1150                1155

Asp Ala Leu Ile Gln Ile Lys Asn Leu Ser His Asp His Phe Val
    1160                1165                1170

Asn Ala Asp Asn Glu Lys Lys Gln Lys Glu Lys Glu Glu Asp
    1175                1180                1185

Asp Glu Gln Thr His Tyr Ser Lys Lys Arg Lys Val Met Gly Asp
    1190                1195                1200

Ile Tyr Lys Asp Ile Lys Lys Asn Leu Asp Glu Leu Asn Asn Lys
    1205                1210                1215

Asn Leu Ile Asp Ile Thr Leu Asn Glu Ala Asn Lys Ile Glu Ser
    1220                1225                1230

Glu Tyr Glu Lys Ile Leu Ile Asp Asp Ile Cys Glu Gln Ile Thr
    1235                1240                1245

Asn Glu Ala Lys Lys Ser Asp Thr Ile Lys Glu Lys Ile Glu Ser
    1250                1255                1260

Tyr Lys Lys Asp Ile Asp Tyr Val Asp Val Asp Val Ser Lys Thr
    1265                1270                1275

Arg Asn Asp His His Leu Asn Gly Asp Lys Ile His Asp Ser Phe
    1280                1285                1290

Phe Tyr Glu Asp Thr Leu Asn Tyr Lys Ala Tyr Phe Asp Lys Leu
    1295                1300                1305

Lys Asp Leu Tyr Glu Asn Ile Asn Lys Leu Thr Asn Glu Ser Asn
    1310                1315                1320

Gly Leu Lys Ser Asp Ala His Asn Asn Asn Thr Gln Val Asp Lys
    1325                1330                1335

Leu Lys Glu Ile Asn Leu Gln Val Phe Ser Asn Leu Gly Asn Ile
    1340                1345                1350

Ile Lys Tyr Val Glu Lys Leu Glu Asn Thr Leu His Glu Leu Lys
    1355                1360                1365

Asp Met Tyr Glu Phe Leu Glu Thr Ile Asp Ile Asn Lys Ile Leu
    1370                1375                1380

Lys Ser Ile His Asn Ser Met Lys Lys Ser Glu Glu Tyr Ser Asn
    1385                1390                1395

Glu Thr Lys Lys Ile Phe Glu Gln Ser Val Asn Ile Thr Asn Gln
    1400                1405                1410

Phe Ile Glu Asp Val Glu Ile Leu Lys Thr Ser Ile Asn Pro Asn
    1415                1420                1425

Tyr Glu Ser Leu Asn Asp Asp Gln Ile Asp Asn Ile Lys Ser
    1430                1435                1440

Leu Val Leu Lys Lys Glu Glu Ile Ser Glu Lys Arg Lys Gln Val
    1445                1450                1455

Asn Lys Tyr Ile Thr Asp Ile Glu Ser Asn Lys Glu Gln Ser Asp
    1460                1465                1470

Leu His Leu Arg Tyr Ala Ser Arg Ser Ile Tyr Val Ile Asp Leu
    1475                1480                1485

Phe Ile Lys His Glu Ile Ile Asn Pro Ser Asp Gly Lys Asn Phe
```

-continued

```
            1490                1495                1500

Asp Ile Ile Lys Val Lys Glu Met Ile Asn Lys Thr Lys Gln Val
            1505                1510                1515

Ser Asn Glu Ala Met Glu Tyr Ala Asn Lys Met Asp Glu Lys Asn
            1520                1525                1530

Lys Asp Ile Ile Lys Ile Glu Asn Glu Leu Tyr Asn Leu Ile Asn
            1535                1540                1545

Asn Asn Ile Arg Ser Leu Lys Gly Val Lys Tyr Glu Lys Val Arg
            1550                1555                1560

Lys Gln Ala Arg Asn Ala Ile Asp Asp Ile Asn Asn Ile His Ser
            1565                1570                1575

Asn Ile Lys Thr Ile Leu Thr Lys Ser Lys Glu Arg Leu Asp Glu
            1580                1585                1590

Ile Lys Lys Gln Pro Asn Ile Lys Arg Glu Gly Asp Val Leu Asn
            1595                1600                1605

Asn Asp Lys Thr Lys Ile Ala Tyr Ile Thr Ile Gln Ile Asn Asn
            1610                1615                1620

Gly Arg Ile Glu Ser Asn Leu Leu Asn Ile Leu Asn Met Lys His
            1625                1630                1635

Asn Ile Asp Thr Ile Leu Asn Lys Ala Met Asp Tyr Met Asn Asp
            1640                1645                1650

Val Ser Lys Ser Asp Gln Ile Val Ile Asn Ile Asp Ser Leu Asn
            1655                1660                1665

Met Asn Asp Ile Tyr Asn Lys Asp Lys Asp Leu Leu Ile Asn Ile
            1670                1675                1680

Leu Lys Glu Lys Gln Asn Met Glu Ala Glu Tyr Lys Lys Met Asn
            1685                1690                1695

Glu Met Tyr Asn Tyr Val Asn Glu Thr Glu Lys Glu Ile Ile Lys
            1700                1705                1710

His Lys Lys Asn Tyr Glu Ile Arg Ile Met Glu His Ile Lys Lys
            1715                1720                1725

Glu Thr Asn Glu Lys Lys Lys Lys Phe Met Glu Ser Asn Asn Lys
            1730                1735                1740

Ser Leu Thr Thr Leu Met Asp Ser Phe Arg Ser Met Phe Tyr Asn
            1745                1750                1755

Glu Tyr Ile Asn Asp Tyr Asn Ile Asn Glu Asn Phe Glu Lys His
            1760                1765                1770

Gln Asn Ile Leu Asn Glu Ile Tyr Asn Gly Phe Asn Glu Ser Tyr
            1775                1780                1785

Asn Ile Ile Asn Thr Lys Met Thr Glu Ile Ile Asn Asp Asn Leu
            1790                1795                1800

Asp Tyr Asn Glu Ile Lys Glu Ile Lys Glu Val Ala Gln Thr Glu
            1805                1810                1815

Tyr Asp Lys Leu Asn Lys Lys Val Asp Glu Leu Lys Asn Tyr Leu
            1820                1825                1830

Asn Asn Ile Lys Glu Gln Glu Gly His Arg Leu Ile Asp Tyr Ile
            1835                1840                1845

Lys Glu Lys Ile Phe Asn Leu Tyr Ile Lys Cys Ser Glu Gln Gln
            1850                1855                1860

Asn Ile Ile Asp Asp Ser Tyr Asn Tyr Ile Thr Val Lys Lys Gln
            1865                1870                1875

Tyr Ile Lys Thr Ile Glu Asp Val Lys Phe Leu Leu Asp Ser Leu
            1880                1885                1890
```

```
Asn Thr Ile Glu Glu Lys Asn Lys Ser Val Ala Asn Leu Glu Ile
1895                1900                1905

Cys Thr Asn Lys Glu Asp Ile Lys Asn Leu Leu Lys His Val Ile
1910                1915                1920

Lys Leu Ala Asn Phe Ser Gly Ile Ile Val Met Ser Asp Thr Asn
1925                1930                1935

Thr Glu Ile Thr Pro Glu Asn Pro Leu Glu Asp Asn Asp Leu Leu
1940                1945                1950

Asn Leu Gln Leu Tyr Phe Glu Arg Lys His Glu Ile Thr Ser Thr
1955                1960                1965

Leu Glu Asn Asp Ser Asp Leu Glu Leu Asp His Leu Gly Ser Asn
1970                1975                1980

Ser Asp Glu Ser Ile Asp Asn Leu Lys Val Tyr Asn Asp Ile Ile
1985                1990                1995

Glu Leu His Thr Tyr Ser Thr Gln Ile Leu Lys Tyr Leu Asp Asn
2000                2005                2010

Ile Gln Lys Leu Lys Gly Asp Cys Asn Asp Leu Val Lys Asp Cys
2015                2020                2025

Lys Glu Leu Arg Glu Leu Ser Thr Ala Leu Tyr Asp Leu Lys Ile
2030                2035                2040

Gln Ile Thr Ser Val Ile Asn Arg Glu Asn Asp Ile Ser Asn Asn
2045                2050                2055

Ile Asp Ile Val Ser Asn Lys Leu Asn Glu Ile Asp Ala Ile Gln
2060                2065                2070

Tyr Asn Phe Glu Lys Tyr Lys Glu Ile Phe Asp Asn Val Glu Glu
2075                2080                2085

Tyr Lys Thr Leu Asp Asp Thr Lys Asn Ala Tyr Ile Val Lys Lys
2090                2095                2100

Ala Glu Ile Leu Lys Asn Val Asp Ile Asn Lys Thr Lys Glu Asp
2105                2110                2115

Leu Asp Ile Tyr Phe Asn Asp Leu Asp Glu Leu Glu Lys Ser Leu
2120                2125                2130

Thr Leu Ser Ser Asn Glu Met Glu Ile Lys Thr Ile Val Gln Asn
2135                2140                2145

Ser Tyr Asn Ser Phe Ser Asp Ile Asn Lys Asn Ile Asn Asp Ile
2150                2155                2160

Asp Lys Glu Met Lys Thr Leu Ile Pro Met Leu Asp Glu Leu Leu
2165                2170                2175

Asn Glu Gly His Asn Ile Asp Ile Ser Leu Tyr Asn Phe Ile Ile
2180                2185                2190

Arg Asn Ile Gln Ile Lys Ile Gly Asn Asp Ile Lys Asn Ile Arg
2195                2200                2205

Glu Gln Glu Asn Asp Thr Asn Ile Cys Phe Glu Tyr Ile Gln Asn
2210                2215                2220

Asn Tyr Asn Phe Ile Lys Ser Asp Ile Ser Ile Phe Asn Lys Tyr
2225                2230                2235

Asp Asp His Ile Lys Val Asp Asn Tyr Ile Ser Asn Asn Ile Asp
2240                2245                2250

Val Val Asn Lys His Asn Ser Leu Leu Ser Glu His Val Ile Asn
2255                2260                2265

Ala Thr Asn Ile Ile Glu Asn Ile Met Thr Ser Ile Val Glu Ile
2270                2275                2280
```

```
Asn Glu Asp Thr Glu Met Asn Ser Leu Glu Glu Thr Gln Asp Lys
2285                2290                2295

Leu Leu Glu Leu Tyr Glu Asn Phe Lys Lys Glu Lys Asn Ile Ile
2300                2305                2310

Asn Asn Asn Tyr Lys Ile Val His Phe Asn Lys Leu Lys Glu Ile
2315                2320                2325

Glu Asn Ser Leu Glu Thr Tyr Asn Ser Ile Ser Thr Asn Phe Asn
2330                2335                2340

Lys Ile Asn Glu Thr Gln Asn Ile Asp Ile Leu Lys Asn Glu Phe
2345                2350                2355

Asn Asn Ile Lys Thr Lys Ile Asn Asp Lys Val Lys Glu Leu Val
2360                2365                2370

His Val Asp Ser Thr Leu Thr Leu Glu Ser Ile Gln Thr Phe Asn
2375                2380                2385

Asn Leu Tyr Gly Asp Leu Met Ser Asn Ile Gln Asp Val Tyr Lys
2390                2395                2400

Tyr Glu Asp Ile Asn Asn Val Glu Leu Lys Lys Val Lys Leu Tyr
2405                2410                2415

Ile Glu Asn Ile Thr Asn Leu Leu Gly Arg Ile Asn Thr Phe Ile
2420                2425                2430

Lys Glu Leu Asp Lys Tyr Gln Asp Glu Asn Asn Gly Ile Asp Lys
2435                2440                2445

Tyr Ile Glu Ile Asn Lys Glu Asn Asn Ser Tyr Ile Ile Lys Leu
2450                2455                2460

Lys Glu Lys Ala Asn Asn Leu Lys Glu Asn Phe Ser Lys Leu Leu
2465                2470                2475

Gln Asn Ile Lys Arg Asn Glu Thr Glu Leu Tyr Asn Ile Asn Asn
2480                2485                2490

Ile Lys Asp Asp Ile Met Asn Thr Gly Lys Ser Val Asn Asn Ile
2495                2500                2505

Lys Gln Lys Phe Ser Ser Asn Leu Pro Leu Lys Glu Lys Leu Phe
2510                2515                2520

Gln Met Glu Glu Met Leu Leu Asn Ile Asn Asn Ile Met Asn Glu
2525                2530                2535

Thr Lys Arg Ile Ser Asn Thr Asp Ala Tyr Thr Asn Ile Thr Leu
2540                2545                2550

Gln Asp Ile Glu Asn Asn Lys Asn Lys Glu Asn Asn Asn Met Asn
2555                2560                2565

Ile Glu Thr Ile Asp Lys Leu Ile Asp His Ile Lys Ile His Asn
2570                2575                2580

Glu Lys Ile Gln Ala Glu Ile Leu Ile Ile Asp Asp Ala Lys Arg
2585                2590                2595

Lys Val Lys Glu Ile Thr Asp Asn Ile Asn Lys Ala Phe Asn Glu
2600                2605                2610

Ile Thr Glu Asn Tyr Asn Asn Glu Asn Asn Gly Val Ile Lys Ser
2615                2620                2625

Ala Lys Asn Ile Val Asp Lys Ala Thr Tyr Leu Asn Asn Glu Leu
2630                2635                2640

Asp Lys Phe Leu Leu Lys Leu Asn Glu Leu Leu Ser His Asn Asn
2645                2650                2655

Asn Asp Ile Lys Asp Leu Gly Asp Glu Lys Leu Ile Leu Lys Glu
2660                2665                2670

Glu Glu Glu Arg Lys Glu Arg Glu Arg Leu Glu Lys Ala Lys Gln
```

```
                2675                2680                2685

Glu Glu Glu Arg Lys Glu Arg Glu Arg Ile Glu Lys Glu Lys Gln
    2690            2695            2700

Glu Lys Glu Arg Leu Glu Arg Glu Lys Gln Glu Gln Leu Lys Lys
    2705            2710            2715

Glu Ala Leu Lys Lys Gln Glu Gln Arg Gln Glu Gln Gln Gln
    2720            2725            2730

Lys Glu Glu Ala Leu Lys Arg Gln Glu Gln Glu Arg Leu Gln Lys
    2735            2740            2745

Glu Glu Glu Leu Lys Arg Gln Glu Gln Glu Arg Leu Glu Arg Glu
    2750            2755            2760

Lys Gln Glu Gln Leu Gln Lys Glu Glu Glu Leu Arg Lys Lys Glu
    2765            2770            2775

Gln Glu Lys Gln Gln Gln Arg Asn Ile Gln Glu Leu Glu Glu Gln
    2780            2785            2790

Lys Lys Pro Glu Ile Ile Asn Glu Ala Leu Val Lys Gly Asp Lys
    2795            2800            2805

Ile Leu Glu Gly Ser Asp Gln Arg Asn Met Glu Leu Ser Lys Pro
    2810            2815            2820

Asn Val Ser Met Asp Asn Thr Asn Asn Ser Pro Ile Ser Asn Ser
    2825            2830            2835

Glu Ile Thr Glu Ser Asp Asp Ile Asp Asn Ser Glu Asn Ile His
    2840            2845            2850

Thr Ser His Met Ser Asp Ile Glu Ser Thr Gln Thr Ser His Arg
    2855            2860            2865

Ser Asn Thr His Gly Gln Gln Ile Ser Asp Ile Val Glu Asp Gln
    2870            2875            2880

Ile Thr His Pro Ser Asn Ile Gly Gly Glu Lys Ile Thr His Asn
    2885            2890            2895

Asp Glu Ile Ser Ile Thr Gly Glu Arg Asn Asn Ile Ser Asp Val
    2900            2905            2910

Asn Asp Tyr Ser Glu Ser Ser Asn Ile Phe Glu Asn Gly Asp Ser
    2915            2920            2925

Thr Ile Asn Thr Ser Thr Arg Asn Thr Ser Ser Thr His Asp Glu
    2930            2935            2940

Ser His Ile Ser Pro Ile Ser Asn Ala Tyr Asp His Val Val Ser
    2945            2950            2955

Asp Asn Lys Lys Ser Met Asp Glu Asn Ile Lys Asp Lys Leu Lys
    2960            2965            2970

Ile Asp Glu Ser Ile Thr Thr Asp Glu Gln Ile Arg Leu Asp Asp
    2975            2980            2985

Asn Ser Asn Ile Val Arg Ile Asp Ser Thr Asp Gln Arg Asp Ala
    2990            2995            3000

Ser Ser His Gly Ser Ser Asn Arg Asp Asp Glu Ile Ser His
    3005            3010            3015

Val Gly Ser Asp Ile His Met Asp Ser Val Asp Ile His Asp Ser
    3020            3025            3030

Ile Asp Thr Asp Glu Asn Ala Asp His Arg His Asn Val Asn Ser
    3035            3040            3045

Val Asp Ser Leu Ser Ser Ser Asp Tyr Thr Asp Thr Gln Lys Asp
    3050            3055            3060

Phe Ser Ser Ile Ile Lys Asp Gly Gly Asn Lys Glu Gly His Ala
    3065            3070            3075
```

```
Glu Asn Glu Ser Lys Glu Tyr Glu Ser Gln Thr Glu Gln Thr His
    3080                3085                3090

Glu Glu Gly Ile Met Asn Pro Asn Lys Tyr Ser Ile Ser Glu Val
    3095                3100                3105

Asp Gly Ile Lys Leu Asn Glu Glu Ala Lys His Lys Ile Thr Glu
    3110                3115                3120

Lys Leu Val Asp Ile Tyr Pro Ser Thr Tyr Arg Thr Leu Asp Glu
    3125                3130                3135

Pro Met Glu Thr His Gly Pro Asn Glu Lys Phe His Met Phe Gly
    3140                3145                3150

Ser Pro Tyr Val Thr Glu Glu Asp Tyr Thr Glu Lys His Asp Tyr
    3155                3160                3165

Asp Lys His Glu Asp Phe Asn Asn Glu Arg Tyr Ser Asn His Asn
    3170                3175                3180

Lys Met Asp Asp Phe Val Tyr Asn Ala Gly Gly Val Val Cys Cys
    3185                3190                3195

Val Leu Phe Phe Ala Ser Ile Thr Phe Phe Ser Met Asp Arg Ser
    3200                3205                3210

Asn Lys Asp Glu Cys Asp Phe Asp Met Cys Glu Glu Val Asn Asn
    3215                3220                3225

Asn Asp His Leu Ser Asn Tyr Ala Asp Lys Glu Glu Ile Ile Glu
    3230                3235                3240

Ile Val Phe Asp Glu Asn Glu Glu Lys Tyr Phe
    3245                3250

<210> SEQ ID NO 15
<211> LENGTH: 1716
<212> TYPE: PRT
<213> ORGANISM: Plasmodium falciparum

<400> SEQUENCE: 15

Met Asn Lys Asn Ile Leu Trp Ile Thr Phe Phe Tyr Phe Leu Phe Phe
1               5                   10                  15

Leu Leu Asp Met Tyr Gln Gly Asn Asp Ala Ile Pro Ser Lys Glu Lys
            20                  25                  30

Lys Asn Asp Pro Glu Ala Asp Ser Lys Asn Ser Gln Asn Gln His Asp
        35                  40                  45

Ile Asn Lys Thr His His Thr Asn Asn Tyr Asp Leu Asn Ile Lys
    50                  55                  60

Asp Lys Asp Glu Lys Lys Arg Lys Asn Asp Asn Leu Ile Asn Asn Tyr
65                  70                  75                  80

Leu Tyr Ser Leu Leu Lys Leu Ser Tyr Asn Lys Asn Gln Asp Ile Tyr
                85                  90                  95

Lys Asn Ile Gln Asn Gly Gln Lys Leu Lys Thr Asp Ile Ile Leu Asn
            100                 105                 110

Ser Phe Val Gln Ile Asn Ser Ser Asn Ile Leu Met Asp Glu Ile Glu
        115                 120                 125

Asn Tyr Val Lys Lys Tyr Thr Glu Ser Asn Arg Ile Met Tyr Leu Gln
    130                 135                 140

Phe Lys Tyr Ile Tyr Leu Gln Ser Leu Asn Ile Thr Val Ser Phe Val
145                 150                 155                 160

Pro Pro Asn Ser Pro Phe Arg Ser Tyr Tyr Asp Lys Asn Leu Asn Lys
                165                 170                 175

Asp Ile Asn Glu Thr Cys His Ser Ile Gln Thr Leu Leu Asn Asn Leu
```

-continued

```
            180                 185                 190
Ile Ser Ser Lys Ile Ile Phe Lys Met Leu Glu Thr Thr Lys Glu Gln
            195                 200                 205

Ile Leu Leu Leu Trp Asn Asn Lys Lys Ile Ser Gln Gln Asn Tyr Asn
            210                 215                 220

Gln Glu Asn Gln Glu Lys Ser Lys Met Ile Asp Ser Glu Asn Glu Lys
225                 230                 235                 240

Leu Glu Lys Tyr Thr Asn Lys Phe Glu His Asn Ile Lys Pro His Ile
                    245                 250                 255

Glu Asp Ile Glu Lys Lys Val Asn Glu Tyr Ile Asn Asn Ser Asp Cys
                260                 265                 270

His Leu Thr Cys Ser Lys Tyr Lys Thr Ile Ile Asn Asn Tyr Ile Asp
            275                 280                 285

Glu Ile Ile Thr Thr Asn Thr Asn Ile Tyr Glu Asn Lys Tyr Asn Leu
            290                 295                 300

Pro Gln Glu Arg Ile Ile Lys Asn Tyr Asn His Asn Gly Ile Asn Asn
305                 310                 315                 320

Asp Asp Asn Phe Ile Glu Tyr Asn Ile Leu Asn Ala Asp Pro Asp Leu
                    325                 330                 335

Arg Ser His Phe Thr Thr Leu Leu Val Ser Arg Lys Gln Leu Ile Tyr
                340                 345                 350

Ile Glu Tyr Ile Tyr Phe Ile Asn Lys His Ile Val Asn Lys Ile Gln
            355                 360                 365

Glu Asn Phe Lys Leu Asn Gln Asn Lys Tyr Ile His Phe Ile Asn Ser
            370                 375                 380

Asn Asn Ala Val Asn Ala Ala Lys Glu Tyr Glu Tyr Ile Ile Lys Tyr
385                 390                 395                 400

Tyr Thr Thr Phe Lys Tyr Leu Gln Thr Leu Asn Lys Ser Leu Tyr Asp
                    405                 410                 415

Ser Ile Tyr Lys His Lys Ile Asn Asn Tyr Ser His Asn Ile Glu Asp
                420                 425                 430

Leu Ile Asn Gln Leu Gln His Lys Ile Asn Asn Leu Met Ile Ile Ser
            435                 440                 445

Phe Asp Lys Asn Lys Ser Ser Asp Leu Met Leu Gln Cys Thr Asn Ile
            450                 455                 460

Lys Lys Tyr Thr Asp Asp Ile Cys Leu Ser Ile Lys Pro Lys Ala Leu
465                 470                 475                 480

Glu Val Glu Tyr Leu Arg Asn Ile Asn Lys His Ile Asn Lys Asn Glu
                    485                 490                 495

Phe Leu Asn Lys Phe Met Gln Asn Glu Thr Phe Lys Lys Asn Ile Asp
                500                 505                 510

Asp Lys Ile Lys Glu Met Asn Asn Ile Tyr Asp Asn Ile Tyr Ile Ile
            515                 520                 525

Leu Lys Gln Lys Phe Leu Asn Lys Leu Asn Glu Ile Ile Gln Asn His
            530                 535                 540

Lys Asn Lys Gln Glu Thr Lys Leu Asn Thr Thr Ile Gln Glu Leu
545                 550                 555                 560

Leu Gln Leu Leu Lys Asp Ile Lys Glu Ile Gln Thr Gln Ile Asp
                    565                 570                 575

Thr Lys Ile Asn Thr Phe Asn Met Tyr Tyr Asn Asp Ile Gln Gln Ile
                580                 585                 590

Lys Ile Lys Ile Asn Gln Asn Glu Lys Glu Ile Lys Lys Val Leu Pro
            595                 600                 605
```

```
Gln Leu Tyr Ile Pro Lys Asn Glu Gln Glu Tyr Ile Gln Ile Tyr Lys
    610             615                 620
Asn Glu Leu Lys Asp Arg Ile Lys Glu Thr Gln Thr Lys Ile Asn Leu
625                 630                 635                 640
Glu Lys Gln Ile Leu Glu Leu Lys Glu Lys Glu His Tyr Ile Thr Asn
            645                 650                 655
Lys His Thr Tyr Leu Asn Phe Thr His Lys Thr Ile Gln Gln Ile Leu
            660                 665                 670
Gln Gln Gln Tyr Lys Asn Asn Thr Gln Glu Lys Asn Thr Leu Ala Gln
        675                 680                 685
Phe Leu Tyr Asn Ala Asp Ile Lys Lys Tyr Ile Asp Glu Leu Ile Pro
    690                 695                 700
Ile Thr Gln Gln Ile Gln Thr Lys Met Tyr Thr Thr Asn Asn Ile Glu
705                 710                 715                 720
His Ile Lys Gln Ile Leu Ile Asn Tyr Ile Gln Glu Cys Lys Pro Ile
            725                 730                 735
Gln Asn Ile Ser Glu His Thr Thr Tyr Thr Leu Tyr Gln Glu Ile Lys
            740                 745                 750
Thr Asn Leu Glu Asn Ile Glu Gln Lys Ile Met Gln Asn Ile Gln Gln
        755                 760                 765
Thr Thr Asn Arg Leu Lys Ile Asn Ile Lys Lys Ile Phe Asp Gln Ile
770                 775                 780
Asn Gln Lys Tyr Asp Asp Leu Thr Lys Asn Ile Asn Gln Met Asn Asp
785                 790                 795                 800
Glu Lys Ile Gly Leu Arg Gln Met Glu Asn Arg Leu Lys Gly Lys Tyr
            805                 810                 815
Glu Glu Ile Lys Lys Ala Asn Leu Gln Asp Arg Asp Ile Lys Tyr Ile
            820                 825                 830
Val Gln Asn Asn Asp Ala Asn Asn Asn Asn Ile Ile Ile
        835                 840                 845
Asn Gly Asn Asn Gln Thr Gly Asp Tyr Asn His Ile Leu Phe Asp Tyr
    850                 855                 860
Thr His Leu Trp Asp Asn Ala Gln Phe Thr Arg Thr Lys Glu Asn Ile
865                 870                 875                 880
Asn Asn Leu Lys Asp Asn Ile Gln Ile Asn Ile Asn Asn Ile Lys Ser
            885                 890                 895
Ile Ile Arg Asn Leu Gln Asn Glu Leu Asn Asn Tyr Asn Thr Leu Lys
            900                 905                 910
Ser Asn Ser Ile His Ile Tyr Asp Lys Ile His Thr Leu Glu Glu Leu
        915                 920                 925
Lys Ile Leu Thr Gln Glu Ile Asn Asp Lys Asn Val Ile Arg Lys Ile
    930                 935                 940
Tyr Asp Ile Glu Thr Ile Tyr Gln Asn Asp Leu His Asn Ile Glu Glu
945                 950                 955                 960
Ile Ile Lys Asn Ile Thr Ser Ile Tyr Tyr Lys Ile Asn Ile Leu Asn
            965                 970                 975
Ile Leu Ile Ile Cys Ile Lys Gln Thr Tyr Asn Asn Asn Lys Ser Ile
            980                 985                 990
Glu Ser Leu Lys Leu Lys Ile Asn  Asn Leu Thr Asn Ser  Thr Gln Glu
        995                 1000                1005
Tyr Ile  Asn Gln Ile Lys Ala  Ile Pro Thr Asn Leu  Leu Pro Glu
    1010                1015                1020
```

-continued

```
His Ile Lys Gln Lys Ser Val Ser Glu Leu Asn Ile Tyr Met Lys
    1025                1030                1035

Gln Ile Tyr Asp Lys Leu Asn Glu His Val Ile Asn Asn Leu Tyr
    1040                1045                1050

Thr Lys Ser Lys Asp Ser Leu Gln Phe Tyr Ile Asn Glu Lys Asn
    1055                1060                1065

Tyr Asn Asn Asn His Asp Asp His Asn Asp Asp His Asn Asp Val
    1070                1075                1080

Tyr Asn Asp Ile Lys Glu Asn Glu Ile Tyr Lys Asn Asn Lys Leu
    1085                1090                1095

Tyr Glu Cys Ile Gln Ile Lys Lys Asp Val Asp Glu Leu Tyr Asn
    1100                1105                1110

Ile Tyr Asp Gln Leu Phe Lys Asn Ile Ser Gln Asn Tyr Asn Asn
    1115                1120                1125

His Ser Leu Ser Phe Val His Ser Ile Asn Asn His Met Leu Ser
    1130                1135                1140

Ile Phe Gln Asp Thr Lys Tyr Gly Lys His Lys Asn Gln Gln Ile
    1145                1150                1155

Leu Ser Asp Ile Glu Asn Ile Ile Lys Gln Asn Glu His Thr Glu
    1160                1165                1170

Ser Tyr Lys Asn Leu Asp Thr Ser Asn Ile Gln Leu Ile Lys Glu
    1175                1180                1185

Gln Ile Lys Tyr Phe Leu Gln Ile Phe His Ile Leu Gln Glu Asn
    1190                1195                1200

Ile Thr Thr Phe Glu Asn Gln Tyr Lys Asp Leu Ile Ile Lys Met
    1205                1210                1215

Asn His Lys Ile Asn Asn Asn Leu Lys Asp Ile Thr His Ile Val
    1220                1225                1230

Ile Asn Asp Asn Asn Thr Leu Gln Glu Gln Asn Arg Ile Tyr Asn
    1235                1240                1245

Glu Leu Gln Asn Lys Ile Lys Gln Ile Lys Asn Val Ser Asp Val
    1250                1255                1260

Phe Thr His Asn Ile Asn Tyr Ser Gln Gln Ile Leu Asn Tyr Ser
    1265                1270                1275

Gln Ala Gln Asn Ser Phe Phe Asn Ile Phe Met Lys Phe Gln Asn
    1280                1285                1290

Ile Asn Asn Asp Ile Asn Ser Lys Arg Tyr Asn Val Gln Lys Lys
    1295                1300                1305

Ile Thr Glu Ile Ile Asn Ser Tyr Asp Ile Ile Asn Tyr Asn Lys
    1310                1315                1320

Asn Asn Ile Lys Asp Ile Tyr Gln Gln Phe Lys Asn Ile Gln Gln
    1325                1330                1335

Gln Leu Asn Thr Thr Glu Thr Gln Leu Asn His Ile Lys Gln Asn
    1340                1345                1350

Ile Asn His Phe Lys Tyr Phe Tyr Glu Ser His Gln Thr Ile Ser
    1355                1360                1365

Ile Val Lys Asn Met Gln Asn Glu Lys Leu Lys Ile Gln Glu Phe
    1370                1375                1380

Asn Lys Lys Ile Gln His Phe Lys Glu Glu Thr Gln Ile Met Ile
    1385                1390                1395

Asn Lys Leu Ile Gln Pro Ser His Ile His Leu His Lys Met Lys
    1400                1405                1410

Leu Pro Ile Thr Gln Gln Gln Leu Asn Thr Ile Leu His Arg Asn
```

```
                       1415                1420                1425

Glu Gln Thr Lys Asn Ala Thr Arg Ser Tyr Asn Met Asn Glu Glu
        1430                1435                1440

Glu Asn Glu Met Gly Tyr Gly Ile Thr Asn Lys Arg Lys Asn Ser
    1445                1450                1455

Glu Thr Asn Asp Met Ile Asn Thr Thr Ile Gly Asp Lys Thr Asn
1460                1465                1470

Val Leu Lys Asn Asp Asp Gln Glu Lys Gly Lys Arg Gly Thr Ser
    1475                1480                1485

Arg Asn Asn Asn Ile His Thr Asn Glu Asn Asn Ile Asn Asn Glu
1490                1495                1500

His Thr Asn Glu Asn Asn Ile Asn Asn Glu His Thr Asn Glu Lys
    1505                1510                1515

Asn Ile Asn Asn Glu His Ala Asn Glu Lys Asn Ile Tyr Asn Glu
    1520                1525                1530

His Thr Asn Glu Asn Asn Ile Asn Tyr Glu His Pro Asn Asn Tyr
    1535                1540                1545

Gln Gln Lys Asn Asp Glu Lys Ile Ser Leu Gln His Lys Thr Ile
    1550                1555                1560

Asn Thr Ser Gln Arg Thr Ile Asp Asp Ser Asn Met Asp Arg Asn
    1565                1570                1575

Asn Arg Tyr Asn Thr Ser Ser Gln Gln Lys Asn Asn Leu His Thr
    1580                1585                1590

Asn Asn Asn Ser Asn Ser Arg Tyr Asn Asn Asn His Asp Lys Gln
    1595                1600                1605

Asn Glu His Lys Tyr Asn Gln Gly Lys Ser Ser Gly Lys Asp Asn
    1610                1615                1620

Ala Tyr Tyr Arg Ile Phe Tyr Ala Gly Gly Ile Thr Ala Val Leu
    1625                1630                1635

Leu Leu Cys Ser Ser Thr Ala Phe Phe Phe Ile Lys Asn Ser Asn
    1640                1645                1650

Glu Pro His His Ile Phe Asn Ile Phe Gln Lys Glu Phe Ser Glu
    1655                1660                1665

Ala Asp Asn Ala His Ser Glu Glu Lys Glu Glu Tyr Leu Pro Val
    1670                1675                1680

Tyr Phe Asp Glu Val Glu Asp Glu Val Glu Asp Glu Val Glu Asp
    1685                1690                1695

Glu Asp Glu Asn Glu Asn Glu Val Glu Asn Glu Asn Glu Asp Phe
    1700                1705                1710

Asn Asp Ile
    1715

<210> SEQ ID NO 16
<211> LENGTH: 739
<212> TYPE: PRT
<213> ORGANISM: Artificial Sequence
<220> FEATURE:
<223> OTHER INFORMATION: pfRh4 antigenic fragment

<400> SEQUENCE: 16

Pro Ser Lys Glu Lys Lys Asn Asp Pro Glu Ala Asp Ser Lys Asn Ser
1               5                   10                  15

Gln Asn Gln His Asp Ile Asn Lys Thr His His Thr Asn Asn Asn Tyr
            20                  25                  30

Asp Leu Asn Ile Lys Asp Lys Asp Glu Lys Lys Arg Lys Asn Asp Asn
```

```
                35                  40                  45
Leu Ile Asn Asn Tyr Leu Tyr Ser Leu Leu Lys Leu Ser Tyr Asn Lys
 50                  55                  60
Asn Gln Asp Ile Tyr Lys Asn Ile Gln Asn Gly Gln Lys Leu Lys Thr
 65                  70                  75                  80
Asp Ile Ile Leu Asn Ser Phe Val Gln Ile Asn Ser Ser Asn Ile Leu
                 85                  90                  95
Met Asp Glu Ile Glu Asn Tyr Val Lys Lys Tyr Thr Glu Ser Asn Arg
                100                 105                 110
Ile Met Tyr Leu Gln Phe Lys Tyr Ile Tyr Leu Gln Ser Leu Asn Ile
                115                 120                 125
Thr Val Ser Phe Val Pro Pro Asn Ser Pro Phe Arg Ser Tyr Tyr Asp
130                 135                 140
Lys Asn Leu Asn Lys Asp Ile Asn Glu Thr Cys His Ser Ile Gln Thr
145                 150                 155                 160
Leu Leu Asn Asn Leu Ile Ser Ser Lys Ile Ile Phe Lys Met Leu Glu
                165                 170                 175
Thr Thr Lys Glu Gln Ile Leu Leu Trp Asn Asn Lys Lys Ile Ser
                180                 185                 190
Gln Gln Asn Tyr Asn Gln Asn Gln Glu Lys Ser Lys Met Ile Asp
                195                 200                 205
Ser Glu Asn Glu Lys Leu Glu Lys Tyr Thr Asn Lys Phe Glu His Asn
210                 215                 220
Ile Lys Pro His Ile Glu Asp Ile Glu Lys Lys Val Asn Glu Tyr Ile
225                 230                 235                 240
Asn Asn Ser Asp Cys His Leu Thr Cys Ser Lys Tyr Lys Thr Ile Ile
                245                 250                 255
Asn Asn Tyr Ile Asp Glu Ile Ile Thr Thr Asn Thr Asn Ile Tyr Glu
                260                 265                 270
Asn Lys Tyr Asn Leu Pro Gln Glu Arg Ile Ile Lys Asn Tyr Asn His
                275                 280                 285
Asn Gly Ile Asn Asn Asp Asp Asn Phe Ile Glu Tyr Asn Ile Leu Asn
                290                 295                 300
Ala Asp Pro Asp Leu Arg Ser His Phe Thr Thr Leu Leu Val Ser Arg
305                 310                 315                 320
Lys Gln Leu Ile Tyr Ile Glu Tyr Ile Tyr Phe Ile Asn Lys His Ile
                325                 330                 335
Val Asn Lys Ile Gln Glu Asn Phe Lys Leu Asn Gln Asn Lys Tyr Ile
                340                 345                 350
His Phe Ile Asn Ser Asn Asn Ala Val Asn Ala Ala Lys Glu Tyr Glu
                355                 360                 365
Tyr Ile Ile Lys Tyr Tyr Thr Thr Phe Lys Tyr Leu Gln Thr Leu Asn
                370                 375                 380
Lys Ser Leu Tyr Asp Ser Ile Tyr Lys His Lys Ile Asn Asn Tyr Ser
385                 390                 395                 400
His Asn Ile Glu Asp Leu Ile Asn Gln Leu Gln His Lys Ile Asn Asn
                405                 410                 415
Leu Met Ile Ile Ser Phe Asp Lys Asn Lys Ser Ser Asp Leu Met Leu
                420                 425                 430
Gln Cys Thr Asn Ile Lys Lys Tyr Thr Asp Asp Ile Cys Leu Ser Ile
                435                 440                 445
Lys Pro Lys Ala Leu Glu Val Glu Tyr Leu Arg Asn Ile Asn Lys His
450                 455                 460
```

```
Ile Asn Lys Asn Glu Phe Leu Asn Lys Phe Met Gln Asn Glu Thr Phe
465                 470                 475                 480

Lys Lys Asn Ile Asp Asp Lys Ile Lys Glu Met Asn Asn Ile Tyr Asp
                485                 490                 495

Asn Ile Tyr Ile Ile Leu Lys Gln Lys Phe Leu Asn Lys Leu Asn Glu
            500                 505                 510

Ile Ile Gln Asn His Lys Asn Lys Gln Glu Thr Lys Leu Asn Thr Thr
        515                 520                 525

Thr Ile Gln Glu Leu Leu Gln Leu Leu Lys Asp Ile Lys Glu Ile Gln
530                 535                 540

Thr Lys Gln Ile Asp Thr Lys Ile Asn Thr Phe Asn Met Tyr Tyr Asn
545                 550                 555                 560

Asp Ile Gln Gln Ile Lys Ile Lys Ile Asn Gln Asn Glu Lys Glu Ile
                565                 570                 575

Lys Lys Val Leu Pro Gln Leu Tyr Ile Pro Lys Asn Glu Gln Glu Tyr
            580                 585                 590

Ile Gln Ile Tyr Lys Asn Glu Leu Lys Asp Arg Ile Lys Glu Thr Gln
        595                 600                 605

Thr Lys Ile Asn Leu Glu Lys Gln Ile Leu Glu Leu Lys Glu Lys Glu
610                 615                 620

His Tyr Ile Thr Asn Lys His Thr Tyr Leu Asn Phe Thr His Lys Thr
625                 630                 635                 640

Ile Gln Gln Ile Leu Gln Gln Tyr Lys Asn Asn Thr Gln Glu Lys
                645                 650                 655

Asn Thr Leu Ala Gln Phe Leu Tyr Asn Ala Asp Ile Lys Tyr Ile
            660                 665                 670

Asp Glu Leu Ile Pro Ile Thr Gln Gln Ile Gln Thr Lys Met Tyr Thr
        675                 680                 685

Thr Asn Asn Ile Glu His Ile Lys Gln Ile Leu Ile Asn Tyr Ile Gln
690                 695                 700

Glu Cys Lys Pro Ile Gln Asn Ile Ser Glu His Thr Thr Tyr Thr Leu
705                 710                 715                 720

Tyr Gln Glu Ile Lys Thr Asn Leu Glu Asn Ile Glu Gly Lys Ile Met
                725                 730                 735

Gln Asn Ile

<210> SEQ ID NO 17
<211> LENGTH: 526
<212> TYPE: PRT
<213> ORGANISM: Plasmodium falciparum

<400> SEQUENCE: 17

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95
```

-continued

```
Tyr Leu Phe Ile Pro Ser His Asn Ser Phe Ile Lys Lys Tyr Ser Val
                100                 105                 110
Phe Asn Gln Ile Asn Asp Gly Met Leu Leu Asn Glu Lys Asn Asp Val
            115                 120                 125
Lys Asn Asn Glu Asp Tyr Lys Asn Val Asp Tyr Lys Asn Val Asn Phe
130                 135                 140
Leu Gln Tyr His Phe Lys Glu Leu Ser Asn Tyr Asn Ile Ala Asn Ser
145                 150                 155                 160
Ile Asp Ile Leu Gln Glu Lys Glu Gly His Leu Asp Phe Val Ile Ile
                165                 170                 175
Pro His Tyr Thr Phe Leu Asp Tyr Tyr Lys His Leu Ser Tyr Asn Ser
            180                 185                 190
Ile Tyr His Lys Ser Ser Thr Tyr Gly Lys Cys Ile Ala Val Asp Ala
        195                 200                 205
Phe Ile Lys Lys Ile Asn Glu Thr Tyr Asp Lys Val Lys Ser Lys Cys
    210                 215                 220
Asn Asp Ile Lys Asn Asp Leu Ile Ala Thr Ile Lys Lys Leu Glu His
225                 230                 235                 240
Pro Tyr Asp Ile Asn Asn Lys Asn Asp Asp Ser Tyr Arg Tyr Asp Ile
                245                 250                 255
Ser Glu Glu Ile Asp Asp Lys Ser Glu Glu Thr Asp Asp Glu Thr Glu
            260                 265                 270
Glu Val Glu Asp Ser Ile Gln Asp Thr Asp Ser Asn His Thr Pro Ser
        275                 280                 285
Asn Lys Lys Lys Asn Asp Leu Met Asn Arg Thr Phe Lys Lys Met Met
    290                 295                 300
Asp Glu Tyr Asn Thr Lys Lys Lys Leu Ile Lys Cys Ile Lys Asn
305                 310                 315                 320
His Glu Asn Asp Phe Asn Lys Ile Cys Met Asp Met Lys Asn Tyr Gly
                325                 330                 335
Thr Asn Leu Phe Glu Gln Leu Ser Cys Tyr Asn Asn Asn Phe Cys Asn
            340                 345                 350
Thr Asn Gly Ile Arg Tyr His Tyr Asp Glu Tyr Ile His Lys Leu Ile
        355                 360                 365
Leu Ser Val Lys Ser Lys Asn Leu Asn Lys Asp Leu Ser Asp Met Thr
    370                 375                 380
Asn Ile Leu Gln Gln Ser Glu Leu Leu Leu Thr Asn Leu Asn Lys Lys
385                 390                 395                 400
Met Gly Ser Tyr Ile Tyr Ile Asp Thr Ile Lys Phe Ile His Lys Glu
                405                 410                 415
Met Lys His Ile Phe Asn Arg Ile Glu Tyr His Thr Lys Ile Ile Asn
            420                 425                 430
Asp Lys Thr Lys Ile Ile Gln Asp Lys Ile Lys Leu Asn Ile Trp Arg
        435                 440                 445
Thr Phe Gln Lys Asp Glu Leu Leu Lys Arg Ile Leu Asp Met Ser Asn
    450                 455                 460
Glu Tyr Ser Leu Phe Ile Thr Ser Asp His Leu Arg Gln Met Leu Tyr
465                 470                 475                 480
Asn Thr Phe Tyr Ser Lys Glu Lys His Leu Asn Asn Ile Phe His His
                485                 490                 495
Leu Ile Tyr Val Leu Gln Met Lys Phe Asn Asp Val Pro Ile Lys Met
            500                 505                 510
```

```
Glu Tyr Phe Gln Thr Tyr Lys Lys Asn Lys Pro Leu Thr Gln
            515                 520                 525
```

```
<210> SEQ ID NO 18
<211> LENGTH: 503
<212> TYPE: PRT
<213> ORGANISM: Artificial Sequence
<220> FEATURE:
<223> OTHER INFORMATION: Rh5 antigenic fragment

<400> SEQUENCE: 18

Ser Phe Glu Asn Ala Ile Lys Lys Thr Lys Asn Gln Glu Asn Asn Leu
1               5                   10                  15

Thr Leu Leu Pro Ile Lys Ser Thr Glu Glu Lys Asp Asp Ile Lys
            20                  25                  30

Asn Gly Lys Asp Ile Lys Lys Glu Ile Asp Asn Asp Lys Glu Asn Ile
            35                  40                  45

Lys Thr Asn Asn Ala Lys Asp His Ser Thr Tyr Ile Lys Ser Tyr Leu
50                  55                  60

Asn Thr Asn Val Asn Asp Gly Leu Lys Tyr Leu Phe Ile Pro Ser His
65                  70                  75                  80

Asn Ser Phe Ile Lys Lys Tyr Ser Val Phe Asn Gln Ile Asn Asp Gly
                85                  90                  95

Met Leu Leu Asn Glu Lys Asn Asp Val Lys Asn Asn Glu Asp Tyr Lys
            100                 105                 110

Asn Val Asp Tyr Lys Asn Val Asn Phe Leu Gln Tyr His Phe Lys Glu
            115                 120                 125

Leu Ser Asn Tyr Asn Ile Ala Asn Ser Ile Asp Ile Leu Gln Glu Lys
130                 135                 140

Glu Gly His Leu Asp Phe Val Ile Ile Pro His Tyr Thr Phe Leu Asp
145                 150                 155                 160

Tyr Tyr Lys His Leu Ser Tyr Asn Ser Ile Tyr His Lys Ser Ser Thr
                165                 170                 175

Tyr Gly Lys Cys Ile Ala Val Asp Ala Phe Ile Lys Lys Ile Asn Glu
            180                 185                 190

Thr Tyr Asp Lys Val Lys Ser Lys Cys Asn Asp Ile Lys Asn Asp Leu
            195                 200                 205

Ile Ala Thr Ile Lys Lys Leu Glu His Pro Tyr Asp Ile Asn Asn Lys
210                 215                 220

Asn Asp Asp Ser Tyr Arg Tyr Asp Ile Ser Glu Glu Ile Asp Asp Lys
225                 230                 235                 240

Ser Glu Glu Thr Asp Asp Glu Thr Glu Glu Val Glu Asp Ser Ile Gln
                245                 250                 255

Asp Thr Asp Ser Asn His Thr Pro Ser Asn Lys Lys Asn Asp Leu
            260                 265                 270

Met Asn Arg Thr Phe Lys Lys Met Met Asp Glu Tyr Asn Thr Lys Lys
            275                 280                 285

Lys Lys Leu Ile Lys Cys Ile Lys Asn His Glu Asn Asp Phe Asn Lys
            290                 295                 300

Ile Cys Met Asp Met Lys Asn Tyr Gly Thr Asn Leu Phe Glu Gln Leu
305                 310                 315                 320

Ser Cys Tyr Asn Asn Asn Phe Cys Asn Thr Asn Gly Ile Arg Tyr His
                325                 330                 335

Tyr Asp Glu Tyr Ile His Lys Leu Ile Leu Ser Val Lys Ser Lys Asn
            340                 345                 350
```

```
Leu Asn Lys Asp Leu Ser Asp Met Thr Asn Ile Leu Gln Gln Ser Glu
            355                 360                 365

Leu Leu Leu Thr Asn Leu Asn Lys Lys Met Gly Ser Tyr Ile Tyr Ile
        370                 375                 380

Asp Thr Ile Lys Phe Ile His Lys Glu Met Lys His Ile Phe Asn Arg
385                 390                 395                 400

Ile Glu Tyr His Thr Lys Ile Ile Asn Asp Lys Thr Lys Ile Ile Gln
                405                 410                 415

Asp Lys Ile Lys Leu Asn Ile Trp Arg Thr Phe Gln Lys Asp Glu Leu
            420                 425                 430

Leu Lys Arg Ile Leu Asp Met Ser Asn Glu Tyr Ser Leu Phe Ile Thr
        435                 440                 445

Ser Asp His Leu Arg Gln Met Leu Tyr Asn Thr Phe Tyr Ser Lys Glu
    450                 455                 460

Lys His Leu Asn Asn Ile Phe His His Leu Ile Tyr Val Leu Gln Met
465                 470                 475                 480

Lys Phe Asn Asp Val Pro Ile Leu Met Glu Tyr Phe Gln Thr Tyr Lys
                485                 490                 495

Lys Asn Lys Pro Leu Thr Gln
            500

<210> SEQ ID NO 19
<211> LENGTH: 379
<212> TYPE: PRT
<213> ORGANISM: Artificial Sequence
<220> FEATURE:
<223> OTHER INFORMATION: Rh5 antigenic fragment

<400> SEQUENCE: 19

His Phe Lys Glu Leu Ser Asn Tyr Asn Ile Ala Asn Ser Ile Asp Ile
1               5                   10                  15

Leu Gln Glu Lys Glu Gly His Leu Asp Phe Val Ile Ile Pro His Tyr
            20                  25                  30

Thr Phe Leu Asp Tyr Tyr Lys His Leu Ser Tyr Asn Ser Ile Tyr His
        35                  40                  45

Lys Ser Ser Thr Tyr Gly Lys Cys Ile Ala Val Asp Ala Phe Ile Lys
    50                  55                  60

Lys Ile Asn Glu Thr Tyr Asp Lys Val Lys Ser Lys Cys Asn Asp Ile
65                  70                  75                  80

Lys Asn Asp Leu Ile Ala Thr Ile Lys Lys Leu Glu His Pro Tyr Asp
                85                  90                  95

Ile Asn Asn Lys Asn Asp Asp Ser Tyr Arg Tyr Asp Ile Ser Glu Glu
            100                 105                 110

Ile Asp Asp Lys Ser Glu Glu Thr Asp Asp Glu Thr Glu Glu Val Glu
        115                 120                 125

Asp Ser Ile Gln Asp Thr Asp Ser Asn His Thr Pro Ser Asn Lys Lys
    130                 135                 140

Lys Asn Asp Leu Met Asn Arg Thr Phe Lys Lys Met Met Asp Glu Tyr
145                 150                 155                 160

Asn Thr Lys Lys Lys Lys Leu Ile Lys Cys Ile Lys Asn His Glu Asn
                165                 170                 175

Asp Phe Asn Lys Ile Cys Met Asp Met Lys Asn Tyr Gly Thr Asn Leu
            180                 185                 190

Phe Glu Gln Leu Ser Cys Tyr Asn Asn Asn Phe Cys Asn Thr Asn Gly
        195                 200                 205
```

```
Ile Arg Tyr His Tyr Asp Glu Tyr Ile His Lys Leu Ile Leu Ser Val
210                 215                 220

Lys Ser Lys Asn Leu Asn Lys Asp Leu Ser Asp Met Thr Asn Ile Leu
225                 230                 235                 240

Gln Gln Ser Glu Leu Leu Leu Thr Asn Leu Asn Lys Lys Met Gly Ser
                245                 250                 255

Tyr Ile Tyr Ile Asp Thr Ile Lys Phe Ile His Lys Glu Met Lys His
                260                 265                 270

Ile Phe Asn Arg Ile Glu Tyr His Thr Lys Ile Ile Asn Asp Lys Thr
                275                 280                 285

Lys Ile Ile Gln Asp Lys Ile Lys Leu Asn Ile Trp Arg Thr Phe Gln
290                 295                 300

Lys Asp Glu Leu Leu Lys Arg Ile Leu Asp Met Ser Asn Glu Tyr Ser
305                 310                 315                 320

Leu Phe Ile Thr Ser Asp His Leu Arg Gln Met Leu Tyr Asn Thr Phe
                325                 330                 335

Tyr Ser Lys Glu Lys His Leu Asn Asn Ile Phe His His Leu Ile Tyr
                340                 345                 350

Val Leu Gln Met Lys Phe Asn Asp Val Pro Ile Lys Met Glu Tyr Phe
                355                 360                 365

Gln Thr Tyr Lys Lys Asn Lys Pro Leu Thr Gln
370                 375

<210> SEQ ID NO 20
<211> LENGTH: 384
<212> TYPE: PRT
<213> ORGANISM: Artificial Sequence
<220> FEATURE:
<223> OTHER INFORMATION: Rh5 antigenic fragment

<400> SEQUENCE: 20

Asn Phe Leu Gln Tyr His Phe Lys Glu Leu Ser Asn Tyr Asn Ile Ala
1               5                   10                  15

Asn Ser Ile Asp Ile Leu Gln Glu Lys Glu Gly His Leu Asp Phe Val
                20                  25                  30

Ile Ile Pro His Tyr Thr Phe Leu Asp Tyr Tyr Lys His Leu Ser Tyr
            35                  40                  45

Asn Ser Ile Tyr His Lys Ser Ser Thr Tyr Gly Lys Cys Ile Ala Val
    50                  55                  60

Asp Ala Phe Ile Lys Lys Ile Asn Glu Thr Tyr Asp Lys Val Lys Ser
65                  70                  75                  80

Lys Cys Asn Asp Ile Lys Asn Asp Leu Ile Ala Thr Ile Lys Lys Leu
                85                  90                  95

Glu His Pro Tyr Asp Ile Asn Asn Lys Asn Asp Asp Ser Tyr Arg Tyr
            100                 105                 110

Asp Ile Ser Glu Glu Ile Asp Asp Lys Ser Glu Glu Thr Asp Asp Glu
        115                 120                 125

Thr Glu Glu Val Glu Asp Ser Ile Gln Asp Thr Asp Ser Asn His Thr
130                 135                 140

Pro Ser Asn Lys Lys Lys Asn Asp Leu Met Asn Arg Thr Phe Lys Lys
145                 150                 155                 160

Met Met Asp Glu Tyr Asn Thr Lys Lys Lys Leu Ile Lys Cys Ile
                165                 170                 175

Lys Asn His Glu Asn Asp Phe Asn Lys Ile Cys Met Asp Met Lys Asn
            180                 185                 190
```

-continued

```
Tyr Gly Thr Asn Leu Phe Glu Gln Leu Ser Cys Tyr Asn Asn Asn Phe
            195                 200                 205

Cys Asn Thr Asn Gly Ile Arg Tyr His Tyr Asp Glu Tyr Ile His Lys
210                 215                 220

Leu Ile Leu Ser Val Lys Ser Lys Asn Leu Asn Lys Asp Leu Ser Asp
225                 230                 235                 240

Met Thr Asn Ile Leu Gln Gln Ser Glu Leu Leu Thr Asn Leu Asn
            245                 250                 255

Lys Lys Met Gly Ser Tyr Ile Tyr Ile Asp Thr Ile Lys Phe Ile His
                260                 265                 270

Lys Glu Met Lys His Ile Phe Asn Arg Ile Glu Tyr His Thr Lys Ile
            275                 280                 285

Ile Asn Asp Lys Thr Lys Ile Ile Gln Asp Lys Ile Lys Leu Asn Ile
290                 295                 300

Trp Arg Thr Phe Gln Lys Asp Glu Leu Leu Lys Arg Ile Leu Asp Met
305                 310                 315                 320

Ser Asn Glu Tyr Ser Leu Phe Ile Thr Ser Asp His Leu Arg Gln Met
                325                 330                 335

Leu Tyr Asn Thr Phe Tyr Ser Lys Glu Lys His Leu Asn Asn Ile Phe
            340                 345                 350

His His Leu Ile Tyr Val Leu Gln Met Lys Phe Asn Asp Val Pro Ile
        355                 360                 365

Lys Met Glu Tyr Phe Gln Thr Tyr Lys Lys Asn Lys Pro Leu Thr Gln
    370                 375                 380
```

<210> SEQ ID NO 21
<211> LENGTH: 389
<212> TYPE: PRT
<213> ORGANISM: Artificial Sequence
<220> FEATURE:
<223> OTHER INFORMATION: Rh5 antigenic fragment

<400> SEQUENCE: 21

```
Asp Tyr Lys Asn Val Asn Phe Leu Gln Tyr His Phe Lys Glu Leu Ser
1               5                   10                  15

Asn Tyr Asn Ile Ala Asn Ser Ile Asp Ile Leu Gln Glu Lys Glu Gly
            20                  25                  30

His Leu Asp Phe Val Ile Ile Pro His Tyr Thr Phe Leu Asp Tyr Tyr
        35                  40                  45

Lys His Leu Ser Tyr Asn Ser Ile Tyr His Lys Ser Ser Thr Tyr Gly
    50                  55                  60

Lys Cys Ile Ala Val Asp Ala Phe Ile Lys Lys Ile Asn Glu Thr Tyr
65                  70                  75                  80

Asp Lys Val Lys Ser Lys Cys Asn Asp Ile Lys Asn Asp Leu Ile Ala
                85                  90                  95

Thr Ile Lys Lys Leu Glu His Pro Tyr Asp Ile Asn Asn Lys Asn Asp
            100                 105                 110

Asp Ser Tyr Arg Tyr Asp Ile Ser Glu Glu Ile Asp Lys Ser Glu
        115                 120                 125

Glu Thr Asp Asp Glu Thr Glu Glu Val Glu Asp Ser Ile Gln Asp Thr
    130                 135                 140

Asp Ser Asn His Thr Pro Ser Asn Lys Lys Asn Asp Leu Met Asn
145                 150                 155                 160

Arg Thr Phe Lys Lys Met Met Asp Glu Tyr Asn Thr Lys Lys Lys Lys
                165                 170                 175
```

```
Leu Ile Lys Cys Ile Lys Asn His Glu Asn Asp Phe Asn Lys Ile Cys
                180                 185                 190

Met Asp Met Lys Asn Tyr Gly Thr Asn Leu Phe Glu Gln Leu Ser Cys
            195                 200                 205

Tyr Asn Asn Asn Phe Cys Asn Thr Asn Gly Ile Arg Tyr His Tyr Asp
        210                 215                 220

Glu Tyr Ile His Lys Leu Ile Leu Ser Val Lys Ser Lys Asn Leu Asn
225                 230                 235                 240

Lys Asp Leu Ser Asp Met Thr Asn Ile Leu Gln Gln Ser Glu Leu Leu
                245                 250                 255

Leu Thr Asn Leu Asn Lys Lys Met Gly Ser Tyr Ile Tyr Ile Asp Thr
            260                 265                 270

Ile Lys Phe Ile His Lys Glu Met Lys His Ile Phe Asn Arg Ile Glu
        275                 280                 285

Tyr His Thr Lys Ile Ile Asn Asp Lys Thr Lys Ile Ile Gln Asp Lys
        290                 295                 300

Ile Lys Leu Asn Ile Trp Arg Thr Phe Gln Lys Asp Glu Leu Leu Lys
305                 310                 315                 320

Arg Ile Leu Asp Met Ser Asn Glu Tyr Ser Leu Phe Ile Thr Ser Asp
                325                 330                 335

His Leu Arg Gln Met Leu Tyr Asn Thr Phe Tyr Ser Lys Glu Lys His
            340                 345                 350

Leu Asn Asn Ile Phe His His Leu Ile Tyr Val Leu Gln Met Lys Phe
        355                 360                 365

Asn Asp Val Pro Ile Lys Met Glu Tyr Phe Gln Thr Tyr Lys Lys Asn
        370                 375                 380

Lys Pro Leu Thr Gln
385

<210> SEQ ID NO 22
<211> LENGTH: 374
<212> TYPE: PRT
<213> ORGANISM: Artificial Sequence
<220> FEATURE:
<223> OTHER INFORMATION: Rh5 antigenic fragment

<400> SEQUENCE: 22

Ser Asn Tyr Asn Ile Ala Asn Ser Ile Asp Ile Leu Gln Glu Lys Glu
1               5                   10                  15

Gly His Leu Asp Phe Val Ile Pro His Tyr Thr Phe Leu Asp Tyr
                20                  25                  30

Tyr Lys His Leu Ser Tyr Asn Ser Ile Tyr His Lys Ser Ser Thr Tyr
            35                  40                  45

Gly Lys Cys Ile Ala Val Asp Ala Phe Ile Lys Ile Asn Glu Thr
        50                  55                  60

Tyr Asp Lys Val Lys Ser Lys Cys Asn Asp Ile Lys Asn Asp Leu Ile
65                  70                  75                  80

Ala Thr Ile Lys Lys Leu Glu His Pro Tyr Asp Ile Asn Asn Lys Asn
                85                  90                  95

Asp Asp Ser Tyr Arg Tyr Asp Ile Ser Glu Glu Ile Asp Asp Lys Ser
            100                 105                 110

Glu Glu Thr Asp Asp Glu Thr Glu Glu Val Glu Asp Ser Ile Gln Asp
        115                 120                 125

Thr Asp Ser Asn His Thr Pro Ser Asn Lys Lys Asn Asp Leu Met
    130                 135                 140
```

```
Asn Arg Thr Phe Lys Lys Met Met Asp Glu Tyr Asn Thr Lys Lys Lys
145                 150                 155                 160

Lys Leu Ile Lys Cys Ile Lys Asn His Glu Asn Asp Phe Asn Lys Ile
            165                 170                 175

Cys Met Asp Met Lys Asn Tyr Gly Thr Asn Leu Phe Glu Gln Leu Ser
            180                 185                 190

Cys Tyr Asn Asn Phe Cys Asn Thr Asn Gly Ile Arg Tyr His Tyr
        195                 200                 205

Asp Glu Tyr Ile His Lys Leu Ile Leu Ser Val Lys Ser Lys Asn Leu
    210                 215                 220

Asn Lys Asp Leu Ser Asp Met Thr Asn Ile Leu Gln Gln Ser Glu Leu
225                 230                 235                 240

Leu Leu Thr Asn Leu Asn Lys Lys Met Gly Ser Tyr Ile Tyr Ile Asp
            245                 250                 255

Thr Ile Lys Phe Ile His Lys Glu Met Lys His Ile Phe Asn Arg Ile
            260                 265                 270

Glu Tyr His Thr Lys Ile Ile Asn Asp Lys Thr Lys Ile Ile Gln Asp
        275                 280                 285

Lys Ile Lys Leu Asn Ile Trp Arg Thr Phe Gln Lys Asp Glu Leu Leu
290                 295                 300

Lys Arg Ile Leu Asp Met Ser Asn Glu Tyr Ser Leu Phe Ile Thr Ser
305                 310                 315                 320

Asp His Leu Arg Gln Met Leu Tyr Asn Thr Phe Tyr Ser Lys Glu Lys
            325                 330                 335

His Leu Asn Asn Ile Phe His His Leu Ile Tyr Val Leu Gln Met Lys
        340                 345                 350

Phe Asn Asp Val Pro Ile Lys Met Glu Tyr Phe Gln Thr Tyr Lys Lys
            355                 360                 365

Asn Lys Pro Leu Thr Gln
        370

<210> SEQ ID NO 23
<211> LENGTH: 369
<212> TYPE: PRT
<213> ORGANISM: Artificial Sequence
<220> FEATURE:
<223> OTHER INFORMATION: Rh5 antigenic fragment

<400> SEQUENCE: 23

Ala Asn Ser Ile Asp Ile Leu Gln Glu Lys Glu Gly His Leu Asp Phe
1               5                   10                  15

Val Ile Ile Pro His Tyr Thr Phe Leu Asp Tyr Tyr Lys His Leu Ser
            20                  25                  30

Tyr Asn Ser Ile Tyr His Lys Ser Thr Tyr Gly Lys Cys Ile Ala
        35                  40                  45

Val Asp Ala Phe Ile Lys Lys Ile Asn Glu Thr Tyr Asp Lys Val Lys
    50                  55                  60

Ser Lys Cys Asn Asp Ile Lys Asn Asp Leu Ile Ala Thr Ile Lys Lys
65                  70                  75                  80

Leu Glu His Pro Tyr Asp Ile Asn Asn Lys Asn Asp Asp Ser Tyr Arg
            85                  90                  95

Tyr Asp Ile Ser Glu Glu Ile Asp Asp Lys Ser Glu Glu Thr Asp Asp
        100                 105                 110

Glu Thr Glu Glu Val Glu Asp Ser Ile Gln Asp Thr Asp Ser Asn His
    115                 120                 125
```

```
Thr Pro Ser Asn Lys Lys Asn Asp Leu Met Asn Arg Thr Phe Lys
    130                 135                 140

Lys Met Met Asp Glu Tyr Asn Thr Lys Lys Lys Leu Ile Lys Cys
145                 150                 155                 160

Ile Lys Asn His Glu Asn Asp Phe Asn Lys Ile Cys Met Asp Met Lys
                165                 170                 175

Asn Tyr Gly Thr Asn Leu Phe Glu Gln Leu Ser Cys Tyr Asn Asn Asn
                180                 185                 190

Phe Cys Asn Thr Asn Gly Ile Arg Tyr His Tyr Asp Glu Tyr Ile His
                195                 200                 205

Lys Leu Ile Leu Ser Val Lys Ser Lys Asn Leu Asn Lys Asp Leu Ser
    210                 215                 220

Asp Met Thr Asn Ile Leu Gln Gln Ser Glu Leu Leu Leu Thr Asn Leu
225                 230                 235                 240

Asn Lys Lys Met Gly Ser Tyr Ile Tyr Ile Asp Thr Ile Lys Phe Ile
                245                 250                 255

His Lys Glu Met Lys His Ile Phe Asn Arg Ile Glu Tyr His Thr Lys
                260                 265                 270

Ile Ile Asn Asp Lys Thr Lys Ile Ile Gln Asp Lys Ile Lys Leu Asn
    275                 280                 285

Ile Trp Arg Thr Phe Gln Lys Asp Glu Leu Leu Lys Arg Ile Leu Asp
    290                 295                 300

Met Ser Asn Glu Tyr Ser Leu Phe Ile Thr Ser Asp His Leu Arg Gln
305                 310                 315                 320

Met Leu Tyr Asn Thr Phe Tyr Ser Lys Glu Lys His Leu Asn Asn Ile
                325                 330                 335

Phe His His Leu Ile Tyr Val Leu Gln Met Lys Phe Asn Asp Val Pro
                340                 345                 350

Ile Lys Met Glu Tyr Phe Gln Thr Tyr Lys Asn Lys Pro Leu Thr
                355                 360                 365
Gln

<210> SEQ ID NO 24
<211> LENGTH: 170
<212> TYPE: PRT
<213> ORGANISM: Artificial Sequence
<220> FEATURE:
<223> OTHER INFORMATION: Rh5 antigenic fragment

<400> SEQUENCE: 24

Asn Ser Ile Tyr His Lys Ser Ser Thr Tyr Gly Lys Cys Ile Ala Val
1               5                   10                  15

Asp Ala Phe Ile Lys Lys Ile Asn Glu Thr Tyr Asp Lys Val Lys Ser
                20                  25                  30

Lys Cys Asn Asp Ile Lys Asn Asp Leu Ile Ala Thr Ile Lys Lys Leu
            35                  40                  45

Glu His Pro Tyr Asp Ile Asn Asn Lys Asn Asp Asp Ser Tyr Arg Tyr
        50                  55                  60

Asp Ile Ser Glu Glu Ile Asp Asp Lys Ser Glu Glu Thr Asp Asp Glu
65                  70                  75                  80

Thr Glu Glu Val Glu Asp Ser Ile Gln Asp Thr Asp Ser Asn His Thr
                85                  90                  95

Pro Ser Asn Lys Lys Asn Asp Leu Met Asn Arg Thr Phe Lys Lys
            100                 105                 110

Met Met Asp Glu Tyr Asn Thr Lys Lys Lys Lys Leu Ile Lys Cys Ile
```

```
            115                 120                 125
Lys Asn His Glu Asn Asp Phe Asn Lys Ile Cys Met Asp Met Lys Asn
        130                 135                 140

Tyr Gly Thr Asn Leu Phe Glu Gln Leu Ser Cys Tyr Asn Asn Asn Phe
145                 150                 155                 160

Cys Asn Thr Asn Gly Ile Arg Tyr His Tyr
                165                 170

<210> SEQ ID NO 25
<211> LENGTH: 157
<212> TYPE: PRT
<213> ORGANISM: Artificial Sequence
<220> FEATURE:
<223> OTHER INFORMATION: Rh5 antigenic fragment

<400> SEQUENCE: 25

Ile Ala Val Asp Ala Phe Ile Lys Lys Ile Asn Glu Thr Tyr Asp Lys
1               5                   10                  15

Val Lys Ser Lys Cys Asn Asp Ile Lys Asn Asp Leu Ile Ala Thr Ile
            20                  25                  30

Lys Lys Leu Glu His Pro Tyr Asp Ile Asn Asn Lys Asn Asp Asp Ser
        35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65                  70                  75                  80

Asn His Thr Pro Ser Asn Lys Lys Asn Asp Leu Met Asn Arg Thr
                85                  90                  95

Phe Lys Lys Met Met Asp Glu Tyr Asn Thr Lys Lys Lys Leu Ile
            100                 105                 110

Lys Cys Ile Lys Asn His Glu Asn Asp Phe Asn Lys Ile Cys Met Asp
        115                 120                 125

Met Lys Asn Tyr Gly Thr Asn Leu Phe Glu Gln Leu Ser Cys Tyr Asn
    130                 135                 140

Asn Asn Phe Cys Asn Thr Asn Gly Ile Arg Tyr His Tyr
145                 150                 155

<210> SEQ ID NO 26
<211> LENGTH: 147
<212> TYPE: PRT
<213> ORGANISM: Artificial Sequence
<220> FEATURE:
<223> OTHER INFORMATION: Rh5 antigenic fragment

<400> SEQUENCE: 26

Ile Ala Val Asp Ala Phe Ile Lys Lys Ile Asn Glu Thr Tyr Asp Lys
1               5                   10                  15

Val Lys Ser Lys Cys Asn Asp Ile Lys Asn Asp Leu Ile Ala Thr Ile
            20                  25                  30

Lys Lys Leu Glu His Pro Tyr Asp Ile Asn Asn Lys Asn Asp Asp Ser
        35                  40                  45

Tyr Arg Tyr Asp Ile Ser Glu Glu Ile Asp Asp Lys Ser Glu Glu Thr
    50                  55                  60

Asp Asp Glu Thr Glu Glu Val Glu Asp Ser Ile Gln Asp Thr Asp Ser
65                  70                  75                  80

Asn His Thr Pro Ser Asn Lys Lys Asn Asp Leu Met Asn Arg Thr
                85                  90                  95
```

```
Phe Lys Lys Met Met Asp Glu Tyr Asn Thr Lys Lys Lys Leu Ile
            100                 105                 110
Lys Cys Ile Lys Asn His Glu Asn Asp Phe Asn Lys Ile Cys Met Asp
        115                 120                 125
Met Lys Asn Tyr Gly Thr Asn Leu Phe Glu Gln Leu Ser Cys Tyr Asn
130                 135                 140
Asn Asn Phe
145

<210> SEQ ID NO 27
<211> LENGTH: 141
<212> TYPE: PRT
<213> ORGANISM: Artificial Sequence
<220> FEATURE:
<223> OTHER INFORMATION: Rh5 antigenic fragment

<400> SEQUENCE: 27

Ile Ala Val Asp Ala Phe Ile Lys Lys Ile Asn Glu Thr Tyr Asp Lys
1               5                   10                  15
Val Lys Ser Lys Cys Asn Asp Ile Lys Asn Asp Leu Ile Ala Thr Ile
            20                  25                  30
Lys Lys Leu Glu His Pro Tyr Asp Ile Asn Asn Lys Asn Asp Asp Ser
        35                  40                  45
Tyr Arg Tyr Asp Ile Ser Glu Glu Ile Asp Asp Lys Ser Glu Glu Thr
50                  55                  60
Asp Asp Glu Thr Glu Glu Val Glu Asp Ser Ile Gln Asp Thr Asp Ser
65                  70                  75                  80
Asn His Thr Pro Ser Asn Lys Lys Asn Asp Leu Met Asn Arg Thr
                85                  90                  95
Phe Lys Lys Met Met Asp Glu Tyr Asn Thr Lys Lys Lys Leu Ile
            100                 105                 110
Lys Cys Ile Lys Asn His Glu Asn Asp Phe Asn Lys Ile Cys Met Asp
        115                 120                 125
Met Lys Asn Tyr Gly Thr Asn Leu Phe Glu Gln Leu Ser
130                 135                 140

<210> SEQ ID NO 28
<211> LENGTH: 125
<212> TYPE: PRT
<213> ORGANISM: Artificial sequence
<220> FEATURE:
<223> OTHER INFORMATION: Rh5 antigenic fragment

<400> SEQUENCE: 28

Ile Ala Val Asp Ala Phe Ile Lys Lys Ile Asn Glu Thr Tyr Asp Lys
1               5                   10                  15
Val Lys Ser Lys Cys Asn Asp Ile Lys Asn Asp Leu Ile Ala Thr Ile
            20                  25                  30
Lys Lys Leu Glu His Pro Tyr Asp Ile Asn Asn Lys Asn Asp Asp Ser
        35                  40                  45
Tyr Arg Tyr Asp Ile Ser Glu Glu Ile Asp Asp Lys Ser Glu Glu Thr
50                  55                  60
Asp Asp Glu Thr Glu Glu Val Glu Asp Ser Ile Gln Asp Thr Asp Ser
65                  70                  75                  80
Asn His Thr Pro Ser Asn Lys Lys Asn Asp Leu Met Asn Arg Thr
                85                  90                  95
Phe Lys Lys Met Met Asp Glu Tyr Asn Thr Lys Lys Lys Leu Ile
            100                 105                 110
```

```
Lys Cys Ile Lys Asn His Glu Asn Asp Phe Asn Lys Ile
            115                 120                 125

<210> SEQ ID NO 29
<211> LENGTH: 12
<212> TYPE: PRT
<213> ORGANISM: Artificial Sequence
<220> FEATURE:
<223> OTHER INFORMATION: Tryptic peptide

<400> SEQUENCE: 29

Lys His Leu Ser Tyr Asn Ser Ile Tyr His Lys Ser
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Tryptic peptide

<400> SEQUENCE: 30

Lys Lys Ile Asn Glu Thr Tyr Asp Lys Val Lys Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Tryptic peptide

<400> SEQUENCE: 31

Lys Lys Leu Glu His Pro Tyr Asp Ile Asn Asn Lys Asn
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Tryptic peptide

<400> SEQUENCE: 32

Lys Met Met Asp Glu Tyr Asn Thr Lys Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Tryptic peptide

<400> SEQUENCE: 33

Arg Tyr His Tyr Asp Glu Tyr Ile His Lys Leu
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Tryptic peptide

<400> SEQUENCE: 34
```

```
Lys Ile Ile Gln Asp Lys Ile Lys Leu
1               5
```

```
<210> SEQ ID NO 35
<211> LENGTH: 1502
<212> TYPE: PRT
<213> ORGANISM: Plasmodium falciparum

<400> SEQUENCE: 35

Met Lys Cys Asn Ile Ser Ile Tyr Phe Phe Ala Ser Phe Phe Val Leu
1               5                   10                  15

Tyr Phe Ala Lys Ala Arg Asn Glu Tyr Asp Ile Lys Glu Asn Glu Lys
                20                  25                  30

Phe Leu Asp Val Tyr Lys Glu Lys Phe Asn Glu Leu Asp Lys Lys Lys
            35                  40                  45

Tyr Gly Asn Val Gln Lys Thr Asp Lys Lys Ile Phe Thr Phe Ile Glu
        50                  55                  60

Asn Lys Leu Asp Ile Leu Asn Asn Ser Lys Phe Asn Lys Arg Trp Lys
65                  70                  75                  80

Ser Tyr Gly Thr Pro Asp Asn Ile Asp Lys Asn Met Ser Leu Ile Asn
                85                  90                  95

Lys His Asn Asn Glu Glu Met Phe Asn Asn Tyr Gln Ser Phe Leu
                100                 105                 110

Ser Thr Ser Ser Leu Ile Lys Gln Asn Lys Tyr Val Pro Ile Asn Ala
            115                 120                 125

Val Arg Val Ser Arg Ile Leu Ser Phe Leu Asp Ser Arg Ile Asn Asn
        130                 135                 140

Gly Arg Asn Thr Ser Ser Asn Asn Glu Val Leu Ser Asn Cys Arg Glu
145                 150                 155                 160

Lys Arg Lys Gly Met Lys Trp Asp Cys Lys Lys Asn Asp Arg Ser
                165                 170                 175

Asn Tyr Val Cys Ile Pro Asp Arg Arg Ile Gln Leu Cys Ile Val Asn
                180                 185                 190

Leu Ser Ile Ile Lys Thr Tyr Thr Lys Glu Thr Met Lys Asp His Phe
            195                 200                 205

Ile Glu Ala Ser Lys Lys Glu Ser Gln Leu Leu Lys Lys Asn Asp
        210                 215                 220

Asn Lys Tyr Asn Ser Lys Phe Cys Asn Asp Leu Lys Asn Ser Phe Leu
225                 230                 235                 240

Asp Tyr Gly His Leu Ala Met Gly Asn Asp Met Asp Phe Gly Gly Tyr
                245                 250                 255

Ser Thr Lys Ala Glu Asn Lys Ile Gln Glu Val Phe Lys Gly Ala His
            260                 265                 270

Gly Glu Ile Ser Glu His Lys Ile Lys Asn Phe Arg Lys Lys Trp Trp
        275                 280                 285

Asn Glu Phe Arg Glu Lys Leu Trp Glu Ala Met Leu Ser Glu His Lys
    290                 295                 300

Asn Asn Ile Asn Asn Cys Lys Asn Ile Pro Gln Glu Glu Leu Gln Ile
305                 310                 315                 320

Thr Gln Trp Ile Lys Glu Trp His Gly Glu Phe Leu Leu Glu Arg Asp
                325                 330                 335

Asn Arg Ser Lys Leu Pro Lys Ser Lys Cys Lys Asn Asn Thr Leu Tyr
            340                 345                 350

Glu Ala Cys Glu Lys Glu Cys Ile Asp Pro Cys Met Lys Tyr Arg Asp
        355                 360                 365
```

```
Trp Ile Ile Arg Ser Lys Phe Glu Trp His Thr Leu Ser Lys Glu Tyr
    370                 375                 380

Glu Thr Gln Lys Val Pro Lys Glu Asn Ala Glu Asn Tyr Leu Ile Lys
385                 390                 395                 400

Ile Ser Glu Asn Lys Asn Asp Ala Lys Val Ser Leu Leu Asn Asn
                405                 410                 415

Cys Asp Ala Glu Tyr Ser Lys Tyr Cys Asp Cys Lys His Thr Thr Thr
                420                 425                 430

Leu Val Lys Ser Val Leu Asn Gly Asn Asp Asn Thr Ile Lys Glu Lys
            435                 440                 445

Arg Glu His Ile Asp Leu Asp Asp Phe Ser Lys Phe Gly Cys Asp Lys
    450                 455                 460

Asn Ser Val Asp Thr Asn Thr Lys Val Trp Glu Cys Lys Lys Pro Tyr
465                 470                 475                 480

Lys Leu Ser Thr Lys Asp Val Cys Val Pro Pro Arg Arg Gln Glu Leu
                485                 490                 495

Cys Leu Gly Asn Ile Asp Arg Ile Tyr Asp Lys Asn Leu Leu Met Ile
                500                 505                 510

Lys Glu His Ile Leu Ala Ile Ala Ile Tyr Glu Ser Arg Ile Leu Lys
            515                 520                 525

Arg Lys Tyr Lys Asn Lys Asp Asp Lys Glu Val Cys Lys Ile Ile Asn
    530                 535                 540

Lys Thr Phe Ala Asp Ile Arg Asp Ile Ile Gly Gly Thr Asp Tyr Trp
545                 550                 555                 560

Asn Asp Leu Ser Asn Arg Lys Leu Val Gly Lys Ile Asn Thr Asn Ser
                565                 570                 575

Asn Tyr Val His Arg Asn Lys Gln Asn Asp Lys Leu Phe Arg Asp Glu
            580                 585                 590

Trp Trp Lys Val Ile Lys Lys Asp Val Trp Asn Val Ile Ser Trp Val
    595                 600                 605

Phe Lys Asp Lys Thr Val Cys Lys Glu Asp Asp Ile Glu Asn Ile Pro
610                 615                 620

Gln Phe Phe Arg Trp Phe Ser Glu Trp Gly Asp Asp Tyr Cys Gln Asp
625                 630                 635                 640

Lys Thr Lys Met Ile Glu Thr Leu Lys Val Glu Cys Lys Glu Lys Pro
                645                 650                 655

Cys Glu Asp Asp Asn Cys Lys Arg Lys Cys Asn Ser Tyr Lys Glu Trp
                660                 665                 670

Ile Ser Lys Lys Lys Glu Glu Tyr Asn Lys Gln Ala Lys Gln Tyr Gln
            675                 680                 685

Glu Tyr Gln Lys Gly Asn Asn Tyr Lys Met Tyr Ser Glu Phe Lys Ser
    690                 695                 700

Ile Lys Pro Glu Val Tyr Leu Lys Lys Tyr Ser Glu Lys Cys Ser Asn
705                 710                 715                 720

Leu Asn Phe Glu Asp Glu Phe Lys Glu Glu Leu His Ser Asp Tyr Lys
                725                 730                 735

Asn Lys Cys Thr Met Cys Pro Glu Val Lys Asp Val Pro Ile Ser Ile
                740                 745                 750

Ile Arg Asn Asn Glu Gln Thr Ser Gln Glu Ala Val Pro Glu Glu Ser
            755                 760                 765

Thr Glu Ile Ala His Arg Thr Glu Thr Arg Thr Asp Glu Arg Lys Asn
    770                 775                 780
```

-continued

```
Gln Glu Pro Ala Asn Lys Asp Leu Lys Asn Pro Gln Gln Ser Val Gly
785                 790                 795                 800

Glu Asn Gly Thr Lys Asp Leu Leu Gln Glu Asp Leu Gly Gly Ser Arg
            805                 810                 815

Ser Glu Asp Glu Val Thr Gln Glu Phe Gly Val Asn His Gly Ile Pro
        820                 825                 830

Lys Gly Glu Asp Gln Thr Leu Gly Lys Ser Asp Ala Ile Pro Asn Ile
    835                 840                 845

Gly Glu Pro Glu Thr Gly Ile Ser Thr Thr Glu Glu Ser Arg His Glu
850                 855                 860

Glu Gly His Asn Lys Gln Ala Leu Ser Thr Ser Val Asp Glu Pro Glu
865                 870                 875                 880

Leu Ser Asp Thr Leu Gln Leu His Glu Asp Thr Lys Glu Asn Asp Lys
                885                 890                 895

Leu Pro Leu Glu Ser Ser Thr Ile Thr Ser Pro Thr Glu Ser Gly Ser
                900                 905                 910

Ser Asp Thr Glu Glu Thr Pro Ser Ile Ser Glu Gly Pro Lys Gly Asn
            915                 920                 925

Glu Gln Lys Lys Arg Asp Asp Ser Leu Ser Lys Ile Ser Val Ser
930                 935                 940

Pro Glu Asn Ser Arg Pro Glu Thr Asp Ala Lys Asp Thr Ser Asn Leu
945                 950                 955                 960

Leu Lys Leu Lys Gly Asp Val Asp Ile Ser Met Pro Lys Ala Val Ile
                965                 970                 975

Gly Ser Ser Pro Asn Asp Asn Ile Asn Val Thr Glu Gln Gly Asp Asn
            980                 985                 990

Ile Ser Gly Val Asn Ser Lys Pro Leu Ser Asp Asp Val Arg Pro Asp
        995                 1000                1005

Lys Asn His Glu Glu Val Lys Glu His Thr Ser Asn Ser Asp Asn
    1010                1015                1020

Val Gln Gln Ser Gly Gly Ile Val Asn Met Asn Val Glu Lys Glu
    1025                1030                1035

Leu Lys Asp Thr Leu Glu Asn Pro Ser Ser Ser Leu Asp Glu Gly
    1040                1045                1050

Lys Ala His Glu Glu Leu Ser Glu Pro Asn Leu Ser Ser Asp Gln
    1055                1060                1065

Asp Met Ser Asn Thr Pro Gly Pro Leu Asp Asn Thr Ser Glu Glu
    1070                1075                1080

Thr Thr Glu Arg Ile Ser Asn Asn Glu Tyr Lys Val Asn Glu Arg
    1085                1090                1095

Glu Gly Glu Arg Thr Leu Thr Lys Glu Tyr Glu Asp Ile Val Leu
    1100                1105                1110

Lys Ser His Met Asn Arg Glu Ser Asp Asp Gly Glu Leu Tyr Asp
    1115                1120                1125

Glu Asn Ser Asp Leu Ser Thr Val Asn Asp Glu Ser Glu Asp Ala
    1130                1135                1140

Glu Ala Lys Met Lys Gly Asn Asp Thr Ser Glu Met Ser His Asn
    1145                1150                1155

Ser Ser Gln His Ile Glu Ser Asp Gln Gln Lys Asn Asp Met Lys
    1160                1165                1170

Thr Val Gly Asp Leu Gly Thr His Val Gln Asn Glu Ile Ser
    1175                1180                1185

Val Pro Val Thr Gly Glu Ile Asp Glu Lys Leu Arg Glu Ser Lys
```

Glu Ser Lys Ile His Lys Ala Glu Glu Glu Arg Leu Ser His Thr
1205                1210                1215

Asp Ile His Lys Ile Asn Pro Glu Asp Arg Asn Ser Asn Thr Leu
1220                1225                1230

His Leu Lys Asp Ile Arg Asn Glu Glu Asn Glu Arg His Leu Thr
1235                1240                1245

Asn Gln Asn Ile Asn Ile Ser Gln Glu Arg Asp Leu Gln Lys His
1250                1255                1260

Gly Phe His Thr Met Asn Asn Leu His Gly Asp Gly Val Ser Glu
1265                1270                1275

Arg Ser Gln Ile Asn His Ser His His Gly Asn Arg Gln Asp Arg
1280                1285                1290

Gly Gly Asn Ser Gly Asn Val Leu Asn Met Arg Ser Asn Asn Asn
1295                1300                1305

Asn Phe Asn Asn Ile Pro Ser Arg Tyr Asn Leu Tyr Asp Lys Lys
1310                1315                1320

Leu Asp Leu Asp Leu Tyr Glu Asn Arg Asn Asp Ser Thr Thr Lys
1325                1330                1335

Glu Leu Ile Lys Lys Leu Ala Glu Ile Asn Lys Cys Glu Asn Glu
1340                1345                1350

Ile Ser Val Lys Tyr Cys Asp His Met Ile His Glu Glu Ile Pro
1355                1360                1365

Leu Lys Thr Cys Thr Lys Glu Lys Thr Arg Asn Leu Cys Cys Ala
1370                1375                1380

Val Ser Asp Tyr Cys Met Ser Tyr Phe Thr Tyr Asp Ser Glu Glu
1385                1390                1395

Tyr Tyr Asn Cys Thr Lys Arg Glu Phe Asp Pro Ser Tyr Thr
1400                1405                1410

Cys Phe Arg Lys Glu Ala Phe Ser Ser Met Pro Tyr Tyr Ala Gly
1415                1420                1425

Ala Gly Val Leu Phe Ile Ile Leu Val Ile Leu Gly Ala Ser Gln
1430                1435                1440

Ala Lys Tyr Gln Ser Ser Glu Gly Val Met Asn Glu Asn Asn Glu
1445                1450                1455

Asn Asn Phe Leu Phe Glu Val Thr Asp Asn Leu Asp Lys Leu Ser
1460                1465                1470

Asn Met Phe Asn Gln Gln Val Gln Glu Thr Asn Ile Asn Asp Phe
1475                1480                1485

Ser Glu Tyr His Glu Asp Ile Asn Asp Ile Asn Phe Lys Lys
1490                1495                1500

<210> SEQ ID NO 36
<211> LENGTH: 512
<212> TYPE: PRT
<213> ORGANISM: Artificial Sequence
<220> FEATURE:
<223> OTHER INFORMATION: EBA175 antigenic fragment

<400> SEQUENCE: 36

Ser Gln Glu Ala Val Pro Glu Glu Ser Thr Glu Ile Ala His Arg Thr
1               5                   10                  15

Glu Thr Arg Thr Asp Glu Arg Lys Asn Gln Glu Pro Ala Asn Lys Asp
            20                  25                  30

Leu Lys Asn Pro Gln Gln Ser Val Gly Glu Asn Gly Thr Lys Asp Leu

```
            35                  40                  45
Leu Gln Glu Asp Leu Gly Gly Ser Arg Ser Glu Asp Glu Val Thr Gln
 50                  55                  60

Glu Phe Gly Val Asn His Gly Ile Pro Lys Gly Asp Gln Thr Leu
 65                  70                  75                  80

Gly Lys Ser Asp Ala Ile Pro Asn Ile Gly Pro Glu Thr Gly Ile
                     85                  90                  95

Ser Thr Thr Glu Glu Ser Arg His Glu Gly His Asn Lys Gln Ala
                    100                 105                 110

Leu Ser Thr Ser Val Asp Glu Pro Glu Leu Ser Asp Thr Leu Gln Leu
                115                 120                 125

His Glu Asp Thr Lys Glu Asn Asp Lys Leu Pro Leu Glu Ser Ser Thr
                130                 135                 140

Ile Thr Ser Pro Thr Glu Ser Gly Ser Ser Asp Thr Glu Glu Thr Pro
145                 150                 155                 160

Ser Ile Ser Glu Gly Pro Lys Gly Asn Glu Gln Lys Lys Arg Asp Asp
                    165                 170                 175

Asp Ser Leu Ser Lys Ile Ser Val Ser Pro Glu Asn Ser Arg Pro Glu
                180                 185                 190

Thr Asp Ala Lys Asp Thr Ser Asn Leu Leu Lys Leu Lys Gly Asp Val
                195                 200                 205

Asp Ile Ser Met Pro Lys Ala Val Ile Gly Ser Ser Pro Asn Asp Asn
210                 215                 220

Ile Asn Val Thr Glu Gln Gly Asp Asn Ile Ser Gly Val Asn Ser Lys
225                 230                 235                 240

Pro Leu Ser Asp Asp Val Arg Pro Asp Lys Asn His Glu Glu Val Lys
                245                 250                 255

Glu His Thr Ser Asn Ser Asp Asn Val Gln Gln Ser Gly Gly Ile Val
                260                 265                 270

Asn Met Asn Val Glu Lys Glu Leu Lys Asp Thr Leu Glu Asn Pro Ser
            275                 280                 285

Ser Ser Leu Asp Glu Gly Lys Ala His Glu Glu Leu Ser Glu Pro Asn
            290                 295                 300

Leu Ser Ser Asp Gln Asp Met Ser Asn Thr Pro Gly Pro Leu Asp Asn
305                 310                 315                 320

Thr Ser Glu Glu Thr Thr Glu Arg Ile Ser Asn Asn Glu Tyr Lys Val
                325                 330                 335

Asn Glu Arg Glu Gly Glu Arg Thr Leu Thr Lys Glu Tyr Glu Asp Ile
                340                 345                 350

Val Leu Lys Ser His Met Asn Arg Glu Ser Asp Asp Gly Glu Leu Tyr
                355                 360                 365

Asp Glu Asn Ser Asp Leu Ser Thr Val Asn Asp Glu Ser Glu Asp Ala
                370                 375                 380

Glu Ala Lys Met Lys Gly Asn Asp Thr Ser Glu Met Ser His Asn Ser
385                 390                 395                 400

Ser Gln His Ile Glu Ser Asp Gln Gln Lys Asn Asp Met Lys Thr Val
                    405                 410                 415

Gly Asp Leu Gly Thr Thr His Val Gln Asn Glu Ile Ser Val Pro Val
                420                 425                 430

Thr Gly Glu Ile Asp Glu Lys Leu Arg Glu Ser Lys Glu Ser Lys Ile
                435                 440                 445

His Lys Ala Glu Glu Glu Arg Leu Ser His Thr Asp Ile His Lys Ile
                450                 455                 460
```

Asn Pro Glu Asp Arg Asn Ser Asn Thr Leu His Leu Lys Asp Ile Arg
465                 470                 475                 480

Asn Glu Glu Asn Glu Arg His Leu Thr Asn Gln Asn Ile Asn Ile Ser
            485                 490                 495

Gln Glu Arg Asp Leu Gln Lys His Gly Phe His Thr Met Asn Asn Leu
        500                 505                 510

<210> SEQ ID NO 37
<211> LENGTH: 1567
<212> TYPE: PRT
<213> ORGANISM: Plasmodium falciparum

<400> SEQUENCE: 37

Met Lys Gly Lys Met Asn Met Cys Leu Phe Phe Tyr Ser Ile Leu
1               5                   10                  15

Tyr Val Val Leu Cys Thr Tyr Val Leu Gly Ile Ser Glu Glu Tyr Leu
            20                  25                  30

Lys Glu Arg Pro Gln Gly Leu Asn Val Glu Thr Asn Asn Asn Asn
        35                  40                  45

Asn Asn Asn Asn Asn Ser Asn Ser Asn Asp Ala Met Ser Phe Val
50                  55                  60

Asn Glu Val Ile Arg Phe Ile Glu Asn Glu Lys Asp Asp Lys Glu Asp
65                  70                  75                  80

Lys Lys Val Lys Ile Ile Ser Arg Pro Val Glu Asn Thr Leu His Arg
            85                  90                  95

Tyr Pro Val Ser Ser Phe Leu Asn Ile Lys Lys Tyr Gly Arg Lys Gly
            100                 105                 110

Glu Tyr Leu Asn Arg Asn Ser Phe Val Gln Arg Ser Tyr Ile Arg Gly
        115                 120                 125

Cys Lys Gly Lys Arg Ser Thr His Thr Trp Ile Cys Glu Asn Lys Gly
130                 135                 140

Asn Asn Asn Ile Cys Ile Pro Asp Arg Arg Val Gln Leu Cys Ile Thr
145                 150                 155                 160

Ala Leu Gln Asp Leu Lys Asn Ser Gly Ser Glu Thr Thr Asp Arg Lys
            165                 170                 175

Leu Leu Arg Asp Lys Val Phe Asp Ser Ala Met Tyr Glu Thr Asp Leu
        180                 185                 190

Leu Trp Asn Lys Tyr Gly Phe Arg Gly Phe Asp Asp Phe Cys Asp Asp
    195                 200                 205

Val Lys Asn Ser Tyr Leu Asp Tyr Lys Asp Val Ile Phe Gly Thr Asp
210                 215                 220

Leu Asp Lys Asn Ile Ser Lys Leu Val Glu Glu Ser Leu Lys Arg
225                 230                 235                 240

Phe Phe Lys Lys Asp Ser Ser Val Leu Asn Pro Thr Ala Trp Trp Arg
            245                 250                 255

Arg Tyr Gly Thr Arg Leu Trp Lys Thr Met Ile Gln Pro Tyr Ala His
        260                 265                 270

Leu Gly Cys Arg Lys Pro Asp Glu Asn Glu Pro Gln Ile Asn Arg Trp
    275                 280                 285

Ile Leu Glu Trp Gly Lys Tyr Asn Cys Arg Leu Met Lys Glu Lys Glu
    290                 295                 300

Lys Leu Leu Thr Gly Glu Cys Ser Val Asn Arg Lys Lys Ser Asp Cys
305                 310                 315                 320

Ser Thr Gly Cys Asn Asn Glu Cys Tyr Thr Tyr Arg Ser Leu Ile Asn

```
                      325                 330                 335
Arg Gln Arg Tyr Glu Val Ser Ile Leu Gly Lys Lys Tyr Ile Lys Val
            340                 345                 350
Val Arg Tyr Thr Ile Phe Arg Arg Lys Ile Val Gln Pro Asp Asn Ala
            355                 360                 365
Leu Asp Phe Leu Lys Leu Asn Cys Ser Glu Cys Lys Asp Ile Asp Phe
            370                 375                 380
Lys Pro Phe Phe Glu Phe Glu Tyr Gly Lys Tyr Glu Glu Lys Cys Met
385                 390                 395                 400
Cys Gln Ser Tyr Ile Asp Leu Lys Ile Gln Phe Lys Asn Asn Asp Ile
                405                 410                 415
Cys Ser Phe Asn Ala Gln Thr Asp Thr Val Ser Ser Asp Lys Arg Phe
                420                 425                 430
Cys Leu Glu Lys Lys Glu Phe Lys Pro Trp Lys Cys Asp Lys Asn Ser
                435                 440                 445
Phe Glu Thr Val His His Lys Gly Val Cys Val Ser Pro Arg Arg Gln
                450                 455                 460
Gly Phe Cys Leu Gly Asn Leu Asn Tyr Leu Leu Asn Asp Asp Ile Tyr
465                 470                 475                 480
Asn Val His Asn Ser Gln Leu Leu Ile Glu Ile Ile Met Ala Ser Lys
                485                 490                 495
Gln Glu Gly Lys Leu Leu Trp Lys Lys His Gly Thr Ile Leu Asp Asn
                500                 505                 510
Gln Asn Ala Cys Lys Tyr Ile Asn Asp Ser Tyr Val Asp Tyr Lys Asp
                515                 520                 525
Ile Val Ile Gly Asn Asp Leu Trp Asn Asp Asn Ser Ile Lys Val
                530                 535                 540
Gln Asn Asn Leu Asn Leu Ile Phe Glu Arg Asn Phe Gly Tyr Lys Val
545                 550                 555                 560
Gly Arg Asn Lys Leu Phe Lys Thr Ile Lys Glu Leu Lys Asn Val Trp
                565                 570                 575
Trp Ile Leu Asn Arg Asn Lys Val Trp Glu Ser Met Arg Cys Gly Ile
                580                 585                 590
Asp Glu Val Asp Gln Arg Arg Lys Thr Cys Glu Arg Ile Asp Glu Leu
                595                 600                 605
Glu Asn Met Pro Gln Phe Phe Arg Trp Phe Ser Gln Trp Ala His Phe
                610                 615                 620
Phe Cys Lys Glu Lys Glu Tyr Trp Glu Leu Lys Leu Asn Asp Lys Cys
625                 630                 635                 640
Thr Gly Asn Asn Gly Lys Ser Leu Cys Gln Asp Lys Thr Cys Gln Asn
                645                 650                 655
Val Cys Thr Asn Met Asn Tyr Trp Thr Tyr Thr Arg Lys Leu Ala Tyr
                660                 665                 670
Glu Ile Gln Ser Val Lys Tyr Asp Lys Asp Arg Lys Leu Phe Ser Leu
                675                 680                 685
Ala Lys Asp Lys Asn Val Thr Thr Phe Leu Lys Glu Asn Ala Lys Asn
                690                 695                 700
Cys Ser Asn Ile Asp Phe Thr Lys Ile Phe Asp Gln Leu Asp Lys Leu
705                 710                 715                 720
Phe Lys Glu Arg Cys Ser Cys Met Asp Thr Gln Val Leu Glu Val Lys
                725                 730                 735
Asn Lys Glu Met Leu Ser Ile Asp Ser Asn Ser Glu Asp Ala Thr Asp
                740                 745                 750
```

-continued

```
Ile Ser Glu Lys Asn Gly Glu Glu Leu Tyr Val Asn His Asn Ser
        755                 760                 765

Val Ser Val Ala Ser Gly Asn Lys Glu Ile Glu Lys Ser Lys Asp Glu
    770                 775                 780

Lys Gln Pro Glu Lys Glu Ala Lys Gln Thr Asn Gly Thr Leu Thr Val
785                 790                 795                 800

Arg Thr Asp Lys Asp Ser Asp Arg Asn Lys Gly Lys Asp Thr Ala Thr
                805                 810                 815

Asp Thr Lys Asn Ser Pro Glu Asn Leu Lys Val Gln Glu His Gly Thr
            820                 825                 830

Asn Gly Glu Thr Ile Lys Glu Pro Pro Lys Leu Pro Glu Ser Ser
        835                 840                 845

Glu Thr Leu Gln Ser Gln Glu Gln Leu Glu Ala Glu Ala Gln Lys Gln
    850                 855                 860

Lys Gln Glu Glu Glu Pro Lys Lys Lys Gln Glu Glu Pro Lys Lys
865                 870                 875                 880

Lys Gln Glu Glu Glu Gln Lys Arg Glu Gln Glu Gln Lys Gln Glu Gln
                885                 890                 895

Glu Glu Glu Glu Gln Lys Gln Glu Glu Gln Gln Ile Gln Asp Gln
            900                 905                 910

Ser Gln Ser Gly Leu Asp Gln Ser Ser Lys Val Gly Val Ala Ser Glu
    915                 920                 925

Gln Asn Glu Ile Ser Ser Gly Gln Glu Gln Asn Val Lys Ser Ser Ser
930                 935                 940

Pro Glu Val Val Pro Gln Thr Thr Ser Glu Asn Gly Ser Ser Gln
945                 950                 955                 960

Asp Thr Lys Ile Ser Ser Thr Glu Pro Asn Glu Asn Ser Val Val Asp
                965                 970                 975

Arg Ala Thr Asp Ser Met Asn Leu Asp Pro Glu Lys Val His Asn Glu
            980                 985                 990

Asn Met Ser Asp Pro Asn Thr Asn  Thr Glu Pro Asp Ala  Ser Leu Lys
    995                 1000                1005

Asp Asp  Lys Lys Glu Val Asp  Ala Lys Lys Glu  Leu Gln Ser
    1010                1015                1020

Thr Val  Ser Arg Ile Glu Ser  Asn Glu Gln Asp Val  Gln Ser Thr
    1025                1030                1035

Pro Pro  Glu Asp Thr Pro  Thr Val Glu Gly Lys Val  Gly Asp Lys
    1040                1045                1050

Ala Glu  Met Leu Thr Ser Pro  His Ala Thr Asp Asn  Ser Glu Ser
    1055                1060                1065

Glu Ser  Gly Leu Asn Pro Thr  Asp Asp Ile Lys Thr  Thr Asp Gly
    1070                1075                1080

Val Val  Lys Glu Gln Glu Ile  Leu Gly Gly Gly Glu  Ser Ala Thr
    1085                1090                1095

Glu Thr  Ser Lys Ser Asn Leu  Glu Lys Pro Lys Asp  Val Glu Pro
    1100                1105                1110

Ser His  Glu Ile Ser Glu Pro  Val Leu Ser Gly Thr  Thr Gly Lys
    1115                1120                1125

Glu Glu  Ser Glu Leu Leu Lys  Ser Lys Ser Ile Glu  Thr Lys Gly
    1130                1135                1140

Glu Thr  Asp Pro Arg Ser Asn  Asp Gln Glu Asp Ala  Thr Asp Asp
    1145                1150                1155
```

```
Val Val Glu Asn Ser Arg Asp Asp Asn Asn Ser Leu Ser Asn Ser
    1160                1165                1170

Val Asp Asn Gln Ser Asn Val Leu Asn Arg Glu Asp Pro Ile Ala
    1175                1180                1185

Ser Glu Thr Glu Val Val Ser Glu Pro Glu Asp Ser Ser Arg Ile
    1190                1195                1200

Ile Thr Thr Glu Val Pro Ser Thr Thr Val Lys Pro Pro Asp Glu
    1205                1210                1215

Lys Arg Ser Glu Glu Val Gly Glu Lys Glu Ala Lys Glu Ile Lys
    1220                1225                1230

Val Glu Pro Val Val Pro Arg Ala Ile Gly Glu Pro Met Glu Asn
    1235                1240                1245

Ser Val Ser Val Gln Ser Pro Pro Asn Val Glu Asp Val Glu Lys
    1250                1255                1260

Glu Thr Leu Ile Ser Glu Asn Asn Gly Leu His Asn Asp Thr His
    1265                1270                1275

Arg Gly Asn Ile Ser Glu Lys Asp Leu Ile Asp Ile His Leu Leu
    1280                1285                1290

Arg Asn Glu Ala Gly Ser Thr Ile Leu Asp Asp Ser Arg Arg Asn
    1295                1300                1305

Gly Glu Met Thr Glu Gly Ser Glu Ser Asp Val Gly Glu Leu Gln
    1310                1315                1320

Glu His Asn Phe Ser Thr Gln Gln Lys Asp Glu Lys Asp Phe Asp
    1325                1330                1335

Gln Ile Ala Ser Asp Arg Glu Lys Glu Glu Ile Gln Lys Leu Leu
    1340                1345                1350

Asn Ile Gly His Glu Glu Asp Glu Asp Val Leu Lys Met Asp Arg
    1355                1360                1365

Thr Glu Asp Ser Met Ser Asp Gly Val Asn Ser His Leu Tyr Tyr
    1370                1375                1380

Asn Asn Leu Ser Ser Glu Glu Lys Met Glu Gln Tyr Asn Asn Arg
    1385                1390                1395

Asp Ala Ser Lys Asp Arg Glu Glu Ile Leu Asn Arg Ser Asn Thr
    1400                1405                1410

Asn Thr Cys Ser Asn Glu His Ser Leu Lys Tyr Cys Gln Tyr Met
    1415                1420                1425

Glu Arg Asn Lys Asp Leu Leu Glu Thr Cys Ser Glu Asp Lys Arg
    1430                1435                1440

Leu His Leu Cys Cys Glu Ile Ser Asp Tyr Cys Leu Lys Phe Phe
    1445                1450                1455

Asn Pro Lys Ser Ile Glu Tyr Phe Asp Cys Thr Gln Lys Glu Phe
    1460                1465                1470

Asp Asp Pro Thr Tyr Asn Cys Phe Arg Lys Gln Arg Phe Thr Ser
    1475                1480                1485

Met His Tyr Ile Ala Gly Gly Ile Ile Ala Leu Leu Leu Phe
    1490                1495                1500

Ile Leu Gly Ser Ala Ser Tyr Arg Lys Asn Leu Asp Asp Glu Lys
    1505                1510                1515

Gly Phe Tyr Asp Ser Asn Leu Asn Asp Ser Ala Phe Glu Tyr Asn
    1520                1525                1530

Asn Asn Lys Tyr Asn Lys Leu Pro Tyr Met Phe Asp Gln Gln Ile
    1535                1540                1545

Asn Val Val Asn Ser Asp Leu Tyr Ser Glu Gly Ile Tyr Asp Asp
```

Thr Thr Thr Phe
    1565

<210> SEQ ID NO 38
<211> LENGTH: 1210
<212> TYPE: PRT
<213> ORGANISM: Plasmodium falciparum

<400> SEQUENCE: 38

Met Lys Gly Tyr Phe Asn Ile Tyr Phe Leu Ile Pro Leu Ile Phe Leu
1               5                   10                  15

Tyr Asn Val Ile Arg Ile Asn Glu Ser Ile Ile Gly Arg Thr Leu Tyr
            20                  25                  30

Asn Arg Gln Asp Glu Ser Ser Asp Ile Ser Arg Val Asn Ser Pro Glu
        35                  40                  45

Leu Asn Asn Asn His Lys Thr Asn Ile Tyr Asp Ser Asp Tyr Glu Asp
    50                  55                  60

Val Asn Asn Lys Leu Ile Asn Ser Phe Val Glu Asn Lys Ser Val Lys
65                  70                  75                  80

Lys Lys Arg Ser Leu Ser Phe Ile Asn Asn Lys Thr Lys Ser Tyr Asp
                85                  90                  95

Ile Ile Pro Pro Ser Tyr Ser Tyr Arg Asn Asp Lys Phe Asn Ser Leu
            100                 105                 110

Ser Glu Asn Glu Asp Asn Ser Gly Asn Thr Asn Ser Asn Asn Phe Ala
        115                 120                 125

Asn Thr Ser Glu Ile Ser Ile Gly Lys Asp Asn Lys Gln Tyr Thr Phe
    130                 135                 140

Ile Gln Lys Arg Thr His Leu Phe Ala Cys Gly Ile Lys Arg Lys Ser
145                 150                 155                 160

Ile Lys Trp Ile Cys Arg Glu Asn Ser Glu Lys Ile Thr Val Cys Val
                165                 170                 175

Pro Asp Arg Lys Ile Gln Leu Cys Ile Ala Asn Phe Leu Asn Ser Arg
            180                 185                 190

Leu Glu Thr Met Glu Lys Phe Lys Glu Ile Phe Leu Ile Ser Val Asn
        195                 200                 205

Thr Glu Ala Lys Leu Leu Tyr Asn Lys Asn Glu Gly Lys Asp Pro Ser
    210                 215                 220

Ile Phe Cys Asn Glu Leu Arg Asn Ser Phe Ser Asp Phe Arg Asn Ser
225                 230                 235                 240

Phe Ile Gly Asp Asp Met Asp Phe Gly Gly Asn Thr Asp Arg Val Lys
                245                 250                 255

Gly Tyr Ile Asn Lys Lys Phe Ser Asp Tyr Tyr Lys Glu Lys Asn Val
            260                 265                 270

Glu Lys Leu Asn Asn Ile Lys Lys Glu Trp Trp Glu Lys Asn Lys Ala
        275                 280                 285

Asn Leu Trp Asn His Met Ile Val Asn His Lys Gly Asn Ile Ser Lys
    290                 295                 300

Glu Cys Ala Ile Ile Pro Ala Glu Glu Pro Gln Ile Asn Leu Trp Ile
305                 310                 315                 320

Lys Glu Trp Asn Glu Asn Phe Leu Met Glu Lys Lys Arg Leu Phe Leu
                325                 330                 335

Asn Ile Lys Asp Lys Cys Val Glu Asn Lys Lys Tyr Glu Ala Cys Phe
            340                 345                 350

-continued

Gly Gly Cys Arg Leu Pro Cys Ser Ser Tyr Thr Ser Phe Met Lys Lys
            355                 360                 365

Ser Lys Thr Gln Met Glu Val Leu Thr Asn Leu Tyr Lys Lys Lys Asn
    370                 375                 380

Ser Gly Val Asp Lys Asn Asn Phe Leu Asn Asp Leu Phe Lys Lys Asn
385                 390                 395                 400

Asn Lys Asn Asp Leu Asp Asp Phe Phe Lys Asn Glu Lys Glu Tyr Asp
                405                 410                 415

Asp Leu Cys Asp Cys Arg Tyr Thr Ala Thr Ile Ile Lys Ser Phe Leu
            420                 425                 430

Asn Gly Pro Ala Lys Asn Asp Val Asp Ile Ala Ser Gln Ile Asn Val
            435                 440                 445

Asn Asp Leu Arg Gly Phe Gly Cys Asn Tyr Lys Ser Asn Asn Glu Lys
    450                 455                 460

Ser Trp Asn Cys Thr Gly Thr Phe Thr Asn Lys Phe Pro Gly Thr Cys
465                 470                 475                 480

Glu Pro Pro Arg Arg Gln Thr Leu Cys Leu Gly Arg Thr Tyr Leu Leu
                485                 490                 495

His Arg Gly His Glu Glu Asp Tyr Lys Glu His Leu Leu Gly Ala Ser
            500                 505                 510

Ile Tyr Glu Ala Gln Leu Leu Lys Tyr Lys Tyr Lys Glu Lys Asp Glu
            515                 520                 525

Asn Ala Leu Cys Ser Ile Ile Gln Asn Ser Tyr Ala Asp Leu Ala Asp
            530                 535                 540

Ile Ile Lys Gly Ser Asp Ile Ile Lys Asp Tyr Tyr Gly Lys Lys Met
545                 550                 555                 560

Glu Glu Asn Leu Asn Lys Val Asn Lys Asp Lys Lys Arg Asn Glu Glu
                565                 570                 575

Ser Leu Lys Ile Phe Arg Glu Lys Trp Trp Asp Glu Asn Lys Glu Asn
            580                 585                 590

Val Trp Lys Val Met Ser Ala Val Leu Lys Asn Lys Glu Thr Cys Lys
            595                 600                 605

Asp Tyr Asp Lys Phe Gln Lys Ile Pro Gln Phe Leu Arg Trp Phe Lys
    610                 615                 620

Glu Trp Gly Asp Asp Phe Cys Glu Lys Arg Lys Glu Lys Ile Tyr Ser
625                 630                 635                 640

Phe Glu Ser Phe Lys Val Glu Cys Lys Lys Asp Cys Asp Glu Asn
                645                 650                 655

Thr Cys Lys Asn Lys Cys Ser Tyr Lys Lys Trp Ile Asp Leu Lys
            660                 665                 670

Lys Ser Glu Tyr Glu Lys Gln Val Asp Lys Tyr Thr Lys Asp Lys Asn
    675                 680                 685

Lys Lys Met Tyr Asp Asn Ile Asp Glu Val Lys Asn Lys Glu Ala Asn
    690                 695                 700

Val Tyr Leu Lys Glu Lys Ser Lys Glu Cys Lys Asp Val Asn Phe Asp
705                 710                 715                 720

Asp Lys Ile Phe Asn Glu Ser Pro Asn Glu Tyr Glu Asp Met Cys Lys
                725                 730                 735

Lys Cys Asp Glu Ile Lys Tyr Leu Asn Glu Ile Lys Tyr Pro Lys Thr
            740                 745                 750

Lys His Asp Ile Tyr Asp Ile Asp Thr Phe Ser Asp Thr Phe Gly Asp
            755                 760                 765

Gly Thr Pro Ile Ser Ile Asn Ala Asn Ile Asn Glu Gln Gln Ser Gly

```
              770                 775                 780
Lys Asp Thr Ser Asn Thr Gly Asn Ser Glu Thr Ser Asp Ser Pro Val
785                 790                 795                 800

Ser His Glu Pro Glu Ser Asp Ala Ala Ile Asn Val Glu Lys Leu Ser
                    805                 810                 815

Gly Asp Glu Ser Ser Glu Thr Arg Gly Ile Leu Asp Ile Asn Asp
                    820                 825                 830

Pro Ser Val Thr Asn Asn Val Asn Glu Val His Asp Ala Ser Asn Thr
                835                 840                 845

Gln Gly Ser Val Ser Asn Thr Ser Asp Ile Thr Asn Gly His Ser Glu
850                 855                 860

Ser Ser Leu Asn Arg Thr Thr Asn Ala Gln Asp Ile Lys Ile Gly Arg
865                 870                 875                 880

Ser Gly Asn Glu Gln Ser Asp Asn Gln Glu Asn Ser Ser His Ser Ser
                    885                 890                 895

Asp Asn Ser Gly Ser Leu Thr Ile Gly Gln Val Pro Ser Glu Asp Asn
                900                 905                 910

Thr Gln Asn Thr Tyr Asp Ser Gln Asn Pro His Arg Asp Thr Pro Asn
                915                 920                 925

Ala Leu Ala Ser Leu Pro Ser Asp Lys Ile Asn Glu Ile Glu Gly
                930                 935                 940

Phe Asp Ser Ser Arg Asp Ser Glu Asn Gly Arg Gly Asp Thr Thr Ser
945                 950                 955                 960

Asn Thr His Asp Val Arg Arg Thr Asn Ile Val Ser Glu Arg Val
                    965                 970                 975

Asn Ser His Asp Phe Ile Arg Asn Gly Met Ala Asn Asn Ala His
                980                 985                 990

His Gln Tyr Ile Thr Gln Ile Glu  Asn Asn Gly Ile Ile  Arg Gly Gln
                995                 1000                1005

Glu Glu  Ser Ala Gly Asn Ser  Val Asn Tyr Lys Asp  Asn Pro Lys
1010                1015                1020

Arg Ser  Asn Phe Ser Ser Glu  Asn Asp His Lys Lys  Asn Ile Gln
1025                1030                1035

Glu Tyr  Asn Ser Arg Asp Thr  Lys Arg Val Arg Glu  Glu Ile Ile
1040                1045                1050

Lys Leu  Ser Lys Gln Asn Lys  Cys Asn Asn Glu Tyr  Ser Met Glu
1055                1060                1065

Tyr Cys  Thr Tyr Ser Asp Glu  Arg Asn Ser Ser Pro  Gly Pro Cys
1070                1075                1080

Ser Arg  Glu Glu Arg Lys Lys  Leu Cys Cys Gln Ile  Ser Asp Tyr
1085                1090                1095

Cys Leu  Lys Tyr Phe Asn Phe  Tyr Ser Ile Glu Tyr  Tyr Asn Cys
1100                1105                1110

Ile Lys  Ser Glu Ile Lys Ser  Pro Glu Tyr Lys Cys  Phe Lys Ser
1115                1120                1125

Glu Gly  Gln Ser Ser Ile Pro  Tyr Phe Ala Ala Gly  Gly Ile Leu
1130                1135                1140

Val Val  Ile Val Leu Leu Leu  Ser Ser Ala Ser Arg  Met Gly Lys
1145                1150                1155

Ser Asn  Glu Glu Tyr Asp Ile  Gly Glu Ser Asn Ile  Glu Ala Thr
1160                1165                1170

Phe Glu  Glu Asn Asn Tyr Leu  Asn Lys Leu Ser Arg  Ile Phe Asn
1175                1180                1185
```

```
Gln Glu Val Gln Glu Thr Asn Ile Ser Asp Tyr Ser Glu Tyr Asn
    1190            1195                1200
Tyr Asn Glu Lys Asn Met Tyr
    1205            1210
```

<210> SEQ ID NO 39
<211> LENGTH: 1482
<212> TYPE: DNA
<213> ORGANISM: Artificial Sequence
<220> FEATURE:
<223> OTHER INFORMATION: Codon optimised sequence

<400> SEQUENCE: 39

```
ggtacccata tgaaaagcta ttgcaatgat ctgagcgaat gcgatattgg cctgatttat     60
catttcgata cctattgcat caatgatcag tacctgtttg tgagctatag ctgtagcaat    120
ctgtgcaata atgccataa taatagcacc tgttatggca atcgctttaa ttatgattgc    180
ttttgcgata atccgtatat tagcaaatat ggcaataaac tgtgcgaacg tccgaatgat    240
tgtgaaagcg ttctgtgtag ccagaatcag gtttgtcaga ttctgccgaa tgataaactg    300
atttgtcagt gcgaagaagg ctataaaaac gttaaaggta atgcgtgcc ggataataaa     360
tgtgatctga gctgtccgag caataaagtt tgcgttattg aaaatggcaa acagacctgt    420
aaatgcagcg aacgttttgt tctggaaaat ggtgtttgca tttgcgccaa tgattataaa    480
atggaagatg gcatcaattg cattgccaaa ataaatgca acgcaaaga gtatgaaaat     540
atttgcacca atccgaatga atgtgcgcc tataatgaag aaaccgatat tgtgaaatgc    600
gaatgcaaag aacattatta tcgtagcagc cgtggtgaat gcattctgaa tgattattgc    660
aaagacatca attgcaaaga aatgaagaa tgcagcattg tgaattttaa accggaatgc    720
gtgtgcaaag aaaatctgaa aaaaataac aaaggcgagt gcatttatga aaattcatgc    780
ctgattaatg aaggcaattg cccgaaagat agcaaatgca tttatcgcga atataaaccg    840
catgaatgcg tttgcaataa acagggtcat gttgccgtta atggtaaatg tgtgctggaa    900
gataaatgcg tgcataataa aaaatgtagc gaaaattcca tttgcgtgaa tgtgatgaat    960
aaagaaccga tttgcgtgtg cacctataat tattataaaa aagatggcgt gtgcctgatt   1020
cagaatccgt gtctgaaaga taatggtggt tgtagccgta atagcgaatg cacctttaaa   1080
tattccaaaa ttaattgtac ctgtaaagag aactacaaaa caaagatga tagctgcgtg   1140
ccgaatacca tgaatatga tgaaagcttt acctttcagt ataatgatga tgccagcatt   1200
attctgggtg catgtggtat gattgaattt agctatatct acaaccagat tatctggaaa   1260
attaataata gcaaagagag ctacgttttc tattatgatt atccgaccgc aggcaatatt   1320
gaagtgcaga ttaaaaacga aattttccac accattatct acctgaaaaa aaaaattggc   1380
aatagcgtga tttatgatga ttttcaggtg gatcatcaga cctgtattta tgaaaatgtg   1440
ttctattaca gcaatcagaa ttaaggatcc ctcgaggagc tc                      1482
```

<210> SEQ ID NO 40
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 40

```
cgctagccat atgaatgaag aaacagatat tgtaaaatg                           39
```

<210> SEQ ID NO 41
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 41
cgaggatccc taatcttcta aaacacattt tcc                           33

<210> SEQ ID NO 42
<211> LENGTH: 336
<212> TYPE: DNA
<213> ORGANISM: Artificial Sequence
<220> FEATURE:
<223> OTHER INFORMATION: coding sequence of rRh2-15 fragment

<400> SEQUENCE: 42
aaaaaatatg aaacatatgt agatatgaaa acaattgaat ctaaatatac aacagtaatg    60
actctatcag aacatttatt agaatatgca atggatgttt aaaagctaa ccctcaaaaa    120 cctattgatc aaaagcaaa tctggattca gaagtagtaa aattacaaat aaaaataaat    180
gagaaatcaa atgaattaga taatgctata agtcaagtaa aaacactaat aataataatg    240
aaatcatttt atgatattat tatatctgaa aaagcctcta tggatgaaat ggaaaaaaag    300
gaattatcct aaataatta tattgaaaaa acagat                             336

<210> SEQ ID NO 43
<211> LENGTH: 1627
<212> TYPE: PRT
<213> ORGANISM: Plasmodium falciparum

<400> SEQUENCE: 43

Met Lys Ile Ile Phe Phe Leu Cys Ser Phe Leu Phe Ile Ile Asn
1               5                   10                  15

Thr Gln Cys Val Thr His Glu Ser Tyr Gln Glu Leu Val Lys Lys Leu
            20                  25                  30

Glu Ala Leu Glu Asp Ala Val Leu Thr Gly Tyr Ser Leu Phe Gln Lys
        35                  40                  45

Glu Lys Met Val Leu Asn Glu Gly Thr Ser Gly Thr Ala Val Thr Thr
    50                  55                  60

Ser Thr Pro Gly Ser Lys Gly Ser Val Ala Ser Gly Gly Ser Gly Gly
65                  70                  75                  80

Ser Val Ala Ser Gly Gly Ser Val Ala Ser Gly Gly Ser Gly Asn Ser
                85                  90                  95

Arg Arg Thr Asn Pro Ser Asp Asn Ser Ser Asp Ser Asp Ala Lys Ser
            100                 105                 110

Tyr Ala Asp Leu Lys His Arg Val Arg Asn Tyr Leu Leu Thr Ile Lys
        115                 120                 125

Glu Leu Lys Tyr Pro Gln Leu Phe Asp Leu Thr Asn His Met Leu Thr
    130                 135                 140

Leu Cys Asp Asn Ile His Gly Phe Lys Tyr Leu Ile Asp Gly Tyr Glu
145                 150                 155                 160

Glu Ile Asn Glu Leu Leu Tyr Lys Leu Asn Phe Tyr Phe Asp Leu Leu
                165                 170                 175

Arg Ala Lys Leu Asn Asp Val Cys Ala Asn Asp Tyr Cys Gln Ile Pro
            180                 185                 190

Phe Asn Leu Lys Ile Arg Ala Asn Glu Leu Asp Val Leu Lys Lys Leu

-continued

```
            195                 200                 205
Val Phe Gly Tyr Arg Lys Pro Leu Asp Asn Ile Lys Asp Asn Val Gly
210                 215                 220

Lys Met Glu Asp Tyr Ile Lys Lys Asn Lys Lys Thr Ile Glu Asn Ile
225                 230                 235                 240

Asn Glu Leu Ile Glu Gly Ser Lys Lys Thr Ile Asp Lys Asn Lys Asn
                    245                 250                 255

Ala Thr Lys Glu Glu Lys Lys Lys Leu Tyr Gln Ala Gln Tyr Asp
                260                 265                 270

Leu Ser Ile Tyr Asn Lys Gln Leu Glu Glu Ala His Asn Leu Ile Ser
            275                 280                 285

Val Leu Glu Lys Arg Ile Asp Thr Leu Lys Lys Asn Glu Asn Ile Lys
        290                 295                 300

Lys Leu Leu Asp Lys Ile Asn Glu Ile Lys Asn Pro Pro Ala Asn
305                 310                 315                 320

Ser Gly Asn Thr Pro Asn Thr Leu Leu Asp Lys Asn Lys Lys Ile Glu
                    325                 330                 335

Glu His Glu Lys Glu Ile Lys Glu Ile Ala Lys Thr Ile Lys Phe Asn
                340                 345                 350

Ile Asp Ser Leu Phe Thr Asp Pro Leu Glu Leu Glu Tyr Tyr Leu Arg
            355                 360                 365

Glu Lys Asn Lys Asn Ile Asp Ile Ser Ala Lys Val Glu Thr Lys Glu
        370                 375                 380

Ser Thr Glu Pro Asn Glu Tyr Pro Asn Gly Val Thr Tyr Pro Leu Ser
385                 390                 395                 400

Tyr Asn Asp Ile Asn Asn Ala Leu Asn Glu Leu Asn Ser Phe Gly Asp
                    405                 410                 415

Leu Ile Asn Pro Phe Asp Tyr Thr Lys Glu Pro Ser Lys Asn Ile Tyr
                420                 425                 430

Thr Asp Asn Glu Arg Lys Lys Phe Ile Asn Glu Ile Lys Glu Lys Ile
            435                 440                 445

Lys Ile Glu Lys Lys Lys Ile Glu Ser Asp Lys Lys Ser Tyr Glu Asp
        450                 455                 460

Arg Ser Lys Ser Leu Asn Asp Ile Thr Lys Glu Tyr Glu Lys Leu Leu
465                 470                 475                 480

Asn Glu Ile Tyr Asp Ser Lys Phe Asn Asn Ile Asp Leu Thr Asn
                    485                 490                 495

Phe Glu Lys Met Met Gly Lys Arg Tyr Ser Tyr Lys Val Glu Lys Leu
                500                 505                 510

Thr His His Asn Thr Phe Ala Ser Tyr Glu Asn Ser Lys His Asn Leu
            515                 520                 525

Glu Lys Leu Thr Lys Ala Leu Lys Tyr Met Glu Asp Tyr Ser Leu Arg
        530                 535                 540

Asn Ile Val Val Glu Lys Glu Leu Lys Tyr Tyr Lys Asn Leu Ile Ser
545                 550                 555                 560

Lys Ile Lys Asn Glu Ile Glu Thr Leu Val Glu Asn Ile Lys Lys Asp
                    565                 570                 575

Glu Glu Gln Leu Phe Glu Lys Lys Ile Thr Lys Asp Gly Asn Lys Pro
                580                 585                 590

Asp Glu Lys Ile Leu Glu Val Ser Asp Ile Val Lys Val Gln Val Gln
            595                 600                 605

Lys Val Leu Leu Met Asn Lys Ile Asp Glu Leu Lys Lys Thr Gln Leu
        610                 615                 620
```

-continued

```
Ile Leu Lys Asn Val Glu Leu Lys His Asn Ile His Val Pro Asn Ser
625                 630                 635                 640

Tyr Lys Gln Glu Asn Lys Gln Glu Pro Tyr Tyr Leu Ile Val Leu Lys
            645                 650                 655

Lys Glu Ile Asp Lys Leu Lys Val Phe Met Pro Lys Val Glu Ser Leu
        660                 665                 670

Ile Asn Glu Glu Lys Lys Asn Ile Lys Thr Glu Gly Gln Ser Asp Asn
    675                 680                 685

Ser Glu Pro Ser Thr Glu Gly Glu Ile Thr Gly Gln Ala Thr Thr Lys
690                 695                 700

Pro Gly Gln Gln Ala Gly Ser Ala Leu Glu Gly Asp Ser Val Gln Ala
705                 710                 715                 720

Gln Ala Gln Glu Gln Lys Gln Ala Gln Pro Pro Val Pro Val Pro Val
                725                 730                 735

Pro Glu Ala Lys Ala Gln Val Pro Thr Pro Ala Pro Val Asn Asn
            740                 745                 750

Lys Thr Glu Asn Val Ser Lys Leu Asp Tyr Leu Glu Lys Leu Tyr Glu
        755                 760                 765

Phe Leu Asn Thr Ser Tyr Ile Cys His Lys Tyr Ile Leu Val Ser His
    770                 775                 780

Ser Thr Met Asn Glu Lys Ile Leu Lys Gln Tyr Lys Ile Thr Lys Glu
785                 790                 795                 800

Glu Glu Ser Lys Leu Ser Ser Cys Asp Pro Leu Asp Leu Leu Phe Asn
                805                 810                 815

Ile Gln Asn Asn Ile Pro Val Met Tyr Ser Met Phe Asp Ser Leu Asn
            820                 825                 830

Asn Ser Leu Ser Gln Leu Phe Met Glu Ile Tyr Glu Lys Glu Met Val
        835                 840                 845

Cys Asn Leu Tyr Lys Leu Lys Asp Asn Asp Lys Ile Lys Asn Leu Leu
    850                 855                 860

Glu Glu Ala Lys Lys Val Ser Thr Ser Val Lys Thr Leu Ser Ser Ser
865                 870                 875                 880

Ser Met Gln Pro Leu Ser Leu Thr Pro Gln Asp Lys Pro Glu Val Ser
                885                 890                 895

Ala Asn Asp Asp Thr Ser His Ser Thr Asn Leu Asn Asn Ser Leu Lys
            900                 905                 910

Leu Phe Glu Asn Ile Leu Ser Leu Gly Lys Asn Lys Asn Ile Tyr Gln
        915                 920                 925

Glu Leu Ile Gly Gln Lys Ser Ser Glu Asn Phe Tyr Glu Lys Ile Leu
    930                 935                 940

Lys Asp Ser Asp Thr Phe Tyr Asn Glu Ser Phe Thr Asn Phe Val Lys
945                 950                 955                 960

Ser Lys Ala Asp Asp Ile Asn Ser Leu Asn Asp Glu Ser Lys Arg Lys
                965                 970                 975

Lys Leu Glu Glu Asp Ile Asn Lys Leu Lys Thr Leu Gln Leu Ser
            980                 985                 990

Phe Asp Leu Tyr Asn Lys Tyr Lys Leu Lys Leu Glu Arg Leu Phe Asp
        995                 1000                1005

Lys Lys Lys Thr Val Gly Lys Tyr Lys Met Gln Ile Lys Lys Leu
        1010                1015                1020

Thr Leu Leu Lys Glu Gln Leu Glu Ser Leu Asn Ser Leu Asn
        1025                1030                1035
```

```
Asn Pro Lys His Val Leu Gln Asn Phe Ser Val Phe Phe Tyr Lys
    1040                1045                1050

Lys Lys Glu Ala Glu Ile Ala Glu Thr Glu Asn Thr Leu Glu Asn
    1055                1060                1065

Thr Lys Ile Leu Leu Lys His Tyr Lys Gly Leu Val Lys Tyr Tyr
    1070                1075                1080

Asn Gly Glu Ser Ser Pro Leu Lys Thr Leu Ser Glu Glu Ser Ile
    1085                1090                1095

Gln Thr Glu Asp Asn Tyr Ala Ser Leu Glu Asn Phe Lys Val Leu
    1100                1105                1110

Ser Lys Leu Glu Gly Lys Leu Lys Asp Asn Leu Asn Leu Glu Lys
    1115                1120                1125

Lys Lys Leu Ser Tyr Leu Ser Ser Gly Leu His His Leu Ile Ala
    1130                1135                1140

Glu Leu Lys Lys Val Ile Lys Asn Lys Asn Tyr Thr Gly Asn Ser
    1145                1150                1155

Pro Ser Glu Asn Asn Thr Asp Val Asn Asn Ala Leu Glu Ser Tyr
    1160                1165                1170

Lys Lys Phe Leu Pro Glu Gly Thr Asp Val Ala Thr Val Val Ser
    1175                1180                1185

Glu Ser Gly Ser Asp Thr Leu Glu Gln Ser Gln Pro Lys Lys Pro
    1190                1195                1200

Ala Ser Thr His Val Gly Ala Glu Ser Asn Thr Ile Thr Thr Ser
    1205                1210                1215

Gln Asn Val Asp Asp Glu Val Asp Asp Val Ile Ile Val Pro Ile
    1220                1225                1230

Phe Gly Glu Ser Glu Glu Asp Tyr Asp Asp Leu Gly Gln Val Val
    1235                1240                1245

Thr Gly Glu Ala Val Thr Pro Ser Val Ile Asp Asn Ile Leu Ser
    1250                1255                1260

Lys Ile Glu Asn Glu Tyr Glu Val Leu Tyr Leu Lys Pro Leu Ala
    1265                1270                1275

Gly Val Tyr Arg Ser Leu Lys Lys Gln Leu Glu Asn Asn Val Met
    1280                1285                1290

Thr Phe Asn Val Asn Val Lys Asp Ile Leu Asn Ser Arg Phe Asn
    1295                1300                1305

Lys Arg Glu Asn Phe Lys Asn Val Leu Glu Ser Asp Leu Ile Pro
    1310                1315                1320

Tyr Lys Asp Leu Thr Ser Ser Asn Tyr Val Val Lys Asp Pro Tyr
    1325                1330                1335

Lys Phe Leu Asn Lys Glu Lys Arg Asp Lys Phe Leu Ser Ser Tyr
    1340                1345                1350

Asn Tyr Ile Lys Asp Ser Ile Asp Thr Asp Ile Asn Phe Ala Asn
    1355                1360                1365

Asp Val Leu Gly Tyr Tyr Lys Ile Leu Ser Glu Lys Tyr Lys Ser
    1370                1375                1380

Asp Leu Asp Ser Ile Lys Lys Tyr Ile Asn Asp Lys Gln Gly Glu
    1385                1390                1395

Asn Glu Lys Tyr Leu Pro Phe Leu Asn Asn Ile Glu Thr Leu Tyr
    1400                1405                1410

Lys Thr Val Asn Asp Lys Ile Asp Leu Phe Val Ile His Leu Glu
    1415                1420                1425

Ala Lys Val Leu Asn Tyr Thr Tyr Glu Lys Ser Asn Val Glu Val
```

-continued

```
             1430                1435                1440

Lys Ile Lys Glu Leu Asn Tyr Leu Lys Thr Ile Gln Asp Lys Leu
         1445                1450                1455

Ala Asp Phe Lys Lys Asn Asn Phe Val Gly Ile Ala Asp Leu
1460                1465                1470

Ser Thr Asp Tyr Asn His Asn Asn Leu Leu Thr Lys Phe Leu Ser
    1475                1480                1485

Thr Gly Met Val Phe Glu Asn Leu Ala Lys Thr Val Leu Ser Asn
1490                1495                1500

Leu Leu Asp Gly Asn Leu Gln Gly Met Leu Asn Ile Ser Gln His
    1505                1510                1515

Gln Cys Val Lys Lys Gln Cys Pro Gln Asn Ser Gly Cys Phe Arg
    1520                1525                1530

His Leu Asp Glu Arg Glu Glu Cys Lys Cys Leu Leu Asn Tyr Lys
    1535                1540                1545

Gln Glu Gly Asp Lys Cys Val Glu Asn Pro Asn Pro Thr Cys Asn
    1550                1555                1560

Glu Asn Asn Gly Gly Cys Asp Ala Asp Ala Lys Cys Thr Glu Glu
    1565                1570                1575

Asp Ser Gly Ser Asn Gly Lys Lys Ile Thr Cys Glu Cys Thr Lys
    1580                1585                1590

Pro Asp Ser Tyr Pro Leu Phe Asp Gly Ile Phe Cys Ser Ser Ser
    1595                1600                1605

Asn Phe Leu Gly Ile Ser Leu Leu Ile Leu Met Leu Ile Leu
    1610                1615                1620

Tyr Ser Phe Ile
    1625

<210> SEQ ID NO 44
<211> LENGTH: 358
<212> TYPE: PRT
<213> ORGANISM: Artificial Sequence
<220> FEATURE:
<223> OTHER INFORMATION: Polypeptide fragment

<400> SEQUENCE: 44

Ala Val Thr Pro Ser Val Ile Asp Asn Ile Leu Ser Lys Ile Glu Asn
1               5                   10                  15

Glu Tyr Glu Val Leu Tyr Leu Lys Pro Leu Ala Gly Val Tyr Arg Ser
                20                  25                  30

Leu Lys Lys Gln Leu Glu Asn Asn Val Met Thr Phe Asn Val Asn Val
            35                  40                  45

Lys Asp Ile Leu Asn Ser Arg Phe Asn Lys Arg Glu Asn Phe Lys Asn
        50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                85                  90                  95

Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
        115                 120                 125

Lys Tyr Lys Ser Asp Leu Asp Ser Ile Lys Lys Tyr Ile Asn Asp Lys
    130                 135                 140

Gln Gly Glu Asn Glu Lys Tyr Leu Pro Phe Leu Asn Asn Ile Glu Thr
```

```
                    145                 150                 155                 160
            Leu Tyr Lys Thr Val Asn Asp Lys Ile Asp Leu Phe Val Ile His Leu
                            165                 170                 175

Glu Ala Lys Val Leu Asn Tyr Thr Tyr Glu Lys Ser Asn Val Glu Val
                        180                 185                 190

Lys Ile Lys Glu Leu Asn Tyr Leu Lys Thr Ile Gln Asp Lys Leu Ala
                        195                 200                 205

Asp Phe Lys Lys Asn Asn Phe Val Gly Ile Ala Asp Leu Ser Thr
                210                 215                 220

Asp Tyr Asn His Asn Asn Leu Leu Thr Lys Phe Leu Ser Thr Gly Met
            225                 230                 235                 240

Val Phe Glu Asn Leu Ala Lys Thr Val Leu Ser Asn Leu Leu Asp Gly
                            245                 250                 255

Asn Leu Gln Gly Met Leu Asn Ile Ser Gln His Gln Cys Val Lys Lys
                        260                 265                 270

Gln Cys Pro Gln Asn Ser Gly Cys Phe Arg His Leu Asp Glu Arg Glu
                        275                 280                 285

Glu Cys Lys Cys Leu Leu Asn Tyr Lys Gln Glu Gly Asp Lys Cys Val
            290                 295                 300

Glu Asn Pro Asn Pro Thr Cys Asn Glu Asn Asn Gly Gly Cys Asp Ala
            305                 310                 315                 320

Asp Ala Lys Cys Thr Glu Glu Asp Ser Gly Ser Asn Gly Lys Lys Ile
                        325                 330                 335

Thr Cys Glu Cys Thr Lys Pro Asp Ser Tyr Pro Leu Phe Asp Gly Ile
                        340                 345                 350

Phe Cys Ser Ser Ser Asn
                    355

<210> SEQ ID NO 45
<211> LENGTH: 116
<212> TYPE: PRT
<213> ORGANISM: Artificial Sequence
<220> FEATURE:
<223> OTHER INFORMATION: Polypeptide fragment

<400> SEQUENCE: 45

Met Leu Asn Ile Ser Gln His Gln Cys Val Lys Lys Gln Cys Pro Glu
1               5                   10                  15

Asn Ser Gly Cys Phe Arg His Leu Asp Glu Arg Glu Glu Cys Lys Cys
            20                  25                  30

Leu Leu Asn Tyr Lys Gln Glu Gly Asp Lys Cys Val Glu Asn Pro Asn
        35                  40                  45

Pro Thr Cys Asn Glu Asn Asn Gly Gly Cys Asp Ala Asp Ala Thr Cys
    50                  55                  60

Thr Glu Glu Asp Ser Gly Ser Ser Arg Lys Lys Ile Thr Cys Glu Cys
65                  70                  75                  80

Thr Lys Pro Asp Ser Tyr Pro Leu Phe Asp Gly Ile Phe Cys Ser Ser
                85                  90                  95

Ser Asn Phe Leu Gly Ile Ser Phe Leu Leu Ile Leu Met Leu Ile Leu
            100                 105                 110

Tyr Ser Phe Ile
        115

<210> SEQ ID NO 46
<211> LENGTH: 6
<212> TYPE: PRT
```

```
<213> ORGANISM: Artificial Sequence
<220> FEATURE:
<223> OTHER INFORMATION: Peptide linker

<400> SEQUENCE: 46

Gly Gly Ser Gly Gly Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Peptide linker

<400> SEQUENCE: 47

Pro Ser Pro Ser Pro
1               5

<210> SEQ ID NO 48
<211> LENGTH: 5
<212> TYPE: PRT
<213> ORGANISM: Artificial Sequence
      220>
<223> OTHER INFORMATION: Peptide linker

<400> SEQUENCE: 48

Ala Ser Ala Ser Ala
1               5

<210> SEQ ID NO 49
<211> LENGTH: 5
<212> TYPE: PRT
<213> ORGANISM: Artificial Sequence
<220> FEATURE:
<223> OTHER INFORMATION: Peptide linker

<400> SEQUENCE: 49

Pro Ser Pro Ser Pro
1               5

<210> SEQ ID NO 50
<211> LENGTH: 4
<212> TYPE: PRT
<213> ORGANISM: Artificial Sequence
<220> FEATURE:
<223> OTHER INFORMATION: Peptide linker

<400> SEQUENCE: 50

Lys Lys Lys Lys
1

<210> SEQ ID NO 51
<211> LENGTH: 4
<212> TYPE: PRT
<213> ORGANISM: Artificial Sequence
<220> FEATURE:
<223> OTHER INFORMATION: Peptide linker

<400> SEQUENCE: 51

Arg Arg Arg Arg
1

<210> SEQ ID NO 52
<211> LENGTH: 4
<212> TYPE: PRT
<213> ORGANISM: Artificial Sequence
```

```
<220> FEATURE:
<223> OTHER INFORMATION: Peptide linker

<400> SEQUENCE: 52

Gly Gly Gly Gly
1

<210> SEQ ID NO 53
<211> LENGTH: 5
<212> TYPE: PRT
<213> ORGANISM: Artificial Sequence
<220> FEATURE:
<223> OTHER INFORMATION: Peptide linker

<400> SEQUENCE: 53

Gly Gly Gly Gly Ser
1               5

<210> SEQ ID NO 54
<211> LENGTH: 10
<212> TYPE: PRT
<213> ORGANISM: Artificial Sequence
<220> FEATURE:
<223> OTHER INFORMATION: peptide linker

<400> SEQUENCE: 54

Gly Gly Gly Gly Ser Gly Gly Gly Gly Ser
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Peptide linker

<400> SEQUENCE: 55

Gly Gly Gly Gly Ser Gly Gly Gly Gly Ser Gly Gly Gly Gly Ser Gly
1               5                   10                  15

Gly Gly Gly Ser
            20

<210> SEQ ID NO 56
<211> LENGTH: 25
<212> TYPE: PRT
<213> ORGANISM: Artificial Sequence
<220> FEATURE:
<223> OTHER INFORMATION: Peptide linker

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 57
<211> LENGTH: 30
<212> TYPE: PRT
<213> ORGANISM: Artificial Sequence
<220> FEATURE:
<223> OTHER INFORMATION: Peptide linker

<400> SEQUENCE: 57

Gly Gly Gly Gly Ser Gly Gly Gly Gly Ser Gly Gly Gly Gly Ser Gly
1               5                   10                  15
```

Gly Gly Gly Ser Gly Gly Gly Ser Gly Gly Gly Ser
            20              25              30

<210> SEQ ID NO 58
<211> LENGTH: 1482
<212> TYPE: DNA
<213> ORGANISM: Artificial Sequence
<220> FEATURE:
<223> OTHER INFORMATION: Synthetic oligonucleotide fragment

<400> SEQUENCE: 58

| | |
|---|---:|
| ggtacccata tgaaaagcta ttgcaatgat ctgagcgaat gcgatattgg cctgatttat | 60 |
| catttcgata cctattgcat caatgatcag tacctgtttg tgagctatag ctgtagcaat | 120 |
| ctgtgcaata aatgccataa taatagcacc tgttatggca atcgctttaa ttatgattgc | 180 |
| ttttgcgata atccgtatat tagcaaatat ggcaataaac tgtgcgaacg tccgaatgat | 240 |
| tgtgaaagcg ttctgtgtag ccagaatcag gtttgtcaga ttctgccgaa tgataaactg | 300 |
| atttgtcagt gcgaagaagg ctataaaaac gttaaaggta atgcgtgcc ggataataaa | 360 |
| tgtgatctga gctgtccgag caataaagtt tgcgttattg aaaatggcaa acagacctgt | 420 |
| aaatgcagcg aacgttttgt tctggaaaat ggtgtttgca tttgcgccaa tgattataaa | 480 |
| atggaagatg gcatcaattg cattgccaaa aataaatgca acgcaaaga gtatgaaaat | 540 |
| atttgcacca atccgaatga atgtgcgcc tataatgaag aaaccgatat tgtgaaatgc | 600 |
| gaatgcaaag aacattatta tcgtagcagc cgtggtgaat gcattctgaa tgattattgc | 660 |
| aaagacatca attgcaaaga aaatgaagaa tgcagcattg tgaatttaa accggaatgc | 720 |
| gtgtgcaaag aaaatctgaa aaaaaataac aaaggcgagt gcatttatga aaattcatgc | 780 |
| ctgattaatg aaggcaattg cccgaaagat agcaaatgca tttatcgcga atataaaccg | 840 |
| catgaatgcg tttgcaataa acagggtcat gttgccgtta atggtaaatg tgtgctggaa | 900 |
| gataaatgcg tgcataataa aaaatgtagc gaaaattcca tttgcgtgaa tgtgatgaat | 960 |
| aaagaaccga tttgcgtgtg cacctataat tattataaaa aagatggcgt gtgcctgatt | 1020 |
| cagaatccgt gtctgaaaga taatggtggt tgtagccgta atagcgaatg caccttaaa | 1080 |
| tattccaaaa ttaattgtac ctgtaaagag aactacaaaa acaaagatga tagctgcgtg | 1140 |
| ccgaatacca tgaatatga tgaaagcttt acctttcagt ataatgatga tgccagcatt | 1200 |
| attctgggtg catgtggtat gattgaattt agctatatct acaaccagat tatctggaaa | 1260 |
| attaataata gcaaagagag ctacgttttc tattatgatt atccgaccgc aggcaatatt | 1320 |
| gaagtgcaga ttaaaaacga aattttccac accattatct acctgaaaaa aaaaattggc | 1380 |
| aatagcgtga tttatgatga ttttcaggtg gatcatcaga cctgtattta tgaaaatgtg | 1440 |
| ttctattaca gcaatcagaa ttaaggatcc ctcgaggagc tc | 1482 |

<210> SEQ ID NO 59
<211> LENGTH: 1482
<212> TYPE: DNA
<213> ORGANISM: Artificial Sequence
<220> FEATURE:
<223> OTHER INFORMATION: Synthetic oligonucleotide fragment

<400> SEQUENCE: 59

| | |
|---|---:|
| gagctcctcg agggatcctt aattctgatt gctgtaatag aacacatttt cataaataca | 60 |
| ggtctgatga tccacctgaa aatcatcata aatcacgcta ttgccaattt ttttttcag | 120 |
| gtagataatg gtgtggaaaa tttcgttttt aatctgcact tcaatattgc ctgcggtcgg | 180 |

-continued

```
ataatcataa tagaaaacgt agctctcttt gctattatta attttccaga taatctggtt    240
gtagatatag ctaaattcaa tcataccaca tgcacccaga ataatgctgg catcatcatt    300
atactgaaag gtaaagcttt catcatattc attggtattc ggcacgcagc tatcatcttt    360
gtttttgtag ttctctttac aggtacaatt aattttggaa tatttaaagg tgcattcgct    420
attacggcta caaccaccat tatctttcag acacggattc tgaatcaggc acacgccatc    480 tttttataa taattatagg tgcacacgca aatcggttct ttattcatca cattcacgca    540
aatggaattt tcgctacatt ttttattatg cacgcattta tcttccagca cacatttacc    600
attaacggca acatgaccct gtttattgca aacgcattca tgcggtttat attcgcgata    660
aatgcatttg ctatctttcg ggcaattgcc ttcattaatc aggcatgaat tttcataaat    720
gcactcgcct ttgttatttt ttttcagatt ttctttgcac acgcattccg gtttaaaatt    780
cacaatgctg cattcttcat tttctttgca attgatgtct ttgcaataat cattcagaat    840
gcattcacca cggctgctac gataataatg ttctttgcat tcgcatttca caatatcggt    900
ttcttcatta taggcgcaca tttcattcgg attggtgcaa atattttcat actctttgcg    960
tttgcattta tttttggcaa tgcaattgat gccatcttcc attttataat cattggcgca   1020
aatgcaaaca ccattttcca gaacaaaacg ttcgctgcat ttacaggtct gtttgccatt   1080
ttcaataacg caaactttat tgctcggaca gctcagatca catttattat ccggcacgca   1140
tttaccttta acgtttttat agccttcttc gcactgacaa atcagtttat cattcggcag   1200
aatctgacaa acctgattct ggctacacag aacgctttca caatcattcg gacgttcgca   1260
cagtttattg ccatatttgc taatatacgg attatcgcaa aagcaatcat aattaaagcg   1320
attgccataa caggtgctat tattatggca tttattgcac agattgctac agctatagct   1380
cacaaacagg tactgatcat tgatgcaata ggtatcgaaa tgataaatca ggccaatatc   1440
gcattcgctc agatcattgc aatagctttt catatgggta cc                        1482
```

<210> SEQ ID NO 60
<211> LENGTH: 483
<212> TYPE: PRT
<213> ORGANISM: Artificial Sequence
<220> FEATURE:
<223> OTHER INFORMATION: Synthetic pfRip antigenic fragment

<400> SEQUENCE: 60

```
Lys Ser Tyr Cys Asn Asp Leu Ser Glu Cys Asp Ile Gly Leu Ile Tyr
 1               5                  10                  15

His Phe Asp Thr Tyr Cys Ile Asn Asp Gln Tyr Leu Phe Val Ser Tyr
            20                  25                  30

Ser Cys Ser Asn Leu Cys Asn Lys Cys His Asn Asn Ser Thr Cys Tyr
        35                  40                  45

Gly Asn Arg Phe Asn Tyr Asp Cys Phe Cys Asp Asn Pro Tyr Ile Ser
    50                  55                  60

Lys Tyr Gly Asn Lys Leu Cys Glu Arg Pro Asn Asp Cys Glu Ser Val
65                  70                  75                  80

Leu Cys Ser Gln Asn Gln Val Cys Gln Ile Leu Pro Asn Asp Lys Leu
                85                  90                  95

Ile Cys Gln Cys Glu Glu Gly Tyr Lys Asn Val Lys Gly Lys Cys Val
            100                 105                 110

Pro Asp Asn Lys Cys Asp Leu Ser Cys Pro Ser Asn Lys Val Cys Val
        115                 120                 125

Ile Glu Asn Gly Lys Gln Thr Cys Lys Cys Ser Glu Arg Phe Val Leu
```

```
                130                 135                 140
Glu Asn Gly Val Cys Ile Cys Ala Asn Asp Tyr Lys Met Glu Asp Gly
145                 150                 155                 160

Ile Asn Cys Ile Ala Lys Asn Lys Cys Lys Arg Lys Glu Tyr Glu Asn
                165                 170                 175

Ile Cys Thr Asn Pro Asn Glu Met Cys Ala Tyr Asn Glu Glu Thr Asp
            180                 185                 190

Ile Val Lys Cys Glu Cys Lys Glu His Tyr Tyr Arg Ser Ser Arg Gly
        195                 200                 205

Glu Cys Ile Leu Asn Asp Tyr Cys Lys Asp Ile Asn Cys Lys Glu Asn
    210                 215                 220

Glu Glu Cys Ser Ile Val Asn Phe Lys Pro Glu Cys Val Cys Lys Glu
225                 230                 235                 240

Asn Leu Lys Lys Asn Asn Lys Gly Glu Cys Ile Tyr Glu Asn Ser Cys
                245                 250                 255

Leu Ile Asn Glu Gly Asn Cys Pro Lys Asp Ser Lys Cys Ile Tyr Arg
            260                 265                 270

Glu Tyr Lys Pro His Glu Cys Val Cys Asn Lys Gln Gly His Val Ala
        275                 280                 285

Val Asn Gly Lys Cys Val Leu Glu Asp Lys Cys Val His Asn Lys Lys
    290                 295                 300

Cys Ser Glu Asn Ser Ile Cys Val Asn Val Met Asn Lys Glu Pro Ile
305                 310                 315                 320

Cys Val Cys Thr Tyr Asn Tyr Tyr Lys Lys Asp Gly Val Cys Leu Ile
                325                 330                 335

Gln Asn Pro Cys Leu Lys Asp Asn Gly Gly Cys Ser Arg Asn Ser Glu
            340                 345                 350

Cys Thr Phe Lys Tyr Ser Lys Ile Asn Cys Thr Cys Lys Glu Asn Tyr
        355                 360                 365

Lys Asn Lys Asp Asp Ser Cys Val Pro Asn Thr Asn Glu Tyr Asp Glu
    370                 375                 380

Ser Phe Thr Phe Gln Tyr Asn Asp Asp Ala Ser Ile Ile Leu Gly Ala
385                 390                 395                 400

Cys Gly Met Ile Glu Phe Ser Tyr Ile Tyr Asn Gln Ile Ile Trp Lys
                405                 410                 415

Ile Asn Asn Ser Lys Glu Ser Tyr Val Phe Tyr Tyr Pro Thr
            420                 425                 430

Ala Gly Asn Ile Glu Val Gln Ile Lys Asn Glu Ile Phe His Thr Ile
        435                 440                 445

Ile Tyr Leu Lys Lys Lys Ile Gly Asn Ser Val Ile Tyr Asp Asp Phe
    450                 455                 460

Gln Val Asp His Gln Thr Cys Ile Tyr Glu Asn Val Phe Tyr Tyr Ser
465                 470                 475                 480

Asn Gln Asn

<210> SEQ ID NO 61
<211> LENGTH: 31
<212> TYPE: PRT
<213> ORGANISM: Artificial Sequence
<220> FEATURE:
<223> OTHER INFORMATION: Synthetic peptide Histidine and FLAG tag

<400> SEQUENCE: 61

Met Ala His His His His His His Ser Ser Gly Asp Tyr Lys Asp Asp
1               5                   10                  15
```

-continued

```
Asp Asp Lys Gly Gly Glu Gln Leu Tyr Phe Gln Gly Thr His Met
            20                  25                  30
```

<210> SEQ ID NO 62
<211> LENGTH: 23
<212> TYPE: PRT
<213> ORGANISM: Artificial Sequence
<220> FEATURE:
<223> OTHER INFORMATION: Synthetic peptide Histidine tag

<400> SEQUENCE: 62

```
Met Ala His His His His His His Val Gly Thr Gly Ser Asn Asp Asp
 1               5                  10                  15

Asp Asp Lys Ser Pro Asp Pro
            20
```

<210> SEQ ID NO 63
<211> LENGTH: 8
<212> TYPE: PRT
<213> ORGANISM: Artificial Sequence
<220> FEATURE:
<223> OTHER INFORMATION: Synthetic peptide C-terminal Histidine tag

<400> SEQUENCE: 63

```
Leu Glu His His His His His His
 1               5
```

<210> SEQ ID NO 64
<211> LENGTH: 538
<212> TYPE: PRT
<213> ORGANISM: Artificial Sequence
<220> FEATURE:
<223> OTHER INFORMATION: Synthetic pfEBA175 antigenic fragment

<400> SEQUENCE: 64

```
Gln Glu Ala Val Pro Glu Glu Ser Thr Glu Ile Ala His Arg Thr Glu
 1               5                  10                  15

Thr Arg Thr Asp Glu Arg Lys Asn Gln Glu Pro Ala Asn Lys Asp Leu
            20                  25                  30

Lys Asn Pro Gln Gln Ser Val Gly Glu Asn Gly Thr Lys Asp Leu Leu
        35                  40                  45

Gln Glu Asp Leu Gly Gly Ser Arg Ser Glu Asp Glu Val Thr Gln Glu
    50                  55                  60

Phe Gly Val Asn His Gly Ile Pro Lys Gly Asp Gln Thr Leu Gly
65                  70                  75                  80

Lys Ser Asp Ala Ile Pro Asn Ile Gly Glu Pro Thr Gly Ile Ser
                85                  90                  95

Thr Thr Glu Glu Ser Arg His Glu Gly His Asn Lys Gln Ala Leu
            100                 105                 110

Ser Thr Ser Val Asp Glu Pro Glu Leu Ser Asp Thr Leu Gln Leu His
        115                 120                 125

Glu Asp Thr Lys Glu Asn Asp Lys Leu Pro Leu Glu Ser Ser Thr Ile
    130                 135                 140

Thr Ser Pro Thr Glu Ser Gly Ser Ser Asp Thr Glu Glu Thr Pro Ser
145                 150                 155                 160

Ile Ser Glu Gly Pro Lys Gly Asn Glu Gln Lys Lys Arg Asp Asp Asp
                165                 170                 175

Ser Leu Ser Lys Ile Ser Val Ser Pro Glu Asn Ser Arg Pro Glu Thr
            180                 185                 190
```

```
Asp Ala Lys Asp Thr Ser Asn Leu Leu Lys Leu Lys Gly Asp Val Asp
    195                 200                 205
Ile Ser Met Pro Lys Ala Val Ile Gly Ser Ser Pro Asn Asp Asn Ile
    210                 215                 220
Asn Val Thr Glu Gln Gly Asp Asn Ile Ser Gly Val Asn Ser Lys Pro
225                 230                 235                 240
Leu Ser Asp Asp Val Arg Pro Asp Lys Asn His Glu Glu Val Lys Glu
                245                 250                 255
His Thr Ser Asn Ser Asp Asn Val Gln Gln Ser Gly Gly Ile Val Asn
                260                 265                 270
Met Asn Val Glu Lys Glu Leu Lys Asp Thr Leu Glu Asn Pro Ser Ser
        275                 280                 285
Ser Leu Asp Glu Gly Lys Ala His Glu Glu Leu Ser Glu Pro Asn Leu
        290                 295                 300
Ser Ser Asp Gln Asp Met Ser Asn Thr Pro Gly Pro Leu Asp Asn Thr
305                 310                 315                 320
Ser Glu Glu Thr Thr Glu Arg Ile Ser Asn Asn Glu Tyr Lys Val Asn
                325                 330                 335
Glu Arg Glu Gly Glu Arg Thr Leu Thr Lys Glu Tyr Glu Asp Ile Val
            340                 345                 350
Leu Lys Ser His Met Asn Arg Glu Ser Asp Asp Gly Glu Leu Tyr Asp
            355                 360                 365
Glu Asn Ser Asp Leu Ser Thr Val Asn Asp Glu Ser Glu Asp Ala Glu
        370                 375                 380
Ala Lys Met Lys Gly Asn Asp Thr Ser Glu Met Ser His Asn Ser Ser
385                 390                 395                 400
Gln His Ile Glu Ser Asp Gln Gln Lys Asn Asp Met Lys Thr Val Gly
                405                 410                 415
Asp Leu Gly Thr Thr His Val Gln Asn Glu Ile Ser Val Pro Val Thr
                420                 425                 430
Gly Glu Ile Asp Glu Lys Leu Arg Glu Ser Lys Glu Ser Lys Ile His
            435                 440                 445
Lys Ala Glu Glu Glu Arg Leu Ser His Thr Asp Ile His Lys Ile Asn
450                 455                 460
Pro Glu Asp Arg Asn Ser Asn Thr Leu His Leu Lys Asp Ile Arg Asn
465                 470                 475                 480
Glu Glu Asn Glu Arg His Leu Thr Asn Gln Asn Ile Asn Ile Ser Gln
                485                 490                 495
Glu Arg Asp Leu Gln Lys His Gly Phe His Thr Met Asn Asn Leu His
            500                 505                 510
Gly Asp Gly Val Ser Glu Arg Ser Gln Ile Asn His Ser His His Gly
        515                 520                 525
Asn Arg Gln Asp Arg Gly Gly Asn Ser Gly
530                 535
```

TREATMENT AND PREVENTION OF MALARIA

CROSS REFERENCE TO RELATED APPLICATIONS

The present application is a Continuation in Part Application of co-pending U.S. application Ser. No. 13/884,604, filed Jul. 23, 2013, which claims priority from PCT Application No. PCT/AU2011/001442, filed Nov. 8, 2011, which in turn, claims priority from U.S. Provisional Application Ser. No. 61/411,598, filed Nov. 9, 2010, and U.S. Provisional Application Ser. No. 61/435,602, filed Jan. 24, 2011. Applicants claim the benefits of 35 U.S.C. § 120 as to the U.S. application and the PCT application and priority under 35 U.S.C. § 119 as to the U.S. provisional applications, and the entire disclosures of all applications are incorporated herein by reference in their entireties.

FIELD OF THE INVENTION

The present invention relates to polypeptides from *Plasmodium* and polynucleotides encoding the polypeptides. The invention further relates to compositions comprising the polypeptides and their use in the treatment and prevention of malaria.

BACKGROUND OF THE INVENTION

Human malaria is caused by infection with protozoan parasites of the genus *Plasmodium*. Four species are known to cause human disease: *Plasmodium falciparum, Plasmodium malariae, Plasmodium ovale* and *Plasmodium vivax*. However, *Plasmodium falciparum* is responsible for the majority of severe disease and death. Recent estimates of the annual number of clinical malaria cases worldwide range from 214 to 397 million (The world health report 2002: reducing risks, promoting healthy life. Geneva: World Health Organization; Breman et al., 2004), although a higher estimate of 515 million (range 300 to 660 million) clinical cases of *Plasmodium falciparum* in 2002 has been proposed (Snow et al., 2004). Annual mortality (nearly all from *Plasmodium falciparum* malaria) is thought to be around 1.1 million (Breman et al., 2004).

Malaria also significantly increases the risk of childhood death from other causes (Snow et al., 2004). Almost half of the world's population lives in areas where they are exposed to risk of malaria (Hay et al., 2004), and the increasing numbers of visitors to endemic areas are also at risk. Despite continued efforts to control malaria, it remains a major health problem in many regions of the world, and new ways to prevent and/or treat the disease are urgently needed.

Early optimism for vaccines based on malarial proteins (so called subunit vaccines) has been tempered over the last two decades as the problems caused by allelic polymorphism and antigenic variation, original antigenic sin, and the difficulty of generating high levels of durable immunity emerged, and with the notable failures of many promising subunit vaccines (such as SPf66) have led to calls for a change in approach towards a malaria vaccine. Consequently, this growing sense of frustration has lead to the pursuit of different approaches that focus on attenuated strains of malaria parasite or irradiated *Plasmodium falciparum* sporozoites (Hoffmann et al., 2002). Similarly, both the limited success achieved to date with protein-based vaccines and the recognition that cell mediated immunity may be critical to protection against hepatic and perhaps blood stages of the parasite has led to a push for DNA and vectored vaccines, which generate relatively strong cell mediated immunity. Unfortunately, DNA vaccines have demonstrated poor efficacy in humans with respect to antibody induction (Wang et al., 2001). Thus, there remains a need for methods of treating and preventing malaria.

SUMMARY OF THE INVENTION

The present inventors have identified novel recombinant fragments of *Plasmodium* polypeptides that can be used in vaccine compositions to generate antibodies that inhibit merozoite binding and invasion of erythrocytes.

Accordingly, in one aspect, the present invention provides a recombinant combination vaccine composition comprising an isolated and/or recombinant first and a second polypeptide, wherein the first polypeptide consists of SEQ ID NO: 60 or consists of SEQ ID NO: 60 having one or more point mutations selected from the group consisting of:
L at amino acid position 70 replaced with V,
A at amino acid position 152 replaced with G,
Y at amino acid position 382 replaced with N, and
I at amino acid position 436 replaced with M;
and wherein the second polypeptide consists of SEQ ID NO: 64 or consists of SEQ ID NO: 64 having one or more point mutations selected from the group consisting of:
S at amino acid position 8 replaced with N,
E at amino acid position 163 replaced with K,
K at amino acid position 172 replaced with E,
E at amino acid position 298 replaced with V, and
G at amino acid position 340 replaced with D;
or wherein the second polypeptide consists of SEQ ID NO: 36 or consists of SEQ ID NO:
36 having one or more point mutations selected from the group consisting of:
S at amino acid position 9 replaced with N,
E at amino acid position 164 replaced with K,
K at amino acid position 173 replaced with E,
E at amino acid position 299 replaced with V, and
G at amino acid position 341 replaced with D;
and an immunologically effective amount of an adjuvant.

In a particular embodiment, the first polypeptide consists of SEQ ID NO: 60 and the second polypeptide consists of SEQ ID NO: 64.

In another embodiment, the recombinant combination vaccine composition further comprises a Rh polypeptide, wherein the Rh polypeptide is an Rh5 polypeptide selected from the group consisting of: i) an amino acid sequence selected from any one of SEQ ID NOs:17 to 28, or ii) an amino acid sequence which is at least 70% identical to any one of SEQ ID NOs:17 to 28, or iii) or an amino acid sequence of SEQ ID NO: 18 comprising one or more point mutations selected from the group consisting of:
E at amino acid position 25 replaced with K,
Y at amino acid position 124 replaced with H,
H at amino acid position 125 replaced with N,
S at amino acid position 174 replaced with Y,
C at amino acid position 180 replaced with Y,
I at amino acid position 181 replaced with K or R,
N at amino acid position 324 replaced with Y or D,
Y at amino acid position 335 replaced with F,
E at amino acid position 339 replaced with D,
V at amino acid position 348 replaced with I,
I at amino acid position 384 replaced with V,
I at amino acid position 387 replaced with M, and
K at amino acid position 406 replaced with N.

In a more particular embodiment, the Rh polypeptide comprises an amino acid sequence of SEQ ID NO: 18.

Also encompassed herein is a recombinant combination vaccine composition comprising an isolated and/or recombinant first and a second polypeptide, wherein the first polypeptide consists of SEQ ID NO: 64 or consists of SEQ ID NO: 64 having one or more point mutations selected from the group consisting of:
S at amino acid position 8 replaced with N,
E at amino acid position 163 replaced with K,
K at amino acid position 172 replaced with E,
E at amino acid position 298 replaced with V, and
G at amino acid position 340 replaced with D; and
wherein the second polypeptide consists of SEQ ID NO: 36 or consists of SEQ ID NO: 36 having one or more point mutations selected from the group consisting of:
S at amino acid position 9 replaced with N,
E at amino acid position 164 replaced with K,
K at amino acid position 173 replaced with E,
E at amino acid position 299 replaced with V, and
G at amino acid position 341 replaced with D;
and an immunologically effective amount of an adjuvant.

In a particular embodiment thereof, the first polypeptide consists of SEQ ID NO: 64 and the second polypeptide consists of SEQ ID NO: 36.

In a further embodiment thereof, the recombinant combination vaccine composition further comprises a Rh polypeptide, wherein the Rh polypeptide is an Rh5 polypeptide selected from the group consisting of: i) an amino acid sequence selected from any one of SEQ ID NOs:17 to 28, or ii) an amino acid sequence which is at least 70% identical to any one of SEQ ID NOs:17 to 28, or iii) or an amino acid sequence of SEQ ID NO: 18 comprising one or more point mutations selected from the group consisting of:
E at amino acid position 25 replaced with K,
Y at amino acid position 124 replaced with H,
H at amino acid position 125 replaced with N,
S at amino acid position 174 replaced with Y,
C at amino acid position 180 replaced with Y,
I at amino acid position 181 replaced with K or R,
N at amino acid position 324 replaced with Y or D,
Y at amino acid position 335 replaced with F,
E at amino acid position 339 replaced with D,
V at amino acid position 348 replaced with I,
I at amino acid position 384 replaced with V,
I at amino acid position 387 replaced with M, and
K at amino acid position 406 replaced with N.

In a more particular embodiment, the Rh polypeptide comprises an amino acid sequence of SEQ ID NO: 18.

In one embodiment, at least one of the polypeptides in a composition of the invention is a fusion protein comprising at least one other polypeptide sequence. The at least one other polypeptide may be, for example, a polypeptide that enhances the stability of a polypeptide of the present invention, or a polypeptide that assists in the purification or detection of the fusion protein, or a polypeptide capable of eliciting an immune response in an animal, especially a human.

In one embodiment, the fusion protein comprises a polypeptide at least 90% identical to MSP-1 (SEQ ID NO:43) or a fragment of at least about 50 amino acids thereof. In a preferred embodiment, the MSP-1 fragment is MSP-1(42) (SEQ ID NO:44) or MSP-1(19) (SEQ ID NO:45).

In another particular embodiment, the fusion protein comprises a Histidine (His) tag.

In a particular embodiment, the composition is an immunogenic composition. In one particular embodiment, the composition is a vaccine.

In a more particular embodiment, the composition comprises an adjuvant and/or pharmaceutically acceptable carrier.

In yet another embodiment, a recombinant polypeptide fragment of the invention is immunogenic.

In another aspect, the present invention provides an isolated and/or exogenous polynucleotide comprising or consisting of:
i) a sequence of nucleotides as set forth in SEQ ID NO:58,
ii) a sequence of nucleotides encoding a recombinant polypeptide fragment of the invention,
iii) a sequence of nucleotides which is at least 70% identical to SEQ ID NO:58, and/or
iv) a sequence which hybridises with any one or more of i) to iii) under at least moderately stringent conditions.

In one embodiment, the isolated and/or exogenous polynucleotide comprises or consists of:
i) a sequence of nucleotides encoding a recombinant polypeptide fragment comprising or consisting of the amino acid sequence set forth in SEQ ID NO:60 and
ii) a sequence of nucleotides encoding a recombinant polypeptide fragment comprising or consisting of the amino acid sequence set forth in SEQ ID NO:64.

In yet another embodiment, the isolated and/or exogenous polynucleotide further comprises:
i) a sequence of nucleotides encoding a recombinant polypeptide fragment comprising or consisting of the amino acid sequence as set forth in SEQ ID NO:36.

In another aspect, there is provided a vector comprising the isolated and/or exogenous polynucleotide of the invention. In a preferred embodiment, the polynucleotide is operably linked to a promoter.

In another aspect, the present invention provides a DNA vaccine comprising the isolated and/or exogenous polynucleotide of the invention and/or the vector of the invention.

In yet another aspect, the present invention provides a host cell comprising a recombinant polypeptide fragment of the invention, a polynucleotide of the invention, and/or a vector of the invention.

In another aspect, the present invention provides a method of making a recombinant polypeptide fragment of the invention, the method comprising:
(a) obtaining an expression vector comprising a polynucleotide sequence of the invention operably linked to a promoter; and
(b) introducing said expression vector into a cell or cell free expression system whereby said cell or cell free expression system produces the recombinant polypeptide fragment encoded by said polynucleotide sequence.

In one embodiment, the method further comprises isolating said recombinant polypeptide fragment.

In another aspect, the present invention provides a substantially purified antibody that specifically binds a recombinant polypeptide fragment of the invention.

In one embodiment, the antibody is detectably labelled.

In another aspect, there is provided a method of treating or preventing malaria in a subject, the method comprising administering to the subject a composition of the invention, a recombinant polypeptide fragment of the invention, a polynucleotide of the invention, a vector of the invention, a host cell of the invention, and/or an antibody of the invention.

In yet another aspect, there is provided a method for raising an immune response in a subject, the method comprising administering to the subject a composition of the invention, a recombinant polypeptide fragment of the invention, a polynucleotide of the invention, a vector of the invention, and/or a host cell of the invention.

In another aspect, the present invention provides a composition of the invention, a recombinant polypeptide fragment of the invention, a polynucleotide of the invention, a vector of the invention, a host cell of the invention, and/or an antibody of the invention for use in the treatment or prevention of malaria.

In another aspect, the present invention provides a non-human transgenic organism comprising an exogenous polynucleotide encoding a recombinant polypeptide fragment of the invention. In one embodiment, the non-human transgenic organism is a bacterium, for example, *E. coli*.

In another embodiment, the non-human transgenic organism is a plant. Preferably, the plant is selected from a fruit, vegetable or cereal.

In yet another aspect, the present invention provides a method of screening for an agonist or antagonist which modulates the activity of a recombinant polypeptide fragment of the invention, the method comprising contacting the recombinant polypeptide fragment with a candidate compound, and determining whether said compound binds the recombinant polypeptide fragment.

In one embodiment, the antagonist prevents a Rip recombinant polypeptide fragment from binding to an Rh5 polypeptide.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE FIGURES

Some figures contain coloured representations or entities. Coloured versions of the figures are available from the Patentee upon request or from an appropriate Patent Office. A fee may be imposed if obtained from a Patent Office.

FIG. 1A-B. Characterisation of processed 45 kDa pfRh5 C-terminal domain. (A) Gel-filtration chromatography of purified pfRh5a. Samples collected (# indicates fraction number) were separated by SDS-PAGE. (B) Blue native gel electrophoresis of purified pfRh5.

FIG. 2A-B. (A) Gel-filtration chromatography of pfRh5 on a Superdex 200 analytical column. Samples collected (# indicates fraction number) were separated by SDS-PAGE. (B) Gel-filtration chromatography of pfRh5 incubated with pfRh5 antibody on a Superdex 200 column. Samples collected (# indicates fraction number) were separated by SDS-PAGE. * indicates IgG heavy and light chains; Arrow indicates pfRh5.

FIG. 3A-C. Generation of C-terminus tagged pfRip parasite line (pfRipHA). (A) Diagram showing that a single Strep-tag and triple Haemaglutinin (HA) tag were added to the C-terminus of pfRip by 3'-single homologous cross-over recombination. (B) Immunoblotting of saponin pellet and HA-tagged protein purified from culture supernatant of pfRipHA line with anti-HA antibody. (C) PfRipHA analysed by SDS-PAGE under reducing and non-reducing conditions.

FIG. 6A-D. The domain structure and expression of PfRip in *P. falciparum*. (A) The domain structure of the PfRip protein. PfRip is 1,086 amino acids with a signal sequence and 10 EGF-like domains. Two are grouped in the N-terminus with a further eight clustered towards the C-terminus. The EGF-like domains are shown as the ellipse-shaped objects. (B) A lineup of the ten EGF-like domains showing the conserved cysteine residues that define these domains. The amino acid residues in PfRip are shown at the left. Also in the alignment is the epidermal growth factor domain. (C) Expression of amino acid residues 791-900 of PfRip as a recombinant protein in *E. coli*. Shown are the protein eluate after Ni— chelate chromatography (lane 1) and size exclusion chromatography (lane 2). (D) Antibodies raised to the PfRip recombinant protein react with PfRip in schizont preparations of *P. falciparum*. Shown are two immunoblots probed with antibodies raised in two rabbits (anti-PfRip/1 and anti-PfRip/2).

FIG. 7A-B. PfRip is a peripheral membrane protein and carries its complex partner pfRh5 onto the surface of merozoites. (A) Immunoblot of soluble and insoluble fractions from pellet prepared by hypotonically lysis of the late schitzont stage PfRipHA parasite infected red blood cells. (B) Immunoblot of saponin pellet prepared from the late schitzont stage pfRipHA parasite-infected red blood cells.

FIG. 8A-D. (A) Pre-incubation of purified merozoites with Protein-A purified rabbit polyclonal antibodies (R1155 & R1156 at 2 mg/ml) raised against recombinant pfRip for 2 minutes at 37° C. inhibited merozoites attachment to uninfected red blood cells by 40-55%. (B) Growth Inhibition assay (GIA) for different strains of *P. falciparum* using anti-PfRIP-1 IgG antibodies. (C) Titration of IgG anti-PfRIP-1 antibodies with FCR3. (D) Titration of IgG anti-PfRIP-1 antibodies with 3D7.

FIG. 9A-B. Antibodies to a C-terminal region of PfRipr inhibit attachment of merozoites to erythrocytes and parasite growth. (A) Anti-PfRipr/1 antibodies inhibit invasion of *P. falciparum* strains into erythrocytes. Shown are growth inhibition assays of the parasite strains FCR3, W2mef, T994, CSL2, E8B, MCAMP, 7G8, D10, HB3 and 3D7. The graph represents three independent experiments done in triplicate with each normalised to the negative control (Protein A purified IgG from normal rabbit serum). The error bars represent standard error of the mean of the three independent experiments. (B) GIA assay using different combinations of antibodies on invasion of the 3D7 strain.

Figure 4:
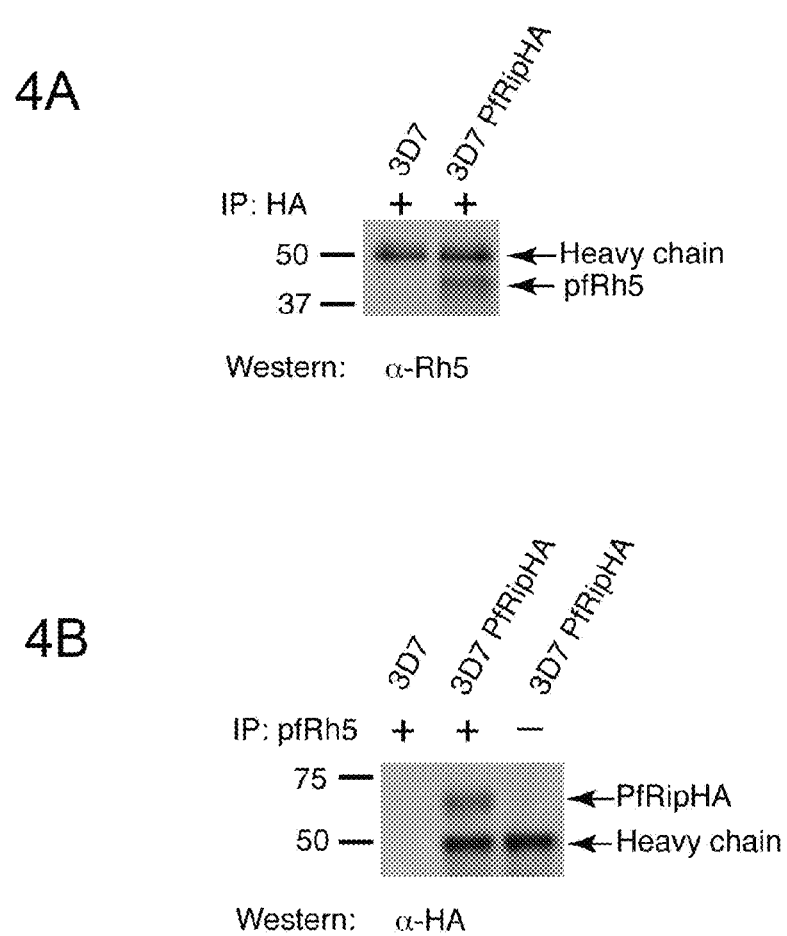
FIG. 4A-B. Reciprocal immunoprecipitation confirm pfRh5 and pfRip form a complex. (A) Immunoblot of protein immunoprecipitated from culture supernatants of 3D7 and 3D7-pfRipHA with anti-HA-Sepharose beads and probed with monoclonal anti-pfRh5 antibody. (B) Immunoprecipitation of culture supernatants from both wt 3D7 and 3D7-pfRipHA parasite lines with monoclonal anti-pfRh5 antibody coupled to Mini-bead.

Shown are IgG antibodies: αPfRIP/1, αPfRIP/2, αPfRIP/1+αEBA-175, αPfRIP/1+αPfRh4, αPfRIP/1+αPfRh2a/b and αPfRIP/1+αPfRh2a/b+αPfRh4 (shown as αPfRIP/1+αPfRh2a/b/PfRh4).

FIG. 10A-B. Recombinant rRh2$_{15}$ binds erythrocytes. (A) Schematic diagram of the PfRh2 protein showing the location of the rRh2$_{15}$ and 2b1 fusion proteins. The rRh2$_{15}$ is located within the 85 kDa binding domain of PfRh2. The processing event leading to the 85 kDa product is indicated by the arrow. The 2b1 fusion protein is from a Rh2b unique region at the C-terminus of the protein. The regions of the protein in black at the N and C-termini represent the signal sequence and transmembrane domains respectively. (B) Recombinant rRh2$_{15}$ was bound to untreated (Unt.), Low trypsin (LowT; 0.067 mg/ml), High Trypsin (HighT; 1 mg/ml), neuraminidase (N) or chymotrypsin-treated (C) erythrocytes. Bound proteins were eluted with 1.5M NaCl, separated on SDS-PAGE gels, Western blotted and probed with an antibody (R1170) to the rRh2$_{15}$ fusion protein. Recombinant rRh2$_{15}$ binding to erythrocytes was partially sensitive to neuraminidase and chymotrypsin, but resistant to both Low and High Trypsin concentrations. Unbound proteins removed from the Untreated erythrocytes are also shown. The 2b1 fusion protein was bound to untreated erythrocytes. Bound proteins were eluted with 1.5M NaCl, separated on SDS-PAGE gels, Western blotted and probed with the 4B7 antibody raised to the 2b1 fusion protein. The 2b1 fusion protein showed no binding to Untreated erythrocytes but was clearly present in the Unbound fraction.

FIG. 11A-D. Antibodies to rRh2$_{15}$ block native PfRh2 binding and invasion. (A) R1170 antibodies made to rRh2$_{15}$ block binding of native PfRh2 to erythrocytes. Protein G-purified R1070, R1170 or normal rabbit serum antibodies at final concentrations from 0.1 to 1.0 µg/µl were preincubated with 3D7 culture supernatant before adding Untreated erythrocytes. Bound proteins were eluted with 1.5M NaCl, separated on SDS-PAGE gels, Western blotted and probed with an antibody (6F12) to the 85 kDa PfRh2 binding domain. Only antibodies to the rRh2$_{15}$ (R1170) block binding of native PfRh2 to erythrocytes. Antibodies to another region of the 85 kDa binding domain and normal rabbit serum antibodies do not block binding. (B) R1170 antibodies block binding of rRh2$_{15}$ to erythrocytes. Protein G-purified R1170 antibodies at final concentrations from 0.03 to 0.5 µg/µl were pre-incubated with 0.5 µg rRh2$_{15}$ fusion protein before adding Untreated erythrocytes. Bound proteins were eluted with 1.5 M NaCl, separated by SDS-PAGE, Western blotted and probed with Protein G-purified R1170. (C) Antibodies to rRh2$_{15}$ block invasion of both untreated and Low trypsin-treated erythrocytes. Protein G-purified IgG at 2 mg/ml final concentration from both R1070 and R1170 pre-bleeds and kill bleed sera were added to 3D7 parasites at the trophozoite stage together with target erythrocytes that were untreated or Low trypsin (0.067 mg/ml)-treated. Following reinvasion in the presence of antibodies, cultures were continued to the trophozoite stage, when parasite numbers were determined in order to see the effect of antibodies on invasion. Percent invasion in the absence of antibodies was adjusted to 100% invasion. Experiments were done at least twice in triplicate. Error bars show the standard error of the mean. (D) Antibodies to rRh2$_{15}$ block invasion of PfRh2b but not Rh2a in 3D7 parasites. Protein G-purified IgG from R1170 kill bleed serum at 2 mg/ml final concentration was added to 3D7Δ2a (express Rh2b only), 3D7Δ2b (express Rh2a only) and FCR3 (express neither Rh2a nor Rh2b) parasites at the trophozoite stage together with target erythrocytes that were untreated or treated with 0.03 mg/ml Trypsin. Other details of the experiments were the same as in (C) above.

Figure 12:
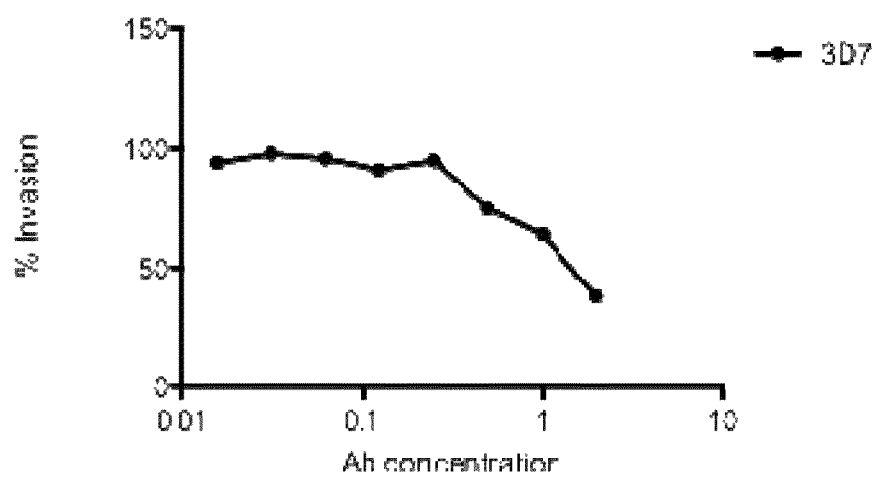

FIG. 12. Antibodies against a combination of antigens inhibit invasion of P. falciparum into human red blood cells in vitro. Percentage invasion is calculated as 100×(mean invasion (triplicate wells) of control IgG/test IgG).

FIG. 13. Nucleic and amino acid sequences of synthetic PfRip (amino acids 604-1086 of SEQ ID NO: 2), designated herein SEQ ID NO: 58 (nucleic acid coding strand), SEQ ID NO: 59 (nucleic acid non-coding strand), and SEQ ID NO: 60 (amino acid sequence).

FIG. 14. Amino acid sequence of synthetic EBA175 fragment (amino acid 761-1298 of SEQ ID NO: 35), designated herein SEQ ID NO: 64.

FIG. 15. Results from the growth inhibition assay using anti-RIP/2 antiserum are shown against different parasite strains. All samples were tested in triplicate.

FIG. 16A-E. Antibodies raised against recombinant fragments of Plasmodium polypeptides inhibit invasion of different parasite strains in a single cycle growth inhibition assay (GIA). IgG raised against EBA-175 amino acids 761-1298 (A), PfRH5 (B), PfRIP amino acids 604-1086 (C) and a triple antigen cocktail (D) are inhibitory against 3D7, W2mef and FCR3 parasites. (E) Median growth inhibition (line), 95% confidence intervals (CI) (box) and minimum and maximum GIA (error bars) for IgG against EBA-175, PfRH5 and PfRIP at 2 mg/ml against 3D7, W2mef and FCR3 parasites. All samples were tested in triplicate.

KEY TO THE SEQUENCE LISTING

SEQ ID NO:1—pfRip coding sequence
SEQ ID NO:2—pfRip amino acid sequence
SEQ ID NO:3—pfRip antigenic fragment 791-900
SEQ ID NO:4—pfRip antigenic fragment 238-368
SEQ ID NO:5—pfRip peptide 93-100
SEQ ID NO:6—pfRip peptide 101-114
SEQ ID NO:7—pfRip peptide 699-708
SEQ ID NO:8—pfRip peptide 760-769
SEQ ID NO:9—pfRip peptide 963-972
SEQ ID NO:10—pfRh1 amino acid sequence
SEQ ID NO:11—pfRh2a amino acid sequence
SEQ ID NO:12—pfRh2a/b 15 kDa antigenic fragment
SEQ ID NO:13—pfRh2a/b antigenic fragment 2030-2528
SEQ ID NO:14—pfRh2b amino acid sequence
SEQ ID NO:15—pfRh4 amino acid sequence
SEQ ID NO:16—pfRh4 antigenic fragment 28-766
SEQ ID NO:17—pfRh5 amino acid sequence
SEQ ID NO:18—pfRh5 antigenic fragment (minus leader sequence)
SEQ ID NO:19—pfRh5 antigenic fragment
SEQ ID NO:20—pfRh5 antigenic fragment
SEQ ID NO:21—pfRh5 antigenic fragment
SEQ ID NO:22—pfRh5 antigenic fragment
SEQ ID NO:23—pfRh5 antigenic fragment
SEQ ID NO:24—pfRh5 antigenic fragment
SEQ ID NO:25—pfRh5 antigenic fragment
SEQ ID NO:26—pfRh5 antigenic fragment
SEQ ID NO:27—pfRh5 antigenic fragment
SEQ ID NO:28—pfRh5 antigenic fragment
SEQ ID NO:29—pfRh5 peptide 187-197
SEQ ID NO:30—pfRh5 peptide 212-221
SEQ ID NO:31—pfRh5 peptide 237-247
SEQ ID NO:32—pfRh5 peptide 303-310
SEQ ID NO:33—pfRh5 peptide 358-366
SEQ ID NO:34—pfRh5 peptide 437-443
SEQ ID NO:35—pfEBA175 amino acid sequence SEQ ID NO:36—pfEBA175 antigenic fragment 760-1271
SEQ ID NO:37—pfEBA181 amino acid sequence
SEQ ID NO:38—pfEBA140 amino acid sequence
SEQ ID NO:39—pfRip 238-368 codon optimised
SEQ ID NO:40—pfRip 791-900 forward primer
SEQ ID NO:41—pfRip 791-900 reverse primer
SEQ ID NO:42—pfRh2a/b 15 kDa DNA sequence
SEQ ID NO:43—MSP-1 amino acid sequence
SEQ ID NO:44—MSP-1(42) amino acid sequence
SEQ ID NO:45—MSP-1(19) amino acid sequence
SEQ ID NOs:46 to 57—Peptide linkers
SEQ ID NOs:58 and 59—nucleic acid sequence (coding and non-coding strands, respectively) encoding pfRip antigenic fragment 604-1086
SEQ ID NO:60—pfRip antigenic fragment 604-1086
SEQ ID NO: 61—N-terminal 6-Histidine (HIS)+FLAG tags, including a TEV cleavage site
SEQ ID NO:62—N-terminal 6-HIS tag (*E. coli*)
SEQ ID NO:63—C-terminal tag sequence (*E. coli*)
SEQ ID NO:64—pfEBA175 antigenic fragment 761-1298

DETAILED DESCRIPTION

General Techniques and Selected Definitions

Unless specifically defined otherwise, all technical and scientific terms used herein shall be taken to have the same meaning as commonly understood by one of ordinary skill in the art (e.g., in immunology, protein chemistry, biochemistry, cell culture, microbiology, and molecular genetics).

Unless otherwise indicated, the immunological, microbiological and molecular genetic techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, 3$^{rd}$ ed., Cold Spring Harbour Laboratory Press (2001), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al., (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

As used herein, the term "subject" refers to an animal, e.g., a mammal. In one embodiment, the subject is a human.

"Administering" as used herein is to be construed broadly and includes administering a composition or polypeptide as described herein to a subject as well as providing a composition or polypeptide as described herein to a cell.

As used herein the terms "treating", "treat" or "treatment" include administering a therapeutically effective amount of a composition, polypeptide, polynucleotide, vector, cell and/or antibody the invention sufficient to reduce the severity of or eliminate at least one symptom of malaria in a subject such as prostration, impaired consciousness, respiratory distress (acidotic breathing), multiple convulsions, circulatory collapse, pulmonary oedema (radiological), abnormal bleeding, jaundice, and/or haemoglobinuria.

The term "preventing" refers to protecting a subject from developing at least one symptom of malaria, or delaying the onset of a symptom of malaria in a subject.

Polypeptides and Antigenic Fragments

The terms "polypeptide" and "protein" as used herein are generally used interchangeably and refer to a polypeptide chain which may or may not be modified by addition of non-amino acid groups. Thus, the protein may be glycosylated, unglcosylated, and/or may contain other molecules fused, linked, bound or otherwise associated to the protein such as amino acids, lipids, carbohydrates or other polypeptides. It would be understood that such polypeptide chains may associate with other polypeptides or proteins or other molecules such as co-factors. The terms "proteins" and "polypeptides" as used herein also include variants, mutants, biologically active fragments, modifications, analogous and/or derivatives of the polypeptides described herein.

By "isolated polypeptide" we mean a polypeptide that has generally been separated from the lipids, nucleic acids, other peptides, and other contaminating molecules with which it is associated in its native state. Preferably, the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. More preferably, the query sequence is at least 250 amino acids in length and the GAP analysis aligns the two sequences over a region of at least 250 amino acids. More preferably, the query sequence is at least 500 amino acids in length and the GAP analysis aligns the two sequences over a region of at least 500 amino acids. More preferably, the two sequences are aligned over their entire length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics, for example immunogenicity.

Mutant (altered) polypeptides can be prepared using any suitable technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include orthologous genes from closely related species. Products derived from mutated/altered DNA can readily be screened using techniques described herein to determine if they possess desired characteristics.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Amino acids are preferably substituted in a relatively conservative manner. Such conservative substitutions are shown in Table 1 under the heading of "exemplary substitutions".

TABLE 1

| Exemplary substitutions. | |
| --- | --- |
| Original Residue | Exemplary Substitutions |
| Ala (A) | Val; Leu; Ile; Gly |
| Arg (R) | Lys |
| Asn (N) | Gln; His |
| Asp (D) | Glu |
| Cys (C) | Ser |

TABLE 1-continued

| Exemplary substitutions. | |
| --- | --- |
| Original Residue | Exemplary Substitutions |
| Gln (Q) | Asn; His |
| Glu (E) | Asp |
| Gly (G) | Pro, Ala |
| His (H) | Asn; Gln |
| Ile (I) | Leu; Val; Ala |
| Leu (L) | Ile; Val; Met; Ala; Phe |
| Lys (K) | Arg |
| Met (M) | Leu; Phe |
| Phe (F) | Leu; Val; Ala |
| Pro (P) | Gly |
| Ser (S) | Thr |
| Thr (T) | Ser |
| Trp (W) | Tyr |
| Tyr (Y) | Trp; Phe |
| Val (V) | Ile; Leu; Met; Phe, Ala |

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or immunogenicity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a host cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The terms "antigen", "antigenic", "antigenic fragment" and the like are well understood in the art and refer to the portion of a macromolecule, for example a polypeptide defined herein, which is specifically recognized by a component of the immune system, for example, an antibody or a T-cell antigen receptor. The term "antigen" therefore refers to a peptide, a polypeptide, or other macromolecule to which an immune response can be induced in a host. Thus, the invention includes an antigenic fragment of a polypeptide defined herein. Preferably, the antigenic fragment is capable of raising an immune response against a pathogen of the genus *Plasmodium*, for example *Plasmodium falcparum*, *Plasmodium vivax*, *Plasmodium ovale curtisi*, *Plasmodium ovale wallikeri*, *Plasmodium malariae*, and/or *Plasmodium knowlesi*. In one embodiment, the antigenic fragment is 6 amino acids in length, more preferably 7 amino acids in length, more preferably 8 amino acids in length, more preferably 9 amino acids in length, more preferably at least 10 amino acids in length. Alternatively the antigenic fragment is at least 20, 30, 40, 50, 60, 70, 80, 90, 100 or more amino acids in length. In an embodiment, the antigenic fragment when administered to a subject is able to elicit an immune response against at least one polypeptide comprising an amino acid sequence as provided in any one of SEQ ID NOs:2 to 4, 10 to 28 or 35 to 38. Further examples of antigenic fragments useful for the invention are described in WO 2010/022452, US 2009/0175895 and US 2009/0202579, some of which are outlined in further detail below.

Rip

In a particularly preferred embodiment, a composition of the invention comprises a Rip polypeptide, or antigenic fragment thereof. An example of an *P. falciparum* Rip polypeptide is provided as SEQ ID NO:2. It is known to the skilled person that there are a large number of single nucleotide polymorphism in Rip and these and any other mutations are included within the scope of the invention. Particular polymorphisms include changes to amino acids N144 to K, V190 to A, H511 to R, L673 to V, A755 to G, Y985 to N, and/or I1039 to M.

In a particularly preferred embodiment, the Rip antigenic fragment comprises, more preferably consists of, EGF domains 5 and 6 of the group of 8 EGF domains (see FIG. 6A), such as i) an amino acid sequence as set forth in SEQ ID NO:3, ii) an amino acid sequence which is at least 70% identical to SEQ ID NO:3, and/or iii) an antigenic fragment of i) or ii).

Examples of other RIP antigenic fragments include those comprising or consisting of, one, preferably two or more, and up to all 8 (such as about amino acid 636 to about amino acid 979) of the EGF domains towards the C-terminal end of pfRip (see FIGS. 6A and 6B).

Yet another exemplary Rip antigenic fragment comprises or consists of amino acids 604-1086 of pfRip (SEQ ID NO:2). The pfRip fragment spanning amino acids 604-1086 of pfRip is designated herein as SEQ ID NO:60.

In another particular embodiment, the Rip antigenic fragment comprises, more preferably consists of, i) an amino acid sequence as set forth in SEQ ID NO:60, ii) an amino acid sequence which is at least 70% identical to SEQ ID NO:60, and/or iii) an antigenic fragment of i) or ii).

Rh1

In an embodiment, a composition of the invention comprises or consists of an Rh1 polypeptide, or antigenic fragment thereof. An example of an *P. falciparum* Rh1 polypeptide is provided as SEQ ID NO:10. It is known to the skilled person that there are a large number of single nucleotide polymorphism in Rh1 and these and any other mutations are included within the scope of the invention.

In one embodiment, the antigenic fragment comprises or consists of the region between about amino acid residue 1 to the transmembrane domain of Rh1.

Rh2a

In an embodiment, a composition of the invention comprises or consists of an Rh2a polypeptide, or antigenic fragment thereof. An example of an *P. falciparum* Rh2a polypeptide is provided as SEQ ID NO:11. It is known to the skilled person that there are a large number of single nucleotide polymorphism in Rh2a and these and any other mutations are included within the scope of the invention. Examples of such mutations are whereby A at amino acid 2546 is replaced with D, E at amino acid 2613 is replaced with G, R at amino acid 2723 is replaced with K, or K at amino acid 2725 replaced with Q.

In one embodiment, the antigenic fragment of Rh2a comprises or consists of the region between about 31 amino acids N-terminal of the Prodom PD006364 homology region to about the transmembrane domain of Rh2a. The antigenic fragment may also comprise or consist of the region from about residue 2133 to about residue 3065, the region from about residue 2098 to about residue 2597, or the region from about residue 2616 to about residue 3115, of Rh2a.

In a particularly preferred embodiment, the Rh2a antigenic fragment comprises, more preferably consists of, i) an amino acid sequence as set forth in SEQ ID NO:12, ii) an amino acid sequence which is at least 70% identical to SEQ ID NO:12, and/or iii) an antigenic fragment of i) or ii).

In another particularly preferred embodiment, the Rh2a antigenic fragment comprises, more preferably consists of, i) an amino acid sequence as set forth in SEQ ID NO:13, ii) an amino acid sequence which is at least 70% identical to SEQ ID NO:13, and/or iii) an antigenic fragment of i) or ii).

Rh2b

In an embodiment, a composition of the invention comprises or consists of an Rh2b polypeptide, or antigenic fragment thereof. An example of an *P. falciparum* Rh2a polypeptide is provided as SEQ ID NO:14. It is known to the skilled person that there are a large number of single nucleotide polymorphism in Rh2b and these and any other mutations are included within the scope of the invention. Examples of such mutations are whereby D at amino acid 2546 is replaced with A, K at amino acid 2635 is replaced with E, K at amino acid 3165 is replaced with N, or N at amino acid 3191 replaced with T or Y.

In one embodiment, the antigenic fragment of Rh2b comprises or consists of the region between about 31 amino acids N-terminal of the Prodom PD006364 homology region to about the transmembrane domain of Rh2b. The antigenic fragment may comprise or consist of the region from about residue 2027 to about residue 3115, more particularly from about residue 2027 to about residue 2533, of Rh2b. In other examples, the antigenic fragment may comprise or consist of the region from about residue 2098 to about residue 2597, or the region from about 2616 to 3115, of Rh2b.

In a particularly preferred embodiment, the Rh2b antigenic fragment comprises, more preferably consists of, i) an amino acid sequence as set forth in SEQ ID NO:12, ii) an amino acid sequence which is at least 70% identical to SEQ ID NO:12, and/or iii) an antigenic fragment of i) or ii).

In another particularly preferred embodiment, the Rh2b antigenic fragment comprises, more preferably consists of,
i) an amino acid sequence as set forth in SEQ ID NO:13,
ii) an amino acid sequence which is at least 70% identical to SEQ ID NO:13, and/or
iii) an antigenic fragment of i) or ii).

Rh4

In an embodiment, a composition of the invention comprises or consists of an Rh4 polypeptide, or antigenic fragment thereof. An example of an *P. falciparum* Rh4 polypeptide is provided as SEQ ID NO:15. It is known to the skilled person that there are a large number of single nucleotide polymorphism in Rh4 and these and any other mutations are included within the scope of the invention. Examples of such mutations are whereby Y at amino acid 12 is replaced with A, L at amino acid 143 is replaced with I, N at amino acid 435 is replaced with K, Q at amino acid 438 is replaced with K, T at amino acid 506 replaced with K, N at amino acid 771 is replaced with S, N at amino acid 844 is replaced with I, K at amino acid 1482 is replaced with R, or N at amino acid 1498 is replaced with I.

In one embodiment, the antigenic fragment of Rh2b comprises or consists of the region from about the MTH1187/YkoF-like superfamily domain to about the transmembrane domain of Rh4. The antigenic fragment may comprise or consist of the region from about residue 1160 to about residue 1370 of Rh4.

In another particularly preferred embodiment, the Rh4 antigenic fragment comprises, more preferably consists of,
i) an amino acid sequence as set forth in SEQ ID NO:16,
ii) an amino acid sequence which is at least 70% identical to SEQ ID NO:16, and/or
iii) an antigenic fragment of i) or ii).

Rh5

In an embodiment, a composition of the invention comprises or consists of an Rh5 polypeptide, or antigenic fragment thereof. An example of an *P. falciparum* Rh5 polypeptide is provided as SEQ ID NO:17. It is known to the skilled person that there are a large number of single nucleotide polymorphism in Rh5 and these and any other mutations are included within the scope of the invention. Examples of such mutations are whereby E at amino acid 48 is replaced with K, Y at amino acid 147 is replaced with H, H at amino acid 148 is replaced with N, S at amino acid 197 is replaced with Y, C at amino acid 203 is replaced with Y, I at amino acid 204 is replaced with K or R, N at amino acid 347 is replaced with Y or D, Y at amino acid 358 is replaced with F, E at amino acid 362 is replaced with D, V at amino acid 371 is replaced with I, I at amino acid 407 is replaced with V, I at amino acid 410 is replaced with M, or K at amino acid 429 is replaced with N.

In one embodiment, the antigenic fragment lacks the 23 amino acid N-terminal leader sequence (SEQ ID NO:18). In alternate embodiments, the antigenic fragment may comprise or consist of one of the amino acid sequences provided as SEQ ID NO:19 to SEQ ID NO:28, or variants thereof such as where one or more of the above-mentioned mutations of Rh5 are present. In further embodiments, the antigenic fragment may comprise or consist of residues from about residue 203 to about residue 224, 317, 329, 345, or 351; or residues from about residue 224 to about residue 317, 329, 345, or 351; or residues from about residue 329 to about residue 345 or 351, or residues from about residue 345 to about residue 351. In one embodiment, cysteines 203 (polymorphic in *P. falciparum*) and 329 (absent in *P. reichenowi*) pair in the molecule by way of disulfide bridge to form a loop. Accordingly, in one form of the invention the antigenic fragment may comprise or consist of amino acid residues from about residue 203 to about residue 329. It is further proposed that cysteines 224 and 317 pair with either cysteine 345 or cysteine 351, such that the antigenic fragment may comprise or consist of residues from about residue 224 to about residue 345 or 351; or from about residue 317 to about residue 345 or 351.

EBA175

In a further embodiment, a composition of the invention comprises or consists of EBA175, or antigenic fragment thereof. An example of an *P. falciparum* EBA175 polypeptide is provided as SEQ ID NO:35. It is known to the skilled person that there are a large number of single nucleotide polymorphism in EBA175 and these and any other mutations are included within the scope of the invention. Examples of such mutations are whereby N at amino acid 157 replaced with S, E at amino acid 274 replaced with K, K at amino acid 279 replaced with E, K at amino acid 286 replaced with E, D at amino acid 336 replaced with Y, K at amino acid 388 replaced with N, P at amino acid 390 replaced with S, E at amino acid 403 replaced with K, K at amino acid 448 replaced with E, K at amino acid 478 replaced with N K at amino acid 481 replaced with I, N at amino acid 577 replaced with K, Q at amino acid 584 replaced with K, R at amino acid 664 replaced with S, S at amino acid 768 replaced with N, E at amino acid 923 replaced with K, K at amino acid 932 replaced with E, E at amino acid 1058 replaced with V, or G at amino acid 1100 replaced with D.

In one embodiment, the antigenic fragment is found in the region between the F2 domain and the transmembrane domain of the EBA175 protein.

In a particularly preferred embodiment, the EBA175 antigenic fragment comprises, more preferably consists of,
i) an amino acid sequence as set forth in SEQ ID NO:36,
ii) an amino acid sequence which is at least 70% identical to SEQ ID NO:36, and/or
iii) an antigenic fragment of i) or ii).

In another particular embodiment, the EBA175 antigenic fragment comprises, more preferably consists of,
i) an amino acid sequence as set forth in SEQ ID NO:64,
ii) an amino acid sequence which is at least 70% identical to SEQ ID NO:64, and/or
iii) an antigenic fragment of i) or ii).

EBA181

In a further embodiment, a composition of the invention comprises or consists of EBA181, or antigenic fragment thereof. An example of an *P. falciparum* EBA181 polypeptide is provided as SEQ ID NO:37. It is known to the skilled person that there are a large number of single nucleotide polymorphism in EBA181 and these and any other mutations are included within the scope of the invention. Examples of such mutations are whereby V at amino acid 64 replaced with L, Q at amino acid 364 replaced with H, V at amino acid 363 replaced with D, R at amino acid 358 replaced with K, N at amino acid 414 replaced with I, K at amino acid 443 replaced with Q, P at amino acid 878 replaced with Q, E at amino acid 884 replaced with Q, E at amino acid 1885 replaced with K, Q at amino acid 890 replaced with E, P at amino acid 1197 replaced with L, K at amino acid 1219 replaced with N, D at amino acid 1433 replaced with Y or N, or K at amino acid 1518 replaced with E.

In one embodiment, the antigenic fragment is found in the region between the F2 domain and the transmembrane domain of the EBA181 protein. The antigenic fragment may comprise or consist of the region from about residue 755 to about residue 1339 of EBA181.
EBA140

In a further embodiment, a composition of the invention comprises or consists of EBA140, or antigenic fragment thereof. An example of an *P. falciparum* EBA140 polypeptide is provided as SEQ ID NO:38. It is known to the skilled person that there are a large number of single nucleotide polymorphism in EBA140 and these and any other mutations are included within the scope of the invention. Examples of such mutations are whereby V at amino acid 19 replaced with I, L at amino acid 112 replaced with F, I at amino acid 185 replaced with V, N at amino acid 239 replaced with S, K at amino acid 261 replaced with T.

In one embodiment, the antigenic fragment is found in the region between the F2 domain and the transmembrane domain of the EBA140 protein. The antigenic fragment may comprise or consist of the region from about residue 746 to about residue 1045 of EBA140.

Fusion Proteins

In one embodiment, a composition of the invention comprises a polypeptide which is a fusion protein comprising at least one other polypeptide sequence. The at least one other polypeptide may be, for example, a polypeptide that enhances the stability of a polypeptide of the present invention, or a polypeptide that assists in the purification or detection of the fusion protein, or preferably a polypeptide capable of eliciting an immune response in an animal, especially a human. By way of non-limiting example, the at least one other polypeptide sequence may comprise one or more T cell epitopes for recruitment of T helper cells or activation of cytotoxic T cells, or one or more antigens, cytokines and/or chemokines.

In an embodiment, the at least one other polypeptide is a polypeptide from *Plasmodium falciparum*. Preferably, the at least one other polypeptide from *Plasmodium falciparum* comprises one or more T cell epitopes for recruitment of T helper cells, and/or one or more MHC class I or MHC class II motifs. Methods for the identification of T cell epitopes and MHC class I and MHC class II motifs are known in the art and described in, for example, Rammensee (1995), Ohta et al. (1998), and Singh et al. (2010).

In one particular embodiment, the at least one other polypeptide is merozoite surface protein-1 (MSP-1) or a fragment of at least 50 amino acids thereof. An example of MSP-1 is provided as SEQ ID NO:43 (GenBank Accession No. BAF62268.1 and related molecules). Examples of MSP-1 fragments include MSP-1(42) provided as SEQ ID NO:44 and MSP-1(19) provided as SEQ ID NO:45.

In addition, the fusion protein may comprise one or more linkers or spacers. A "linker" or "spacer" as used herein refers to a peptide, polypeptide or other molecule, for example a straight or branched-chain carbon linker or heterocyclic carbon linker, that may be included between two polypeptides in a fusion protein to enhance expression of the protein in a bacterial or eukaryotic cell or to decrease steric hindrance such that one or more of the polypeptides in the fusion protein may assume its desired tertiary structure and/or interact appropriately with its target molecule, such as, for example, a B cell receptor or T cell receptor. Thus, the fusion protein may comprise one or more spacers before, after, or between one or more polypeptide domains in the fusion polypeptide. Suitable linkers are well known to those of skill in the art and include, but are not limited to, straight or branched-chain carbon linkers, heterocyclic carbon linkers, or peptide linkers. For spacers and methods of identifying desirable spacers, see, for example, George, et al. (2003).

In one embodiment, the spacer comprises one or more amino acid sequences that are between 1-50 amino acid residues in length, or about 1-25 residues, or about 5-15 residues in length.

Non-limiting examples of peptide linkers include AAA, GGG, SGG, GGSGGS (SEQ ID NO:46), SAT, PYP, PSPSP (SEQ ID NO:47), ASA, ASASA (SEQ ID NO:48), PSPSP (SEQ ID NO:49), KKKK (SEQ ID NO:50), RRRR (SEQ ID NO:51), GGGG (SEQ ID NO:52), GGGGS (SEQ ID NO:53), GGGGS GGGGS (SEQ ID NO:54), GGGGS GGGGS GGGGS (SEQ ID NO:55), GGGGS GGGGS GGGGS GGGGS (SEQ ID NO:56), and GGGGS GGGGS GGGGS GGGGS GGGGS GGGGS (SEQ ID NO:57).

As known in the art, various chemical groups may be incorporated in the spacer segment instead of amino acids. Examples are described in U.S. Pat. No. 5,910,300. In one embodiment the spacer is comprised of an aliphatic chain optimally interrupted by heteroatoms, for example a $C_2$-$C_6$ alkylene, or $=N-(CH_2)_{2-6}-N=$. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydroxyphobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A spacer may also contain repeating short aliphatic chains, such as polypropylene, isopropylene, butylene, isobutylene, pentamethlyene, and the like, separated by oxygen atoms.

Antibodies

The term "antibody" as used in this invention includes polyclonal, monoclonal, chimeric and humanised antibodies, and includes intact molecules as well as molecules comprising or consisting of fragments thereof, such as Fab, F(ab')2, and Fv which are capable of binding an epitopic determinant. Thus, antibodies may exist as intact immunoglobulins, or as modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light and heavy chain variable regions, or Fd fragments containing the heavy chain variable region and the CH1 domain. A scFv consisting of the variable regions of the heavy and light chains linked together to form a single-chain antibody and oligomers of scFvs such as diabodies and triabodies are also encompassed by the term "antibody". As outlined above, also encompassed are fragments of antibodies such as Fab, (Fab')$_2$ and FabFc$_2$ fragments which contain the variable regions and parts of the constant regions. CDR-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit, chicken or rat) or human origin or may be chimeric or humanized.

The antibodies may be Fv regions comprising a variable light ($V_L$) and a variable heavy ($V_H$) chain. The light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

As used herein, the term "specifically binds" shall be taken to mean a protein of the invention reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". Generally, but not necessarily, reference to binding means specific binding, and each term shall be understood to provide explicit support for the other term.

The antibody may be detectably labelled, such as for example, labelled with a fluorescent label (e.g. FITC or Texas Red), radiolabel, or an enzyme (e.g. horseradish peroxidase (HRP)), alkaline phosphatase (AP) or β-galactosidase.

A variety of immunoassay formats may be used to select antibodies specifically immunoreactive with the polypeptides of the invention. For example, surface labelling and flow cytometric analysis or solid-phase ELISA immunoassays are routinely used to select antibodies specifically immunoreactive with a protein or carbohydrate. See Harlow & Lane (supra) for a description of immunoassay formats and conditions that can be used to determine specific immunoreactivity.

Polynucleotides

By "isolated polynucleotide" we mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

"Polynucleotide" as used herein refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

The % identity of a polynucleotide is determined by GAP (Needleman and Wunsch, 1970) analysis (GCG program) with a gap creation penalty=5, and a gap extension penalty=0.3. The query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. Even more preferably, the query sequence is at least 300 nucleotides in length and the GAP analysis aligns the two sequences over a region of at least 300 nucleotides. More preferably, the two sequences are aligned over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 40%, more preferably at least 45%, more preferably at least 50%, more preferably at least 55%, more preferably at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis or DNA shuffling on the nucleic acid as described above). It is thus apparent that polynucleotides of the invention can be either naturally occurring or recombinant.

Polynucleotides of the invention include those which hybridize under stringent conditions to a polynucleotide comprising a sequence of nucleotides which is at least 50% identical, preferably at least 70% identical, more preferably at least 90% identical, to SEQ ID NO:1, SEQ ID NO:39 or SEQ ID NO:42. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, "moderately stringent" hybridization conditions, as used herein, can refer to hybridization at 20° C. to 64° C. in 3.5×SSC, 0.1% w/v SDS, and "high stringency" conditions can refer to hybridization at 65° C. in 0.2×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA.

Vectors and Host Cells

One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and may be a transposon, a virus or a plasmid.

"Operably linked" as used herein refers to a functional relationship between two or more nucleic acid (e.g., DNA) segments. Typically, it refers to the functional relationship of a transcriptional regulatory element to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, expression vectors of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Recombinant molecules may also include intervening and/or untranslated sequences surrounding and/or within the nucleic acid sequences of nucleic acid molecules of the present invention.

Another embodiment of the present invention includes a host cell comprising one or more recombinant molecules of the present invention. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include animal, plant, bacterial, fungal (including yeast), parasite, and arthropod cells. Preferably, the host cell is a bacterial cell, for example *E. coli*.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Compositions and Administration

The present invention provides compositions comprising the polypeptide, including antigenic fragments, defined herein. In one embodiment, the composition is an immunogenic composition. An "immunogenic composition" refers to a composition that comprises materials that elicit a desired immune response and includes a "vaccine". The term "vaccine" covers any composition that induces an at least partially protective immune response against a targeted pathogen or which efficaciously protects against the pathogen; for instance, after administration or injection into the subject (for example, a mammal such as a human), elicits an at least partially protective immune response against the targeted pathogen or provides efficacious protection against the pathogen (e.g., *Plasmodium falciparum*). By inducing an "at least partially protective" immune response it is meant that a vaccine reduces infection and/or reduces at least one symptom caused by infection with a pathogen expressing at least one polypeptide as defined herein.

An immunogenic composition may select, activate or expand cells of the immune system including memory B and T cells to, for example, enable the elimination of infectious agents, such as pathogens expressing at least one polypeptide as defined herein.

In some embodiments, an immunogenic composition includes a suitable carrier, such as an adjuvant, which is an agent that acts in a non-specific manner to increase the immune response to a specific antigen, or to a group of antigens, enabling the reduction of the quantity of antigen in any given dose, or the reduction of the frequency of dosage required to generate the desired immune response. A desired immune response may include, for example, full or partial protection against infection by a *Plasmodium* species or full or partial protection from developing one or more symptoms of malaria. For example, a desired immune response may include any value from between 10% to 100%, e.g., 10%, 20%, 30%, 40%, 50%, 60%, 70%, 80%, 90%, 100%, protection against infection by *Plasmodium* in a vaccinated subject when compared to a non-vaccinated subject.

Adjuvants are useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention further comprise an adjuvant. Examples of chemical compounds that can be used as adjuvants include, but are not limited to aluminum compounds (e.g., alum, aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12), saponin-based adjuvants (for example as described in Sun et al. (2009)) and CARBOPOL®. Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Specific adjuvants include MPL, adjuvants from GSK's Adjuvant Systems such as the AS range, eg. AS01, AS02, AS03, AS04, AS15, fractionss from *Quillaja saponaria* such as QH-B fraction, QS-7, QS-17, QS-18 and QS-21 fractions (Antigenics, New York, N.Y.). Further details regarding suitable adjuvants are provided in the following passages.

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. (e.g. see chapters 8 & 9 of Powell & Newman (eds.) Vaccine Design (1995) Plenum), or mixtures of different mineral compounds, with the compounds taking any suitable form (e.g. gel, crystalline, amorphous, etc.), and with adsorption being preferred. The mineral containing compositions may also be formulated as a particle of metal salt (WO 00/23105).

A typical aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

Oil emulsion compositions suitable for use as adjuvants in the invention include oil-in-water emulsions and water-in-oil emulsions.

A submicron oil-in-water emulsion may include squalene, Tween 80, and Span 85 e.g. with a composition by volume of about 5% squalene, about 0.5% polysorbate 80 and about 0.5% Span 85 (in weight terms, 4.3% squalene, 0.5% polysorbate 80 and 0.48% Span 85), known as 'MF595' (57-59 chapter 10 of Powell & Newman (eds.) Vaccine Design (1995) Plenum; chapter 12 of O'Hagen (ed.) Vaccine Adjuvants: Preparation Methods and Research Protocols (Volume 42 of Methods in Molecular Medicine series)). The MF59 emulsion advantageously includes citrate ions e.g. 10 mM sodium citrate buffer.

An emulsion of squalene, a tocopherol, and Tween 80 can be used. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene tocopherol is preferably <1 as this provides a more stable emulsion. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100) can be used. An emulsion of squalane, polysorbate 80 and poloxamer 401 ("Pluronic™ L 121") can be used. The emulsion can be formulated in phosphate buffered saline, pH 7.4. This emulsion is a useful delivery vehicle for muramyl dipeptides, and has been used with threonyl-MDP in the "SAF-I" adjuvant, (0.05-1% Thr-MDP, 5% squalane, 2.5% Pluronic L121 and 0.2% polysorbate 80). It can also be used without the Thr-MDP, as in the "AF" adjuvant (Hariharan et al. (1995) Cancer Res 55:3486-9) (5% squalane, 1.25% Pluronic L121 and 0.2% polysorbate 80). Microfluidisation is preferred.

Complete Freund's adjuvant (CFA) and incomplete Freund's adjuvant (IFA) may also be used.

Saponin formulations may also be used as adjuvants in the invention (see for example Chapter 22 of Powell & Newman (eds.) Vaccine Design (1995) Plenum). Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS 17, QS1 8, QS21, QH-A, QH-B and QH-C. Preferably, the saponin is QS21. Saponin formulations may also comprise a sterol, such as cholesterol (WO 96/33739).

As discussed supra, combinations of saponins and cholesterols can be used to form unique particles called immunostimulating complexes (ISCOMs) (see for example Chapter 23 of Powell & Newman (eds.) Vaccine Design (1995) Plenum). ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in WO 96/33739, EP-A-0109942, WO 96/11711). Optionally, the ISCOMS may be devoid of additional detergent WO 00/07621.

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein pi). VLPs are discussed further in WO03/024480 and WO03/024481.

Adjuvants suitable for use in the invention include bacterial or microbial derivatives such as non-toxic derivatives of enterobacterial lipopolysaccharide (LPS), Lipid A derivatives, immunostiinulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref 77. Such "small particles" of 3dMPL are small enough to be sterile filtered through a 0.22 µm membrane (EP-A-0689454). Other non-toxic LPS derivatives include monophosphoryl lipid A mimics, such as aminoalkyl glucosamine de phosphate derivatives e.g. RC-529. Lipid A derivatives include derivatives of lipid A from *E. coli* such as 0M-174. OM-174.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory. The CpG's can include nucleotide modifications/analogs such as phosphorothioate modifications and can be double-stranded or single-stranded. WO02/26757 and WO99/62923 disclose possible analog substitutions e.g. replacement of guanosine with 2'-deoxy-7-deazaguanosine. The adjuvant effect of CpG oligonucleotides is further discussed in WO 98/40100, U.S. Pat. No. 6,207,646, U.S. Pat. No. 6,239,116 and U.S. Pat. No. 6,429,199. The CpG sequence may be directed to TLR9, such as the motif GTCGTT or TTCGTT. The CpG sequence may be specific for inducing a TH1 immune response, such as a CpG-A ODN, or it may be more specific for inducing a B cell response, such a CpG-B ODN. CpG-A and CpG-B ODNs. Preferably, the CpG oligonucleotide is constructed so that the 5' end is accessible for receptor recognition. Optionally, two CpG oligonucleotide sequences may be attached at their 3' ends to form "immunomers" (see, for example, WO03/035836).

Other immunostimulatory oligonucleotides include a double-stranded RNA or an oligonucleotide containing a palindromic sequence, or an oligonucleotide containing a poly(dG) sequence.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192.

Human immunomodulators suitable for use as adjuvants in the invention include cytokines, such as interleukins (e.g. IL-I5 IL-2, IL-4, IL-5, IL-6, IL-7, IL-12, IL-17, IL-18, IL-23, IL-27), interferons (e.g. interferon-γ), macrophage colony stimulating factor, tumor necrosis factor and macrophage inflammatory protein-1 alpha (MIP-1 alpha) and MIP-1 beta.

Bioadhesives and mucoadhesives may also be used as adjuvants in the invention. Suitable bioadhesives include esterified hyaluronic acid microspheres or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO 99/27960).

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

Examples of liposome formulations suitable for use as adjuvants are described in U.S. Pat. No. 6,090,406, U.S. Pat. No. 5,916,588, EP-A-0626169.

Adjuvants suitable for use in the invention include polyoxyethylene ethers and polyoxyethylene esters (WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Phosphazene adjuvants include poly(di(carboxylatophenoxy)phosphazene) ("PCPP").

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

Imidazoquinoline adjuvants include Imiquimod ("R-837") (U.S. Pat. No. 4,680,338 and U.S. Pat. No. 4,988,815), Resiquimod ("R-848") (WO92/15582), and their analogs; and salts thereof (e.g. the hydrochloride salts). Further details about immunostimulatory imidazoquinolines can be found in U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.

Thiosemicarbazone adjuvants include those disclosed in WO 2004/060308. Methods of formulating, manufacturing, and screening for active compounds are also described in WO 2004/060308. The thiosemicarbazones are particularly effective in the stimulation of human peripheral blood mononuclear cells for the production of cytokines, such as TNF-α.

Tryptanthrin adjuvants include those disclosed in WO 2004/064759. Methods of formulating, manufacturing, and screening for active compounds are also described in WO 2004/064759. The thiosemicarbazones are particularly effective in the stimulation of human peripheral blood mononuclear cells for the production of cytokines, such as TNF-α.

Various nucleoside analogs can be used as adjuvants, such as (a) Isatorabine (ANA-245; 7-thia-8-oxoguanosine) and prodrugs thereof; (b) ANA975; (c) ANA-025-1; (d) ANA380; (e) the compounds disclosed in U.S. Pat. No. 6,924,271, US 2005/0070556 and U.S. Pat. No. 5,658,731, or (f) a pharmaceutically acceptable salt of any of (a) to (g), a tautomer of any of (a) to (g), or a pharmaceutically acceptable salt of the tautomer.

Small molecule immunopotentiators useful as adjuvants include N2-methyl-1-(2-methylpropyl)-1H-imidazo(4,5-c)quinoline-2,4-diamine; N2,N2-dimethyl-1-(2-methylpropyl)-1H-imidazo(4,5-c)quinoline-2,4-diamine; N2-ethyl-N2-methyl-1-(2-methylpropyl)-1H-imidazo(4,5-c)quinoline-2,4-diamine; N2-methyl-1-(2-methylpropyl)-N2-propyl-1H-imidazo(4,5-c)quinoline-2,4-diamine; 1-(2-methylpropyl)-N2-propyl-1H-imidazo(4,5-c)quinoline-2,4-diamine; N2-butyl-1-(2-methylpropyl)-1H-imidazo(4,5-c)quinoline-2,4-diamine; N2-butyl-N2-methyl-1-(2-methylpropyl)-1H-imidazo(4,5-c)quinorme-2,4-diamine; N2-methyl-1-(2-methylpropyl)-N2-pentyl-1H-imidazo(4,5-c)quinoline-2,4-diamine; N2-methyl-1-(2-methylpropyl)-N2-prop-2-enyl-1H-imidazo(4,5-c)quinoline-2,4-diamine; 1-(2-methylpropyl)-2-((phenylmethyl)thio)-1H-imidazo(4,5-c)quinolin-4-amine; 1-(2-methylpropyl)-2-(propylthio)-1H-imidazo(4,5-c)quinolin-4-amine; 2-((4-amino-1-(2-methylpropyl)-1H-imidazo(4,5-c)quinolin-2-yl)(methyl)amino)ethanol; 2-((4-amino-1-(2-methylpropyl)-1H-imidazo(455-c)quinolin-2-yl)(methyl)amino)ethyl acetate; 4-amino-1-(2-methylpropyl)-1,3-dihydro-2H-imidazo(4,5-c)quinolin-2-one; N2-butyl-1-(2-methylpropyl)-N4,N4-bis(phenylmethyl)-1H-imidazo(4,5-c)quinoline-2,4-diamine; N2-butyl-N2-methyl-1-(2-methylpropyl)-N4,N4-bis(phenylmethyl)-1H-imidazo(4,5-c)quinoline-2,4-diamine; N2-methyl-1-(2-methylpropyl)-N4,N4-bis(phenylmethyl)-1H-imidazo(4,5-c)quinoline-2,4-diamine; N2,N2-dimethyl-1-(2-methylpropyl)-N4,N4-bis(phenylmethyl)-1H-imidazo(4,5-c)quinoline-2,4-diamine; 1-(4-amino-2-(methyl(propyl)amino)-1H-imidazo(4,5-c)quinolin-1-yl}-2-methylpropan-2-ol; 1-(4-amino-2-(propylamino)-1H-imidazo(4,5-c)quinolin-1-yl)-2-methylpropan-2-ol; N43N4-dibenzyl-1-(2-methoxy-2-methylpropyl)-N2propyl-1H-imidazo(4,5-c)quinoline-2,4-diamine.

One potentially useful adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of *Neisseria meningitidis* outer membrane and lipopolysaccharides. They have been used as adjuvants for influenza vaccines (WO 02/072012).

Other substances that act as immunostimulating agents are disclosed in Vaccine Design ((1995) eds. Powell & Newman. ISBN: 030644867X. Plenum) and Vaccine Adjuvants: Preparation Methods and Research Protocols (Volume 42 of Methods in Molecular Medicine series) (ISBN: 1-59259-083-7. Ed. O'Hagan). Further useful adjuvant substances include: Methyl inosine 5'-monophosphate ("MIMP"); a polyhydroxlated pyrrolizidine compound (WO 2004/064715), examples include, but are not limited to: casuarine, casuarine-6-α-D-glucopyranose, 3-epz-casuarine, 7-epz-casuarine, 3,7-diepz-casuarine, etc; a gamma inulin or derivative thereof, such as algammulin; compounds disclosed in PCT/US2005/022769; compounds disclosed in WO 2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,606,617, WO 02/018383), Hydrapthalamide compounds, Benzophenone compounds, Isoxazole compounds, Sterol compounds, Quinazilinone compounds, Pyrrole compounds (WO 04/018455), Anthraquinone compounds, Quinoxaline compounds, Triazine compounds, Pyrazalopyrimidine compounds, and Benzazole compounds (WO 03/082272); loxoribine (7-allyl-8-oxoguanosine) (U.S. Pat. No. 5,011,828); a formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE:DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409).

The invention may also comprise combinations of aspects of one or more of the adjuvants identified above. For example, the following adjuvant compositions may be used in the invention: (1) a saponin and an oil-in-water emulsion (WO 99/11241); (2) a saponin (e.g. QS21)+a nontoxic LPS derivative (e.g. 3dMPL) (WO 94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO 98/57659); (5) combinations of 3dMPL with, for example, QS21 and/or oil-in-water emulsions (EP 0835318, EP 0735898, EP 0761231); (6) Ribi™ adjuvant system (RAS), (Ribi Imrnunochern) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™);

and (7) one or more mineral salts (such as an aluminum salt)+a non-toxic derivative of LPS (such as 3dMPL).

Generally, an adjuvant is administered at the same time as the antigen. However, adjuvants can also, or alternatively be administered within a two-week period prior to the vaccination, and/or for a period of time after vaccination, i.e., so long as the antigen persists in the tissues.

Vaccine may be administered in various ways known to the skilled person, for example in particulate form, such as on a microcarrier or a nanocarrier (Paolicelli et al., 2010). One particular system uses PRINTED technology by delivering the vaccine antigen on a dissolvable particle (Liquidia Technologies, NC, USA).

The immunogenic compositions and vaccines according to the invention may be further supplemented by the addition of other recombinant or purified antigens which may result in the production of antibodies of a variety of specificities when administered to a subject. Not all of these antibodies need to be protective against a disease. In a particular embodiment of this type, such antigens are also from *Plasmodium*, for example, from *Plasmodium falciparum*. Thus, a vaccine of the present invention may contain various other active or inactivated pathogenic factors, along with at least one polypeptide defined herein. Therefore, in accordance with the present invention, at least one polypeptide defined herein can be combined with other *Plasmodium* and non-*Plasmodium* antigens.

In one embodiment, the composition of the invention comprises an Rh polypeptide or antigenic fragment thereof. As would be known to the person skilled in the art, Rh polypeptides belong to the family of reticulocyte binding-like proteins in *Plasmodium* spp. that are important for invasion of erythrocytes by merozoites. In *Plasmodium falciparum*, the Rh polypeptide family includes pfRh1 (e.g., PlasmoDB accession PFD0110w (www.plasmodb.org); Genbank accession AF533700; AF411933; AF411930), pfRh2a (e.g., PlasmoDB accession PF13_0198; Genbank accession AY138497; AY138498; AY138499), pfRh2b (e.g., PlasmoDB accession MAL13P1.176; Genbank accession AY138500; AY138501; AY138502; AY138503), pfRh4 (e.g., PlasmoDB PFD1150c; Genbank accession AF432854; AF420309), and pfRh5 (e.g., PlasmoDB PFD1145c; Genbank accession XP_001351544). Further details of Rh polypeptides and antigenic fragments thereof are provided above.

In another embodiment, the composition of the invention comprises an EBA polypeptide or antigenic fragment thereof. As would be understood in the art, EBA polypeptides belong to the *Plasmodium* erythrocyte binding-like (ebl) protein family which have also been shown to be important in merozoite invasion of erythrocytes. In *Plasmodium falciparum*, the EBA polypeptide family includes EBA-175 (e.g., PlasmoDB accession MAL7P1.176; Genbank accession XP_001349207), EBA-181 (e.g., PlasmoDB accession PFA0125c; Genbank accession ACN62280), EBA-165 (e.g., PlasmoDB accession PFD1155w; Genbank accession XP_001351546), and EBA-140 (e.g., PlasmoDB accession MAL13P1.60; Genbank accession XP_001349859). Further details of EBA polypeptides and antigenic fragments thereof are provided above.

A composition of the invention typically comprises a pharmaceutically acceptable carrier. Such carriers include any excipient that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

The pH of the composition is preferably between 6 and 8, preferably about 7. The pH may be maintained by the use of a buffer. A phosphate buffer is typical. The composition may be sterile and/or pyrogen-free. The composition may be isotonic with respect to humans. Compositions may include sodium salts (e.g. sodium chloride) to give tonicity. A concentration of 10+/−2 mg/ml NaCl is typical. Compositions may also comprise a detergent e.g. a Tween (polysorbate), such as Tween 80. Detergents are generally present at low levels e.g. <0.01%.

Compositions may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

The composition may further comprise an antimalarial that is useful for the treatment of Plasmodial infection. Preferred antimalarials for use in the compositions include the chloroquine phosphate, proguanil, primaquine, doxycycline, mefloquine, clindamycin, halofantrine, quinine sulphate, quinine dihydrochloride, gluconate, primaquine phosphate and sulfadoxine.

The compositions of the invention may also comprise one or more immunoregulatory agents. Preferably, one or more of the immunoregulatory agents include(s) an adjuvant. The adjuvant may be selected from one or more of the group consisting of a TH1 adjuvant and TH2 adjuvant, further discussed below.

The immunogenic compositions and vaccines of the present invention may be administered in any suitable form such as a liquid, emulsion, dried powder and/or in a mist through any parenteral route, intravenously, intraperitoneally, intradermally, by scarification, subcutaneously, intramuscularly, or inoculated by a mucosal route, e.g., orally.

The immunogenic compositions and vaccines of the present invention may be administered using a variety of vaccination regimes familiar to the skilled person. In one form of the invention, the vaccine composition may be administered post antimalarial treatment. For example, blood stage parasitaemia may be cleared with Fansidar (25 mg sulfadoxine/0.75 mg pyrimethamine per kg body weight) before each vaccination. In another form of the invention antimalarial (e.g. Fansidar) treatment is given 1 to 2 weeks before the doses (e.g. first and third doses). In another form of the invention antimalarial (e.g. Fansidar) treatment is given before the first dose.

In another form of the invention, 3 doses of vaccine composition (e.g. 0.5 mg adsorbed onto 0.312 g alum in 0.125 mL) is administered in 3 doses, 2 mg per dose to >5 year olds, 1 mg to under 5 year olds, at weeks 0, 4, and 25. In another form of the invention, 3 doses of vaccine composition (e.g. 1 mg per dose) are given subcutaneously at weeks 0, 4, and 26. In another form of the invention, 3 doses of vaccine composition is administered on days 0, 30, and 180 at different doses (e.g. 1 mg; 0.5 mg). In another form of the invention, 3 doses of vaccine composition is administered at 3 to 4 month intervals either intramuscularly or subcutaneously. In another form of the invention 3 doses of vaccine composition is administered subcutaneously on days 0, 30, and about day 180. In another form of the invention, the vaccine composition is administered in 2 doses at 4-week intervals (e.g. 0.55 mL per dose containing 4 μg or 15 μg or 13.3 μg of each antigen). In another form of the invention, 3 doses of the vaccine composition is administered (e.g. 25 μg in 250 μL AS02A adjuvant) intramuscularly in deltoid (in alternating arms) at 0, 1, and 2 months. In another form of the invention 4 doses of the vaccine composition is given (e.g. 50 μg per 0.5 mL dose) on days 0, 28, and 150; and dose 4 given in the following year. In another form of the invention, where the vaccine is a DNA vaccine, the vaccine composition is administered in two doses (e.g. 2 mg on days 0 and 21 (2 intramuscular injections each time, 1 into each deltoid muscle). In another form of the invention, where the vaccine composition comprises an immunogenic molecule covalently linked to another molecule (e.g. *Pseudomonas aeruginosa* toxin A) the composition is administered in 3 doses (e.g. at 1, 8, and 24 weeks).

Screening Assays

The polypeptides of the invention may be employed in a screening process for compounds which activate (agonists) or inhibit (antagonists) the ability of the polypeptide to bind an erythrocyte receptor (receptor binding).

Examples of potential antagonists include antibodies, oligosaccharides and derivatives thereof. A potential antagonist includes a small molecule which binds to the polypeptide of the invention, making it inaccessible to a binding partner of the polypeptide. Examples of small molecules include, but are not limited to, small organic compounds, small peptides or peptide-like molecules. The small molecules may mimic the structure of a binding partner of the polypeptide according to the invention.

The invention also comprehends high-throughput screening (HTS) assays to identify compounds that interact with or inhibit the biological activity (i.e., affect receptor binding activity) of a polypeptide of the invention. HTS assays permit screening of large numbers of compounds in an efficient manner. HTS assays are designed to identify "hits" or "lead compounds" having the desired property, from which modifications can be designed to improve the desired property. Chemical modification of the "hit" or "lead compound" is often based on an identifiable structure/activity relationship between the "hit" and the polypeptide.

EXAMPLES

Example 1. Identification of pfRip as Rh5 Complex Partner

Processed 45 kDa pfRh5 from parasite culture supernatant was purified by ion-exchange chromatography. Analysis of pfRH5 by size exclusion chromatography on a Superdex 200 analytical column demonstrated that pfRh5 was eluted as an ~150-200 kDa species (FIG. 1A). Blue native gel electrophoresis confirmed that pfRh5 migrates on a gel as an ~150-200 kDa species (FIG. 1B).

To determine whether pfRh5 is in complex with other molecules or if it forms a homo-oligomer, the protein was incubated with pfRh5 antibody and analysed by size exclusion chromatography. A 300 μl pfRh5-containing fraction isolated from culture supernatant was loaded onto a Superdex 200 analytical column and eluted with PBS (FIG. 2A). An identical 300 μl sample was pre-incubated with 25 μg monoclonal pfRh5 antibody at room temperature for 15 minutes and then on ice for 2 hours before loading onto being loaded onto a Superdex 200 analytical column and eluted with PBS. The pfRh5 eluted as an ~300 kDa species (FIG. 2B) indicating one antibody molecule bound to the 150-200 kDa pfRh5-containing species. This suggested that the 45 kDa pfRh5 fragment is in complex with other molecules rather than forming a homo-oligomer.

PfRh5 complex purified from culture supernatant of RhSHA parasite line by anti-HA affinity resin was subjected to trypsin digestion in solution and the resulting peptides analysed by mass spectrometry (LC-MS/MS) and identified by searching databases (Table 2). The results show that PfRh5 binds pfRip (SEQ ID NO:2).

TABLE 2

Mass spectrometry identified PfRip as pfRh5 complex partner.

| Protein name | Peptide position | Peptide sequence |
| --- | --- | --- |
| pfRh5 | 187-197 | (K)HLSYNSIYHK(S) (SEQ ID NO: 29) |
|  | 212-221 | (K)KINETYDKVK(S) (SEQ ID NO: 30) |
|  | 237-247 | (K)KLEHPYDINNK(N) (SEQ ID NO: 31) |
|  | 303-310 | (K)MMDEYNTK(K) (SEQ ID NO: 32) |
|  | 358-366 | (R)YHYDEYIHK(L) (SEQ ID NO: 33) |
|  | 437-443 | (K)IIQDKIK(L) (SEQ ID NO: 34) |
| PfRip | 93-100 | (K)ScDYFISK(E) (SEQ ID NO: 5) |
|  | 101-114 | (K)EYNSSDKTNQIcYK(K) (SEQ ID NO: 6) |
|  | 699-708 | (K)LIcQcEEGYK(N) (SEQ ID NO: 7) |
|  | 760-769 | (K)MEDGINcIAK(N) (SEQ ID NO: 8) |
|  | 963-972 | (K)INcTcKENYK(N) (SEQ ID NO: 9) |

Example 2. Shedding of pfRip into Culture Supernatant

A single Strep-tag and triple Haemaglutinin (HA) tag were added to the C-terminus of pfRip by 3'-single homologous cross-over recombination (FIG. 3A) Immunoblotting of saponin pellet and HA-tagged protein purified from culture supernatant of pfRipHA line with anti-HA antibody demonstrated that PfRip was processed and shed to culture supernatant (FIG. 3B). PfRipHA was also analysed by SDS-PAGE under reducing and non-reducing conditions and transferred to nitrocellulose membrane Immunoblotting with anti-HA antibody showed that the processed C-terminal fragment migrates similarly under both reducing and non-reducing condition, suggesting that N-terminal and C-terminal of pfRip is not linked by any disulphide bond after processing (FIG. 3C).

Example 3. Immunoprecipitation of pfRip

Culture supernatants from both wt 3D7 and 3D7-pfRipHA parasite lines were immunoprecipitated with anti-HA-Sepharose bead. Bound materials were separated by SDS-PAGE, transferred to nitrocellulose membrane to probe for pfRh5 using monoclonal anti-pfRh5 antibody (clone 2F1). Detection of pfRh5 in the bound material only from 3D7-pfRipHA line indicated that pfRh5 was specifically co-immunoprecipitated with pfRipHA (FIG. 4A).

Culture supernatants from both wt 3D7 and 3D7-pfRipHA parasite lines were immunoprecipitated with monoclonal anti-pfRh5 antibody coupled to Mini-bead, and culture supernatant of 3D7-pfRipHA parasites was incubated with just Mini-bead as additional control. Bound materials were separated by SDS-PAGE, transferred to nitrocellulose membrane to probe for pfRipHA using anti-HA antibody (FIG. 4B). Detection of pfRipHA in the bound material only from 3D7-pfRipHA parasite line immunoprecipitated with anti-pfRh5-Mini-bead indicated that pfRip was specifically co-immunoprecipitated with pfRh5.

Example 4. Expression of pfRh5 and pfRip in Life-Cycle of *P. falciparum*

Figure 5:
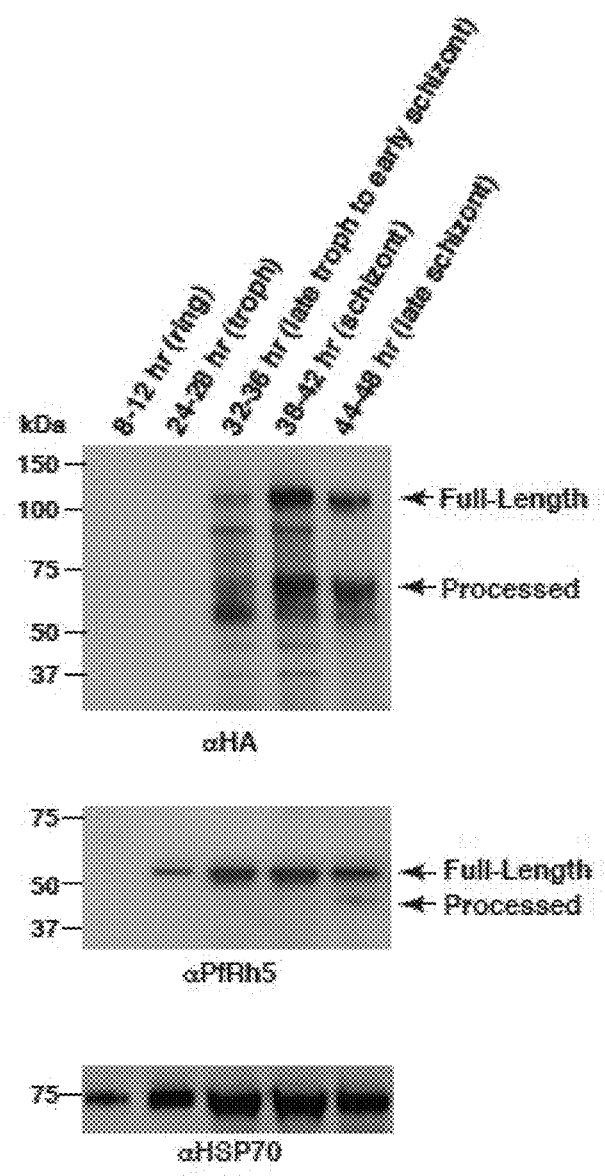
FIG. 5. Both pfRh5 and pfRip express at late life cycle of parasite development. Immunoblot of saponin pellets obtained from triple synchronized pfRipHA parasite culture probed with monoclonal anti-HA antibody, and then stripped and probed with antibodies to pfRh5 and pfhsp70.

A 30 ml-dish of triple synchronized pfRipHA parasite culture (the third synchronization was done when the parasites were in the 8-12 hours ring stage) was distributed into six 5-ml dishes. One dish of culture was harvested for preparing saponin pellet immediately after the third synchronization. The second dish was harvested 16 hr later, the third dish another 8 hr later and subsequent dishes every 6 hr later until the end of schizogony. The saponin pellets prepared from the harvested parasites were separated by SDS-PAGE and transferred to nitrocellulose membrane. The membrane was firstly probed with monoclonal anti-HA antibody for pfRipHA and then stripped to probe for pfRh5 and pfhsp70. Both pfRh5 and pfRip were shown to be expressed at late life cycle stage of parasite development (FIG. 5).

Example 5. Generation of Recombinant pfRip-791-900 and pfRip-238-368

To generate recombinant fragment of pfRip-791-900 (amino acid 791 to 900), oligonucleotides (SEQ ID NO: 40)
5' CGCTAGCCATATGAATGAAGAAACAGATATTGTAAAATG 3'
and (SEQ ID NO: 41)
5' CGAGGATCCCTAATCTTCTAAAACACATTTTCC 3' were used to PCR amplify the fragment from genomic DNA prepared from 3D7 parasite. The resulting PCR fragment was then cloned into pET14b vector with NdeI and BamHI site, transformed into BL21 RIL *E. coli* strain for expressing recombinant pfRip-791-900 as a hexa-His-tagged protein. The His-tagged protein was purified from soluble lysate of bacteria cells by Ni-resin affinity purification followed by gel-filtration chromatography on Superdex 75 column.

The construct for producing the recombinant fragment of pfRip-238-368 (amino acid 238 to 368) was made by synthesizing codon-optimized DNA sequence coding for pfRip amino acid sequence 238 to 368 and cloned into pET28a vector with NheI and BamHI sites. The construct was then transformed into BL21 RIL *E. coli* strain and produced hexa-His-tagged protein as inclusion body. The protein solubilised from the inclusion body was refolded, purified by Ni-resin affinity column.

Example 6. Production of Antibodies and Western Blot Analysis

The diagram in FIG. 6A shows the region of pfRip that was produced as recombinant protein. Coomassie blue stain of Ni-resin and gel-filtration column purified recombinant protein in shown in FIG. 6B Immunoblot analysis of native pfRip probed with antibodies raised against recombinant protein is shown in FIG. 6C.

PfRipHA parasite (late schitzont stage)-infected red blood cells were hypotonically lysed with water, centrifuged and pellet fraction washed with PBS twice. The pellet fraction was then divided into four eppendorfs and incubated on ice for 2 hours with 10 mM Tris/pH 8.0; 100 mM sodium carbonate/pH 11.5; 2% Triton X100 and 2% CHAPS in 50 mM Tris/pH8.0, 1 mM EDTA and 100 mM sodium chloride respectively. The samples were centrifuged to separate soluble and insoluble fractions. The insoluble fraction was washed twice with PBS and analysed by western blot together with the soluble fraction (FIG. 7A). Saponin pellet prepared from the pfRipHA parasite (late schitzont stage)-infected red blood cells were subjected to the same analyses described above (FIG. 7B). The results demonstrate that PfRip is a peripheral membrane protein and carries its complex partner pfRh5 onto the surface of merozoites.

Example 7. Inhibition of Parasite Attachment and Growth

Pre-incubation of purified merozoites with Protein-A purified rabbit polyclonal antibodies [R1155 (αpfRIP/1) and R1156 (αpfRIP/2) at 2 mg/ml] raised against recombinant pfRip for 2 minutes at 37° C. inhibited merozoites attachment to uninfected red blood cells by 40-55% (FIG. 8A). Protein-A purified antibodies from normal serum were used as control (NRS). Growth inhibition assay (GIA) for *P. falciparum* strains 3D7, D10, FCR3 and W2mef are shown in FIG. 8B. Shown in FIG. 8C is the Titration of IgG anti-PfRIP-1 antibodies with FCR3. The titration of IgG anti-PfRIP-1 antibodies with 3D7 is shown in FIG. 8D.

The present inventors tested the anti-PfRIP/1 and anti-PfRIP/2 antibodies (αPfRIP/1 and 2 antibodies) for their ability to block parasite growth (growth inhibition assays, GIA) using the *P. falciparum* strains FCR3, W2mef, T994, CSL2, E8B, MCAMP, 7G8, D10, HB3, and 3D7 (FIG. 9A). Significantly, the FCR3 strain was inhibited to 80% whilst in comparison 3D7 was inhibited to 35% with αPfRIP/1 at 2 mg/ml (FIG. 9A). The inhibition observed for 3D7 was comparable to that observed for other antibodies raised to regions of the PfRh or EBL protein families. Similar results were observed for 3D7 using the αPfRIP/2 (data not shown). The level of growth inhibition activity observed with the αPfRIP/1 and αPfRIP/2 antibodies for 3D7 parasites was similar to that observed in the attachment assays demonstrating that the inhibitory effect was occurring at merozoite invasion rather than during the growth of the parasite (FIG. 8A).

Among other *P. falciparum* strains tested αPfRIP/1 antibody exhibited significantly higher inhibitory activity for those that invade erythrocyte preferentially using sialic acid-dependent receptors (ie. glycophorins), which includes FCR3, W2mef, T994, CSL2 and E8B. The αPfRIP/1 antibody was titrated in GIAs in comparison with IgG from normal serum for both FCR3 and 3D7 parasite strains. Growth of FCR3, a parasite that invades preferentially by sialic acid-dependent pathways, was almost completely abolished at 3 mg/ml and significant inhibition still remained even at 1 mg/ml (40%). In comparison, the 3D7 parasite strain, which can efficiently use sialic acid-independent invasion pathways primarily by using the ligand PfRh4 and complement receptor 1, was inhibited at significantly lower levels with 40% at 3 mg/ml and this decreased to 25% at 1 mg/ml of antibody. This suggests that the PfRIP/PfRh5 complex may be more functionally important in *P. falciparum* strains that efficiently use sialic acid-dependent invasion pathways.

The region of PfRIP to which the anti-PfRIP antibodies were raised was from the 3D7 strain of *P. falciparum*;

however, this domain does not show any polymorphisms in other strains that have been sequenced (http://plasmodb.org/). Also, the present inventors did not observe any cross-reactivity of the antibodies with other proteins that contain EGF-like domains such as MSP1. This was not surprising as the only conserved amino acids was the six cysteine residues that define each EGF-like domain (FIG. 6). Therefore the differences in inhibition observed in GIA with the various strains was unlikely due to cross reactivity with other proteins containing EGF-like domains or polymorphisms within this region of PfRIP. It is more likely reflects the reliance of them on the PfRh5/PfRIP complex to mediate a specific invasion pathway in comparison to the function of other members of the PfRh and EBA protein families. To test this we used a combination of IgG antibodies raised to PfRIP, EBA-175, PfRh4, PfRh2a and PfRh2b to determine if they increased the level of inhibition in GIAs for 3D7 parasites (FIG. 9B). Both αPfRIP/1 and αPfRIP/2 antibodies inhibited 3D7 parasites to 25 and 20% respectively (FIG. 9B), similar to our previous experiment (FIG. 8B). The combination of αPfRIP/1 with αEBA-175 antibodies showed an additive inhibition of 45% (FIG. 9B). This was a similar result to that observed for the combination of αPfRIP/1 with αPfRh4 or αPfRh2a/b antibodies. Significantly, a combination of αPfRIP/1, αPfRh2a/b and αPfRh4 showed a much higher level of inhibition (74%). This additive effect was consistent with parasites using multiple invasion pathways to gain entry to the erythrocyte.

Example 8. Identification of the pfRh2a/b Erythrocyte Binding Site

To confirm the 85 kDa PfRh2a and b protein was directly responsible for binding to human erythrocytes recombinant proteins were made of different portions that covered this region. A protein of 15 kDa corresponding to amino acids 446 to 557 of the PfRh2a/b N-terminus (rRh2$_{15}$), expressed as an *E. coli* hexa-His tagged protein, bound to erythrocytes whereas the 2b1 protein from the C-terminal region of PfRh2b showed no detectable binding (FIG. 10). The rRh2$_{15}$ erythrocyte binding was resistant to trypsin treatment but partially sensitive to chymotrypsin and neuraminidase treatment, a pattern of binding observed for the *P. falciparum* expressed 85 kDa protein from culture supernatants.

To show that binding of rRh2$_{15}$ to erythrocytes was specific it was determined if IgG antibodies raised to this domain block binding of both the 85 kDa fragment from parasite supernatants and the rRh2$_{15}$ fragment. The antibodies R1170 showed a dose-dependent inhibition of binding of the 85 kDa fragment in contrast to antibodies raised to a second recombinant protein of PfRH2a/b made from the N-terminus and IgG from normal rabbit serum (FIG. 11A). The same R1170 antibodies also blocked binding of the rRh2$_{15}$ recombinant protein in a dose-dependent manner (FIG. 11B). Therefore the erythrocyte-binding domain of PfRh2a and b is located within the region defined by the 15 kDa rRh2$_{15}$ recombinant protein.

Example 9. Antibodies to the PfRh2a/b Binding Site Inhibit Merozoite Invasion

To determine if antibodies to rRh2$_{15}$ (R1170) inhibit invasion they were tested in growth inhibition assays with normal and trypsin-treated erythrocytes. The anti-rRh2$_{15}$ antibodies showed approximately 18% inhibition into normal erythrocytes compared to no inhibition for antibodies to a second fusion protein close to the receptor binding site and this was increased for trypsin-treated cells to 38% (FIG. 11C). The enhancement of inhibition occurred as a result of removal of trypsin-sensitive receptors from erythrocytes thus limiting those available. The PfRh2a/b erythrocyte receptor is trypsin-resistant and removal of other receptors by this treatment increases the potency of these inhibitory antibodies (Duraisingh et al., 2003).

To show that the inhibitory effect was specific and also to determine if it was acting on the function of both PfRh2a and PfRh2b the *P. falciparum* lines in which each gene had been specifically disrupted were used (Duraisingh et al., 2003). For normal erythrocytes anti-rRh2$_{15}$ antibodies inhibited growth at approximately the same level for 3D7Δ2a, which lacks expression of PfRh2a, and the 3D7 parent and this was enhanced for trypsin-treated erythrocytes. In contrast, the *P. falciparum* lines 3D7Δ2b (lacks expression of PfRh2b) and FCR3 (lacks expression of PfRh2a and PfRh2b) were not inhibited (FIG. 11D). Therefore the anti-rRh2$_{15}$ antibodies to the receptor-binding site directly inhibit PfRh2b function but not PfRh2a as it was not functional in 3D7.

Example 10. Inhibition of *P. falciparum* Invasion of Human Red Blood Cells

Antibodies against a combination of antigens were tested for their ability to inhibit invasion of *P. falciparum* into human red blood cells in vitro.

Rabbits were immunized with a total of 225 μg protein comprising 75 μg of each the following antigens: EBA175 R3-5 (amino acids 760-1271; SEQ ID NO:36), PfRh2a/b (15 kDa fragment; SEQ ID NO:12) and PfRIPr (791-900; SEQ ID NO:3).

Blood was taken and IgG fraction purified 34 days following a single immunization with the three antigens. Serial dilutions were made of the IgG with 2 mg/ml starting concentration. Antibodies were incubated together with *P. falciparum* parasites 3D7. Control Ab was non-immune rabbit IgG. Percentage invasion is calculated as 100×(mean invasion (triplicate wells) of control IgG/test IgG).

FIG. 12 shows titration of the growth inhibitory response against wild type 3D7 parasites, with a reduction of invasion of 62% at 2 mg/ml compared to non-immune serum.

Example 11. Synthetic PfRip Fragment Encompassing Amino Acids 604-1086

DNA encoding the PfRip fragment amino acids 604-1086 was synthesized by Life Technologies (Mulgrave, Victoria, Australia). Codon usage was adapted to the bias of *E. coli* resulting in a CAI (codon adaptation index) value of 0.96. See FIG. 13.

Expression of PfRip Fragment Encompassing Amino Acids 604-1086 of SEQ ID NO:2

For expression in Hi5 insect cells, the synthetic sequence was cloned into pTriEx-2 (Novagen) using the Kpn 1/Xho 1 restriction site.

The PfRip 604-1086 fragment (SEQ ID NO: 60) was expressed with N-terminal 6-HIS+FLAG tags in Hi5 insect cells in the vector pTriEx-2 (Novagen) modified to include a signal peptide before the His-tag as well as a flag-tag (italics). A TEV cleavage site was also included (underlined).

```
                              (tag sequence; SEQ ID NO: 61)
         MAHHHHHHSSGDYKDDDDKGGEQLYFQGTHM
```

The predicted size of the fragment is 59456.9 Da.
Protein Purification Protocol
1. Soluble HIS-FLAG-PfRip (amino acids 604-1086) was purified over anti-FLAG beads according to the following protocol:
2. Insect cell culture supernatant was harvested and spun at 10,000 rpm, 4° C. for 60 minutes and clear supernatant was collected for purification, which can be done using a batch method or a column.
3. PfRip baculovirus expression culture supernatant was incubated with anti-FLAG M2 beads (Sigma)
4. The capacity of the M2 bead is ~500 μg per ml of resin with a yield of approximately 3-5 μg from 1 L culture. M2 beads were regenerated using 0.1M Glycine pH 3.0.
5. M2-bound PfRip protein was eluted off the beads using FLAG peptide (0.1 mg/ml) in Tris pH 8.0 buffer with 100 Mm NaCl. Gel-filtration column or dialysis is used to remove the flag peptide.
6. The purified protein PfRip was then aliquoted into eppendofs, snap-frozen and stored at −80° C.

Expression of PfRip Fragment Encompassing Amino Acids 604-1086 in *E. coli*

PfRip (amino acids 604-1086) can be expressed in *E. coli*, for example in the vector pET-45 with a N-terminal HIS tag (underlined).
MAHHHHHHVGTGSNDDDDKSPDP (N-term tag in *E. coli*; SEQ ID NO: 62) PfRip (amino acids 604-1086) can also be expressed in *E. coli*, for example in the vector pET-303 with a C-terminal HIS tag protein. The fragment can also comprise an N-terminal Methionine residue. LEHHHHHH (C-term tag sequence; SEQ ID NO: 63)

The predicted sizes these latter PfRip fragments are 58 KD and 57 KD, respectively.

Example 12. Expression of EBA175 Fragment Encompassing Amino Acids 761-1298 of SEQ ID NO: 35

EBA175 amino acids 761-1298 from Pf strain 3D7 were cloned into the pET-45b (+) vector using Bam HI and Xho I restriction sites to produce a recombinant protein with an N-terminal hexa-His tag. The plasmid was transformed into BL21 *E. coli* and His-tagged recombinant protein was purified from soluble lysate.

Amino acid 1058 (Glu; E) shown as bold and underlined can alternatively be a Val (V) in some strains. Amino acid 1100 (Gly) shown as bold and underlined can alternatively be a Asp (D) in some strains. See FIG. 14.

EBA175 fragment amino acids 761-1298 of SEQ ID NO: 35 (the fragment is designated herein SEQ ID NO: 64) may comprise an N-terminal hexa-His tag.

Example 13. Antibodies Immunospecific for Merozoite Antigens Inhibit Parasite Invasion and Growth Testing for Optimal Antigenic Peptides; Antibody Production Method:

In order to select an optimal antigenic Pf Rip fragment for a vaccine composition, a new batch of antibodies was produced in rabbits. Thus, protein fragments corresponding to RIP/1 (amino acids 791-900 of PfRip), RIP/2 (amino acids 238-368 of PfRip) and amino acids 604-1086 of PfRipwere used to immunize rabbits to raise antisera for testing.

Because the vaccine is to be used in humans, a regimen optimized to be compatible with a human vaccination schedule was adopted. The vaccine schedule called for three immunizations: on day 1, day 28, and day 52, each followed by a final bleed for sera 14 days after the third immunization.

Growth Inhibition Assay (GIA) Method:

The growth inhibition single cycle assay was performed according to methods described in Malkin E M. et al. (2005, Infect Immun 73: 3677-3685), the entire content of which is incorporated herein by reference.

Figure 16:
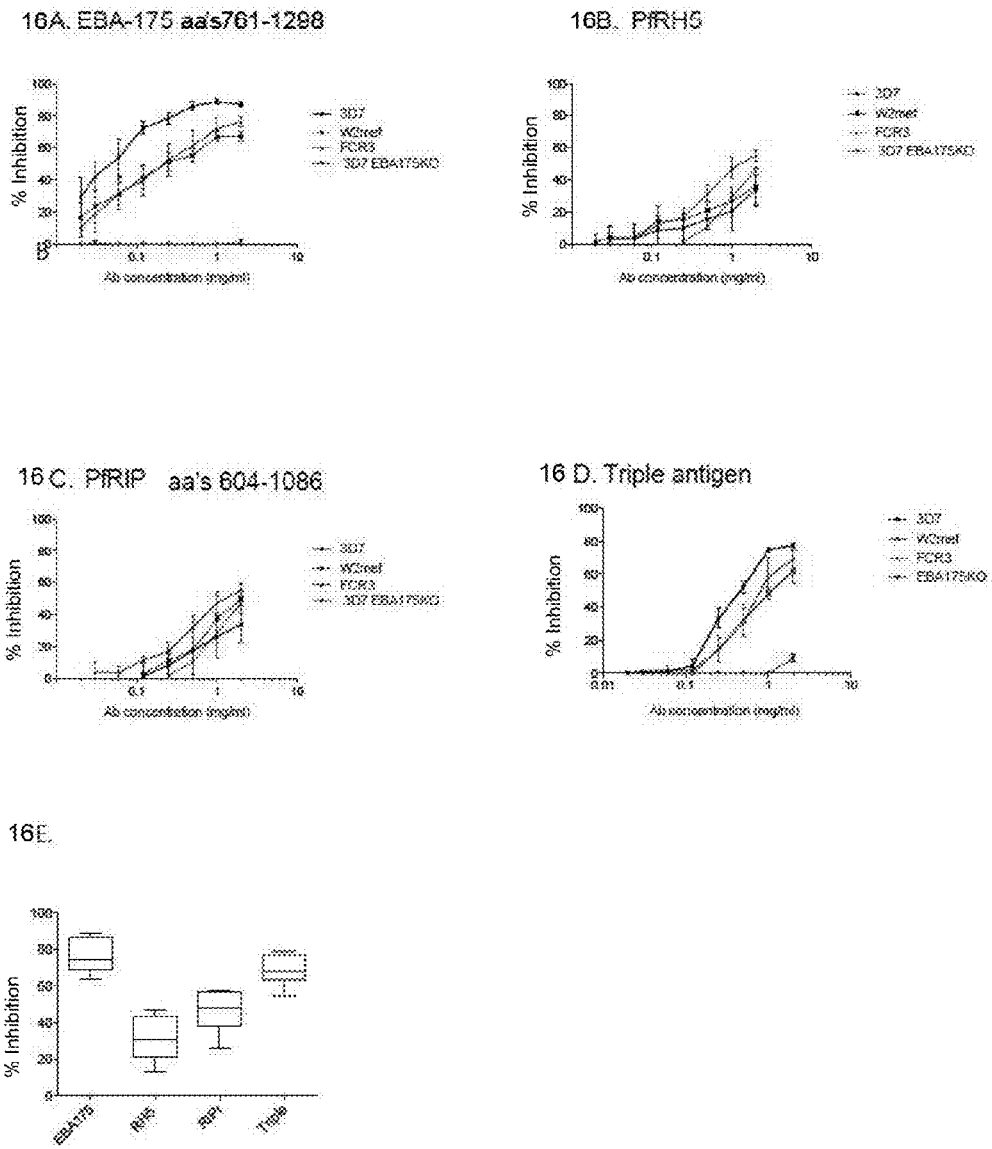

Results from the growth inhibition assay using anti-RIP/2 antiserum indicate that the antibodies raised using the "human compatible" immunization regimen were not effective in inhibiting parasite growth at any of the antibody concentrations tested (FIG. 15). Similar results were seen using anti-RIP/1 antiserum (results not shown). In contrast and unexpectedly, the antibody raised against the 604-1086 PfRip antigenic fragment using the same immunization regimen exhibited a dose dependent response and good inhibition of the strains tested (FIG. 16C). This fragment was therefore selected as an improved component of a triple vaccine composition (see FIG. 16D results).

Antibodies raised against merozoite antigens inhibit invasion of different parasite strains in a single cycle GIA assay. IgG raised against EBA-175 amino acids 761-1298 (3D7 strain) (FIG. 16A), PfRH5 (FIG. 16B), PfRIP 604-1086 fragment (FIG. 16C) and a triple antigen cocktail (FIG. 16D) are inhibitory against 3D7, W2mef and FCR3 parasites (FIG. 16E). Median growth inhibition (line), 95% confidence intervals (CI) (box) and minimum and maximum GIA (error bars) for IgG against EBA-175, PfRH5 and PfRIP at 2 mg/ml against 3D7, W2mef and FCR3 parasites are shown. Antibodies against EBA-175 amino acids 761-1298, PfRH5 and PfRIP recombinant antigens are inhibitory to growth of genetically diverse parasites in vitro.

IgG against EBA175 amino acids 761-1298 shows a dose-dependent inhibition of parasite growth relative to parasites in non-immune IgG of up to 89% at the top IgG concentration of 2 mg/ml against 3D7 parasites, 76% inhibition of FCR3 and 67% inhibition of W2mef, while 3D7 parasites with a genetic deletion in eba-175 were not inhibited at all (FIG. 16A). IgG raised against recombinant PfRH5 were somewhat less inhibitory than those against EBA-175, but again, a dose-dependent effect of up to 55% at 2 mg/ml IgG was observed for FCR3 parasites, while other strains were less well inhibited at this IgG concentration. Interestingly, the 3D7 line lacking EBA-175 was more susceptible to anti-PfRH5 antibodies than 3D7 wild type parasites in these assays (FIG. 16B). IgG against PfRIP also showed a similar inhibition profile to those against PfRH5, with FCR3 and W2mef parasites more susceptible than 3D7 in this case (FIG. 16C). A comparison of the cross-strain inhibitory responses for IgG targeting each single antigen (FIG. 16E) clearly shows the variability in potential for antibodies targeting single antigens to inhibit growth of different parasite strains. IgG from rabbits immunized with the three antigens in combination (Triple antigen; FIG. 16D) exhibit synergism and were more inhibitory than those against either PfRH5 or PfRIP (labelled RIPr in FIG. 16E) alone and comparable to IgG against EBA-175.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from U.S. Ser. No. 61/411,598 and U.S. 61/435,602, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Breman et al. (2004) Am J Trop Med Hyg, 71 Suppl 2:1-15.
Duraisingh et al. (2003) EMBO J, 22:1047-1057.
George, et al. (2003) Protein Engineering, 15:871-879.
Harayama (1998) Trends Biotech, 16; 76-82.
Hay et al. (2004) Lancet Infect Dis, 4:327-336.
Hoffmann et al. (2002) J Infect Dis, 185:1155-1164.
Needleman and Wunsch (1970) J Mol Biol, 48:443-453.
Ohta et al. (1998) Tokai J Exp Clin Med, 23:85.
Paolicelli et al. (2010) Nanomedicine, 5:843-853.
Rammensee (1995) Curr Opin Immunol, 7:85-96.
Singh et al. (2010) PLos One, 5:e9435.
Snow et al. (2004) Am J Trop Med Hyg, 71 Suppl 2:16-24.
Sun et al. (2009) Vaccine 27:1787-1796.
Wang et al. (2001) Proc Natl Acad Sci USA, 98:10817-10822.

The invention claimed is:

1. A recombinant combination vaccine composition comprising an isolated and/or recombinant first and a second polypeptide, wherein the first polypeptide consists of SEQ ID NO: 60 or consists of SEQ ID NO: 60 having one or more point mutations selected from the group consisting of:
   L at amino acid position 70 replaced with V,
   A at amino acid position 152 replaced with G,
   Y at amino acid position 382 replaced with N, and
   I at amino acid position 436 replaced with M;

and wherein said second polypeptide consists of SEQ ID NO: 64 or consists of SEQ ID NO: 64 having one or more point mutations selected from the group consisting of:
   S at amino acid position 8 replaced with N,
   E at amino acid position 163 replaced with K,
   K at amino acid position 172 replaced with E,
   E at amino acid position 298 replaced with V, and
   G at amino acid position 340 replaced with D;

and an immunologically effective amount of an adjuvant.

2. The recombinant combination vaccine composition of claim 1, wherein the first polypeptide consists of SEQ ID NO: 60 and the second polypeptide consists of SEQ ID NO: 64.

3. The recombinant combination vaccine composition of claim 1, wherein at least one of the polypeptides in the composition is a fusion protein comprising at least one other polypeptide sequence.

* * * * *